US011633394B2

(12) United States Patent
Chikkanna et al.

(10) Patent No.: US 11,633,394 B2
(45) Date of Patent: Apr. 25, 2023

(54) SUBSTITUTED ALKYNYLENE COMPOUNDS AS ANTICANCER AGENTS

(71) Applicant: Aurigene Oncology Limited, Bangalore (IN)

(72) Inventors: Dinesh Chikkanna, Bangalore (IN); Vinayak V. Khairnar, Nashik (IN); Muralidhara Ramachandra, Bangalore (IN); Leena Khare Satyam, Bangalore (IN)

(73) Assignee: AURIGENE ONCOLOGY LIMITED, Bangalore (IN)

( * ) Notice: Subject to any disclaimer, the term of this patent is extended or adjusted under 35 U.S.C. 154(b) by 0 days.

(21) Appl. No.: 16/962,941

(22) PCT Filed: Jan. 17, 2019

(86) PCT No.: PCT/IB2019/050387
§ 371 (c)(1),
(2) Date: Jul. 17, 2020

(87) PCT Pub. No.: WO2019/142126
PCT Pub. Date: Jul. 25, 2019

(65) Prior Publication Data
US 2021/0379055 A1    Dec. 9, 2021

(30) Foreign Application Priority Data
Jan. 17, 2018   (IN) .............................. 201841001978

(51) Int. Cl.
| | |
|---|---|
| A61K 45/06 | (2006.01) |
| C07C 237/24 | (2006.01) |
| C07C 275/26 | (2006.01) |
| C07C 311/11 | (2006.01) |
| C07D 205/04 | (2006.01) |
| C07D 207/16 | (2006.01) |
| C07D 211/58 | (2006.01) |
| C07D 211/72 | (2006.01) |
| C07D 231/56 | (2006.01) |
| C07D 261/04 | (2006.01) |
| C07D 295/215 | (2006.01) |
| C07D 333/28 | (2006.01) |
| C07D 401/04 | (2006.01) |
| A61K 31/496 | (2006.01) |
| A61P 35/00 | (2006.01) |
| A61K 31/17 | (2006.01) |
| A61K 31/439 | (2006.01) |
| A61K 31/4468 | (2006.01) |
| A61K 31/454 | (2006.01) |
| A61K 31/495 | (2006.01) |
| C07D 471/08 | (2006.01) |

(52) U.S. Cl.
CPC ............ *A61K 31/496* (2013.01); *A61K 31/17* (2013.01); *A61K 31/439* (2013.01); *A61K 31/4468* (2013.01); *A61K 31/454* (2013.01); *A61K 31/495* (2013.01); *A61K 45/06* (2013.01); *A61P 35/00* (2018.01); *C07C 237/24* (2013.01); *C07C 275/26* (2013.01); *C07C 311/11* (2013.01); *C07D 205/04* (2013.01); *C07D 207/16* (2013.01); *C07D 211/58* (2013.01); *C07D 211/72* (2013.01); *C07D 231/56* (2013.01); *C07D 261/04* (2013.01); *C07D 295/215* (2013.01); *C07D 333/28* (2013.01); *C07D 401/04* (2013.01); *C07D 471/08* (2013.01)

(58) Field of Classification Search
CPC .................................................. C07D 295/215
See application file for complete search history.

(56) References Cited

U.S. PATENT DOCUMENTS 7,368,572 B2    5/2008    Sendzik

FOREIGN PATENT DOCUMENTS

| WO | 2011153049 A1 | 12/2011 |
| WO | 2013170774 A1 | 11/2013 |

OTHER PUBLICATIONS

STN Registry Database entry for CAS RN 756508-80-2, Entered STN Oct. 4, 2004, Accessed Oct. 23, 2021.*
STN Registry database entry for CAS RN 184965-02-4, Entered STN Jan. 14, 1997, Accessed Jan. 15, 2022.*
STN Registry Database entry for CAS RN 756508-80-2, Entered STN Oct. 4, 2004, Accessed Dec. 2, 2022.*
STN Registry Database entry for CAS RN 756508-84-6, Entered STN Oct. 4, 2004, Accessed Dec. 2, 2022.*
CAS Registry, Accession No. 1381477-72-0, STN Entered Jul. 4, 2012, Asinex: "4-Piperidinecarboxamide, N-[1-[2-(4-isoquinolinyl)ethynyl]cyclohexyl]-1-(methylsulfonyl)-".

* cited by examiner

*Primary Examiner* — Alicia L Otton
(74) *Attorney, Agent, or Firm* — Honigman LLP; Heidi M. Berven; Andrew S. Chipouras

(57) ABSTRACT

The present invention relates to substituted alkynylene compounds represented by the compounds of formula (I), pharmaceutically acceptable salts and stereoisomers thereof. The present invention further provides the therapeutic uses of the compounds of formula (I) as anti-cancer agents.

30 Claims, No Drawings

SUBSTITUTED ALKYNYLENE COMPOUNDS AS ANTICANCER AGENTS

RELATED APPLICATIONS

This application is a national stage application under 35 U.S.C. § 371 of pending international application PCT/IB2019/050387, filed Jan. 17, 2019, which claims the benefit of priority to Indian provisional application number 201841001978, filed on Jan. 17, 2018, now abandoned; the contents of which are hereby incorporated by reference in their entirety.

FIELD OF THE INVENTION

The present invention relates to novel substituted alkynylene derivatives of formula (I) and pharmaceutically acceptable salts thereof.

The invention also provides pharmaceutically acceptable compositions comprising compounds of the present invention and methods of using said compositions in therapeutic uses thereof as anti-cancer agent, a chemotherapy agent, and an antiproliferative compound.

BACKGROUND OF THE INVENTION

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies show that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Kale, D., Immunology, 17.1-17.12) ($3^{rd}$ ed., Mosby, St. Louis, Mo., 1993).

There are various types of cancer which were reported in medical literature. Examples include cancer of the lung, colon, rectum, prostate, breast, brain, and intestine. The incidence of cancer progresses as the general population ages, as new cancers develop, and as susceptible populations (e.g., people infected with AIDS or excessively exposed to extreme environmental conditions) grow. Cancer can be treated by surgery, chemotherapy, radiation therapy, hormonal therapy, targeted therapy and synthetic lethality however, these options for the treatment of cancer are limited and they present most important side effects too. For example, in case of blood cancers (e.g., multiple myeloma), when conventional chemotherapy fails and bone-marrow transplantation fails to be an appropriate option, there are only few treatment options are available for the treatment. A tremendous demand therefore exists for new methods and compositions that can be used to treat patients with cancer.

There are several publications showing the variety of compounds useful as the anticancer agents such as WO2017177316A1 assigned to 3R VALO, S.E.C., titled "Aminobenzoic acid derivatives for use as anti-inflammatory agents, anti-metastatic agents and/or anticancer agents"; WO2016161342A2 assigned to Threshold Pharmaceuticals, titled "Nitrobenzyl derivatives of anti-cancer agents"; WO2008039489 A2 assigned to Celgene Corporation, titled "5-Substituted quinazolinone derivatives and compositions comprising and methods of using the same"; WO2005047266 A1 assigned to Lorus Therapeutics Inc. titled "Aryl imidazoles and their use as anti-cancer agents"; EP2632916B1 assigned to INST Medical W & E HALL (AU), titled "Novel anti-cancer agents"; have been published.

The publication by Ghorab et al. (Anticancer Agents Med Chem. 2017; 17(10):1411-1425) titled "Novel thiourea derivatives bearing sulfonamide moiety as anticancer agents through COX-2 inhibition" describes the anticancer activity of the target compounds was studied, via inhibition of COX-2 enzyme; Gupta M K et al. (World J Gastroenterol 2003; 9(6): 1144-1155) titled "Mechanism and its regulation of tumor-induced angiogenesis" describes the developmental status and evaluation of anti-angiogenic therapy in human clinical trials; Boichuk S et al. (Anti-cancer Drugs, 2016, 27, No. 7, 620-34) titled "Ethyl-2-amino-pyrrole-3-carboxylates are novel potent anticancer agents that affect tubulin polymerization, induce G2/M cell-cycle arrest, and effectively inhibit soft tissue cancer cell growth in vitro" presented structurally novel antimitotic compounds that show molecular and cellular mechanisms that are consistent with other antimitotic anticancer agents; D. Rodriguez-Hernandez (Eur. J. Med. Chem., 2016, 115, 257-67) titled "Novel hederagenin-triazolyl derivatives as potential anticancer agents" A series of novel aryl-1H-1,2,3-triazol-4-ylesters and amides derivatives of hederagenin has been synthesized; B. A. Dar et al. (Eur. J. Med. Chem., 2016, 111, 26-32) titled "Synthesis and screening of ursolic acid-benzylidine derivatives as potential anti-cancer agents" describes the promising biological activity of ursolic acid has led to its extensive chemical modification for the development of more potent antitumor agents.

A major aspect of the treatment of cancer is chemotherapy using anti-cancer agents. Nevertheless the huge progress has been made in this field, since the chemotherapy is rarely straightforward and there remains an unmet need to develop new and improved compounds, and compositions as anticancer agents which act by different mechanisms and pathways.

SUMMARY OF THE INVENTION

In one aspect according to the present invention, it comprises alkynylene compounds of formula (I):

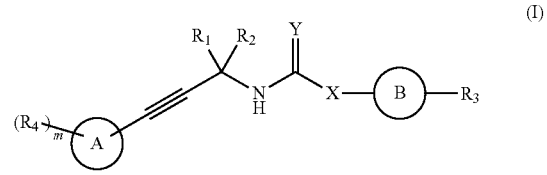

or a pharmaceutically acceptable salt or a stereoisomer thereof; wherein,

A represents aryl or heteroaryl;

X represents N—$R_y$, or absent;

Y represents O, S or NCN;

B represents aryl, cycloalkyl or heterocycloalkyl; wherein the aryl, cycloalkyl or heterocycloalkyl are optionally substituted with one or more groups selected from alkyl, halo and oxo;

$R_1$ represents alkyl; $R_2$ represents hydrogen or alkyl; or $R_1$ and $R_2$ together with the carbon atoms to which they are attached form 3- to 5-membered cycloalkyl ring;

$R_3$ represents —C(O)$R_a$, —S(O)$_2R_a$, —NHS(O)$_2R_a$, —N$R_b$C(O)$R_a$, =NO$R_a$, heteroaryl, heterocycloalkyl or (heterocycloalkyl)alkyl-; wherein the heteroaryl and heterocycloalkyl are optionally substituted with one or more group selected from alkyl, halo, oxo and —C(O)$R_x$;

$R_4$ represents alkyl, halo, haloalkyl, cyano, alkoxy, aryloxy, alkoxyaryl, hydroxyalkyl, acetylene, acyl, hydroxy, cycloalkyl or —N($R_x$)$_2$; wherein the cycloalkyl is optionally substituted with alkyl;

$R_a$ represents alkyl, alkenyl, haloalkyl, cycloalkyl or heterocycloalkyl; wherein the alkyl, alkenyl, haloalkyl, cycloalkyl and heterocycloalkyl are optionally substituted with one or more groups selected from alkyl, halo, aryl, cycloalkyl, haloalkyl, amino, amido, alkylamino, aminoalkyl, hydroxyl, cyano, alkoxy, alkoxyaryl, aryloxy, hydroxyalkyl, carboxylic acid, ester, thioester, oxo(=O) and —C(O)$R_x$;

$R_x$ represents hydrogen, alkyl, alkenyl, acyl or —C(O)-cycloalkyl;

$R_y$ represents hydrogen or alkyl;

$R_b$ represents hydrogen, alkyl or alkenyl;

'm' represents 0, 1, 2 or 3.

In yet another aspect, the present invention provides a pharmaceutical composition comprising the compound of formula (I), and at least one pharmaceutically acceptable excipient such as a pharmaceutically acceptable carrier or diluent.

In yet another aspect, the present invention relates to a method of treatment of cancer, which method comprises the administration of an effective amount of a compound of formula (I) as defined hereinbefore, or a pharmaceutically acceptable salt or solvate, or a pharmaceutically functional derivative thereof, to a patient in need of such treatment;

In yet further aspect of the present application, it provides use of alkynylene compound of formula (I) for treatment of cancer or as an adjuvant/neo-adjuvant therapeutic agent in the treatment of cancer;

DETAILED DESCRIPTION OF THE INVENTION

The present invention provides substituted alkynylene compounds, referred as compounds of formula (I), which are useful as anti-cancer agents. The present invention further provides pharmaceutical compositions comprising the said compounds and their derivatives as therapeutic agents.

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus it is intended that the present invention include such modifications and variations and their equivalents. Other objects, features and aspects of the present invention are disclosed in or are obvious from, the following detailed description. It is to be understood by one of ordinary skill in the art that the present discussion is a description of exemplary embodiments only and is not to be construed as limiting the broader aspects of the present invention.

In one embodiment, the present invention provides a compound of formula (I):

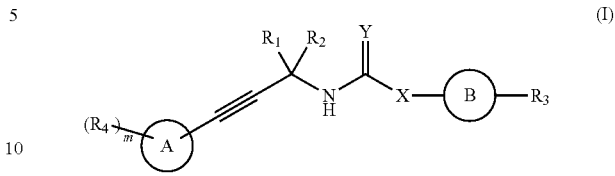

or a pharmaceutically acceptable salt or a stereoisomer thereof; wherein,

A represents aryl or heteroaryl;

X represents N—$R_y$, or absent;

Y represents O, S or NCN;

B represents aryl, cycloalkyl or heterocycloalkyl; wherein the aryl, cycloalkyl or heterocycloalkyl are optionally substituted with one or more groups selected from alkyl, halo and oxo;

$R_1$ represents alkyl; and $R_2$ represents hydrogen or alkyl; or $R_1$ and $R_2$ together with the carbon atoms to which they are attached form 3- to 5-membered cycloalkyl ring;

$R_3$ represents —C(O)$R_a$, —S(O)$_2R_a$, —NHS(O)$_2R_a$, —N$R_b$C(O)$R_a$, =NO$R_a$, heteroaryl, heterocycloalkyl or (heterocycloalkyl)alkyl-; wherein the heteroaryl and heterocycloalkyl are optionally substituted with one or more group selected from alkyl, halo, oxo and —C(O)$R_x$;

$R_4$ represents alkyl, halo, haloalkyl, cyano, alkoxy, aryloxy, alkoxyaryl, hydroxyalkyl, acetylene, acyl, hydroxy, cycloalkyl or —N($R_x$)$_2$; wherein the cycloalkyl is optionally substituted with alkyl;

$R_a$ represents alkyl, alkenyl, haloalkyl, cycloalkyl or heterocycloalkyl; wherein the alkyl, alkenyl, haloalkyl, cycloalkyl and heterocycloalkyl are optionally substituted with one or more groups selected from alkyl, halo, aryl, cycloalkyl, haloalkyl, amino, amido, alkylamino, aminoalkyl, hydroxyl, cyano, alkoxy, alkoxyaryl, aryloxy, hydroxyalkyl, carboxylic acid, ester, thioester, oxo(=O) and —C(O)$R_x$;

$R_x$ represents hydrogen, alkyl, alkenyl, acyl or —C(O)-cycloalkyl;

$R_y$ represents hydrogen or alkyl;

$R_b$ represents hydrogen, alkyl or alkenyl;

'm' represents 0, 1, 2 or 3.

According to one embodiment, specifically provided is compound of formula (I) or a pharmaceutically acceptable salt or stereoisomer thereof, wherein X represents NH.

In certain embodiments, X is absent.

According to one embodiment, specifically provided is compound of formula (I) or a pharmaceutically acceptable salt or stereoisomer thereof, wherein Y represents O.

According to one embodiment, specifically provided is compound of formula (I) or a pharmaceutically acceptable salt or stereoisomer thereof, wherein A represents aryl.

In certain embodiments, A represents phenyl.

In certain embodiments, A represents phenyl which is substituted by 'm' occurrences of $R_4$. In certain embodiments, m represents 1, 2 or 3. In certain particular embodiments, 'm' represents 1 or 2.

According to one embodiment, specifically provided is compound of formula (I) or a pharmaceutically acceptable salt or stereoisomer thereof, wherein B represents cycloalkyl or heterocycloalkyl are optionally substituted with one or more groups selected from alkyl, halo or oxo.

In certain embodiments, B represents cycloalkyl or heterocycloalkyl; wherein heterocycloalkyl is optionally substituted with oxo.

In certain embodiments, B represents 5 to 6-membered heterocycloalkyl.

According to one embodiment, specifically provided is compound of formula (I) or a pharmaceutically acceptable salt or stereoisomer thereof, wherein $R_1$ represents alkyl; and $R_2$ represents hydrogen.

In certain embodiments, $R_1$ and $R_2$ together with the carbon atoms to which they are attached form 3 to 5 membered cycloalkyl ring.

In certain embodiments, $R_1$ and $R_2$ together with the carbon atoms to which they are attached form cyclopropyl or cyclopentyl ring.

In certain embodiments, $R_1$ and $R_2$ together with the carbon atoms to which they are attached form cyclopropyl.

According to one embodiment, specifically provided is compound of formula (I) or a pharmaceutically acceptable salt or stereoisomer thereof, wherein $R_3$ represents —C(O)$R_a$, —NHS(O)$_2R_a$ or —NR$_b$C(O)R$_a$.

According to one embodiment, specifically provided is compound of formula (I) or a pharmaceutically acceptable salt or stereoisomer thereof, wherein $R_3$ represents —C(O)$R_a$; wherein $R_a$ is as defined in compound of formula (I).

In certain embodiments, $R_a$ represents alkenyl, cycloalkyl or heterocycloalkyl; wherein the alkenyl, cycloalkyl and heterocycloalkyl are optionally substituted with one or more group selected from alkyl, halo, aryl, cycloalkyl, haloalkyl, amino, amido, alkylamino, aminoalkyl, hydroxyl, cyano, alkoxy, alkoxyaryl, aryloxy, hydroxyalkyl, carboxylic acid, ester, thioester or oxo(=O) or —C(O)$R_x$.

According to one embodiment, specifically provided is compound of formula (I) or a pharmaceutically acceptable salt or stereoisomer thereof, wherein $R_3$ represents heterocycloalkyl optionally substituted with —C(O)$R_x$.

In certain embodiments, $R_b$ represents hydrogen, or alkyl.

According to one embodiment, specifically provided is compound of formula (I) or a pharmaceutically acceptable salt or stereoisomer thereof, wherein $R_4$ represents alkyl, halo, haloalkyl or cycloalkyl, wherein the cycloalkyl is optionally substituted with alkyl.

In yet another embodiment, the present invention provides compound of formula (IA):

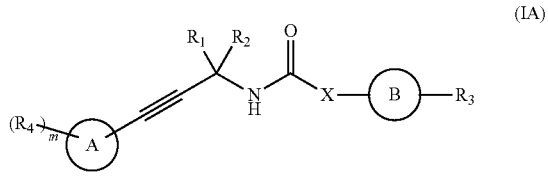

or a pharmaceutically acceptable salt or stereoisomer thereof;
wherein A, $R_1$, $R_2$, $R_3$, $R_4$, B, X and m are as defined in compound of formula (I).

According to one embodiment, specifically provided is compound of formula (IA) or a pharmaceutically acceptable salt or stereoisomer thereof, wherein X represents NH.

According to one embodiment, specifically provided is compound of formula (IA) or a pharmaceutically acceptable salt or stereoisomer thereof, wherein A represents aryl.

In certain embodiments, A represents phenyl.

According to one embodiment, specifically provided is compound of formula (IA) or a pharmaceutically acceptable salt or stereoisomer thereof, wherein B represents cycloalkyl or heterocycloalkyl are optionally substituted with one or more groups selected from alkyl, halo or oxo.

According to one embodiment, specifically provided is compound of formula (IA) or a pharmaceutically acceptable salt or stereoisomer thereof, wherein B represents 5- or 6-membered cycloalkyl.

According to one embodiment, specifically provided is compound of formula (IA) or a pharmaceutically acceptable salt or stereoisomer thereof, wherein B represents cyclopentyl or cyclohexyl ring.

According to one embodiment, specifically provided is compound of formula (IA) or a pharmaceutically acceptable salt or stereoisomer thereof, wherein $R_3$ represents —C(O)$R_a$, —S(O)$_2R_a$, —NHS(O)$_2R_a$, —NR$_b$C(O)R$_a$, or =NOR$_a$.

According to one embodiment, specifically provided is compound of formula (IA) or a pharmaceutically acceptable salt or stereoisomer thereof, wherein $R_3$ represents —NHS(O)$_2R_a$, or —NR$_b$C(O)R$_a$; wherein $R_a$, and $R_b$ are as defined in compound of formula (I).

According to one embodiment, specifically provided is compound of formula (IA) or a pharmaceutically acceptable salt or stereoisomer thereof, wherein $R_4$ represents alkyl, halo, haloalkyl or cycloalkyl, wherein the cycloalkyl is optionally substituted with alkyl.

In yet another embodiment, the present invention provides compound of formula (IB):

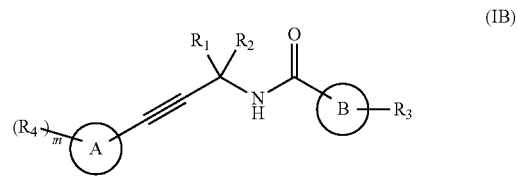

or a pharmaceutically acceptable salt or stereoisomer thereof;
wherein A, $R_1$, $R_2$, $R_3$, $R_4$, B, and m are as defined in compound of formula (I).

According to one embodiment, specifically provided is compound of formula (IB) or a pharmaceutically acceptable salt or stereoisomer thereof, wherein A represents aryl.

According to one embodiment, specifically provided is compound of formula (IB) or a pharmaceutically acceptable salt or stereoisomer thereof, wherein B represents cycloalkyl or heterocycloalkyl are optionally substituted with one or more groups selected from alkyl, halo or oxo.

According to one embodiment, specifically provided is compound of formula (IB) or a pharmaceutically acceptable salt or stereoisomer thereof, wherein B represents heterocycloalkyl optionally substituted with one or more groups selected from alkyl, halo or oxo.

According to one embodiment, specifically provided is compound of formula (IB) or a pharmaceutically acceptable salt or stereoisomer thereof, wherein B represents 5- or 6-membered heterocycloalkyl.

According to one embodiment, specifically provided is compound of formula (IB) or a pharmaceutically acceptable salt or stereoisomer thereof, wherein $R_3$ represents heterocycloalkyl optionally substituted with —C(O)$R_x$.

According to one embodiment, specifically provided is compound of formula (IB) or a pharmaceutically acceptable salt or stereoisomer thereof, wherein $R_4$ represents alkyl, halo, haloalkyl or cycloalkyl, wherein the cycloalkyl is optionally substituted with alkyl.

In yet another embodiment, the present invention provides compound of formula (IC):

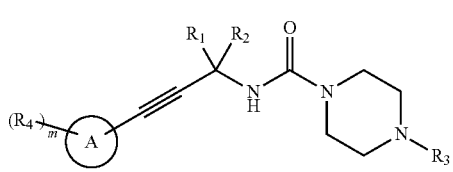

(IC)

or a pharmaceutically acceptable salt or stereoisomer thereof;

wherein A, $R_1$, $R_2$, $R_3$, $R_4$ and m are as defined in compound of formula (I).

According to one embodiment, specifically provided is compound of formula (IC) or a pharmaceutically acceptable salt or stereoisomer thereof, wherein A represents aryl.

According to one embodiment, specifically provided is compound of formula (IC) or a pharmaceutically acceptable salt or stereoisomer thereof, wherein $R_1$ represents alkyl; $R_2$ represents hydrogen or alkyl.

According to one embodiment, specifically provided is compound of formula (IC) or a pharmaceutically acceptable salt or stereoisomer thereof, wherein $R_1$ and $R_2$ together with the carbon atoms to which they are attached form cyclopropyl or cyclopentyl ring.

According to one embodiment, specifically provided is compound of formula (IC) or a pharmaceutically acceptable salt or stereoisomer thereof, wherein $R_3$ represents optionally substituted heteroaryl, heterocycloalkyl or (heterocycloalkyl)alkyl-.

According to one embodiment, specifically provided is compound of formula (IC) or a pharmaceutically acceptable salt or stereoisomer thereof, wherein $R_3$ represents heterocycloalkyl optionally substituted with —C(O)$R_x$.

According to one embodiment, specifically provided is compound of formula (IC) or a pharmaceutically acceptable salt or stereoisomer thereof, wherein $R_3$ represents heterocycloalkyl optionally substituted with —C(O)$R_x$.

According to one embodiment, specifically provided is compound of formula (IC) or a pharmaceutically acceptable salt or stereoisomer thereof, wherein $R_4$ represents alkyl, halo, haloalkyl or cycloalkyl, wherein the cycloalkyl is optionally substituted with alkyl.

According to one embodiment, specifically provided is compound of formula (IC) or a pharmaceutically acceptable salt or stereoisomer thereof, wherein 'm' represents 2.

In yet another embodiment, the present invention provides compound of formula (ID):

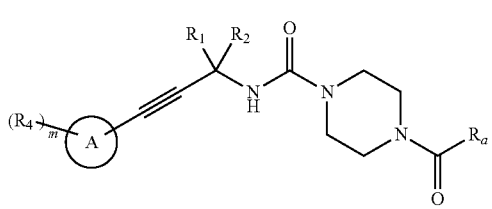

(ID)

or a pharmaceutically acceptable salt or stereoisomer thereof;

wherein A, $R_1$, $R_2$, $R_4$, $R_a$ and 'm' are as defined in compound of formula (I).

According to one embodiment, specifically provided is compound of formula (ID) or a pharmaceutically acceptable salt or stereoisomer thereof, wherein A represents aryl.

According to one embodiment, specifically provided is compound of formula (ID) or a pharmaceutically acceptable salt or stereoisomer thereof, wherein $R_1$ represents alkyl; and $R_2$ independently represents hydrogen.

According to one embodiment, specifically provided is compound of formula (ID) or a pharmaceutically acceptable salt or stereoisomer thereof, wherein $R_a$ represents alkenyl, cycloalkyl or heterocycloalkyl; wherein the alkenyl, cycloalkyl and heterocycloalkyl are optionally substituted with one or more groups selected from halo, aryl, haloalkyl or carboxylic acid.

According to one embodiment, specifically provided is compound of formula (ID) or a pharmaceutically acceptable salt or stereoisomer thereof, wherein $R_4$ represents alkyl, halo, haloalkyl or cycloalkyl, wherein the cycloalkyl is optionally substituted with alkyl.

According to one embodiment, specifically provided is compound of formula (ID) or a pharmaceutically acceptable salt or stereoisomer thereof, wherein $R_4$ represents halo.

According to one embodiment, specifically provided is compound of formula (ID) or a pharmaceutically acceptable salt or stereoisomer thereof, wherein m represents 2.

In yet another embodiment, the present invention provides compounds of formula (IE):

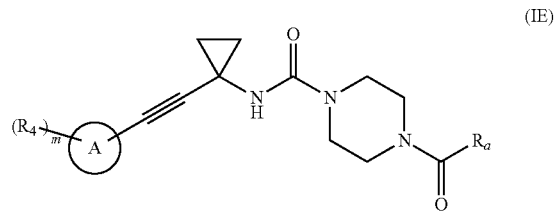

(IE)

or a pharmaceutically acceptable salt or stereoisomer thereof;

wherein A, $R_4$, $R_a$ and m are as defined in compound of formula (I).

According to one embodiment, specifically provided is compound of formula (IE) or a pharmaceutically acceptable salt or stereoisomer thereof, wherein A represents aryl.

According to one embodiment, specifically provided is compound of formula (IE) or a pharmaceutically acceptable salt or stereoisomer thereof, wherein $R_a$ represents alkenyl, cycloalkyl or heterocycloalkyl; wherein the alkenyl, cycloalkyl and heterocycloalkyl are optionally substituted with one or more groups selected from halo, aryl, haloalkyl or carboxylic acid.

According to one embodiment, specifically provided is compound of formula (IE) or a pharmaceutically acceptable salt or stereoisomer thereof, wherein $R_4$ represents halo.

According to one embodiment, specifically provided is compound of formula (IE) or a pharmaceutically acceptable salt or stereoisomer thereof, wherein m represents 2.

In yet another embodiment, the present invention provides compound of formula (IF):

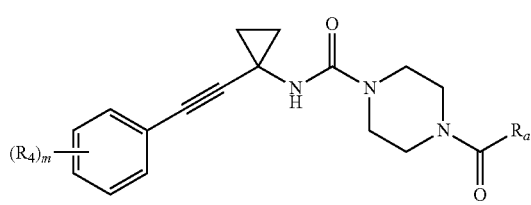

(IF)

or a pharmaceutically acceptable salt or stereoisomer thereof;

wherein $R_4$, $R_a$ and m are as defined in compound of formula (I).

According to one embodiment, specifically provided is compound of formula (IF) or a pharmaceutically acceptable salt or stereoisomer thereof, wherein $R_a$ represents alkenyl, cycloalkyl or heterocycloalkyl; wherein the alkenyl, cycloalkyl and heterocycloalkyl are optionally substituted with one or more groups selected from halo, aryl, haloalkyl or carboxylic acid.

According to one embodiment, specifically provided is compound of formula (IF) or a pharmaceutically acceptable salt or stereoisomer thereof, wherein $R_4$ represents halo.

According to one embodiment, specifically provided is compound of formula (IF) or a pharmaceutically acceptable salt or stereoisomer thereof, wherein m represents 2.

In yet another embodiment, the present invention provides compound of formula (IG):

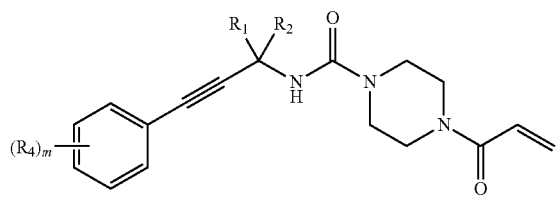

(IG)

or a pharmaceutically acceptable salt or stereoisomer thereof;

wherein $R_1$, $R_2$, $R_4$ and m are as defined in compound of formula (I).

According to one embodiment, specifically provided is compound of formula (IG) or a pharmaceutically acceptable salt or stereoisomer thereof, wherein $R_1$ represents alkyl; $R_2$ independently represents hydrogen.

According to one embodiment, specifically provided is compound of formula (IG) or a pharmaceutically acceptable salt or stereoisomer thereof, wherein $R_4$ represents halo.

According to one embodiment, specifically provided is compound of formula (IG) or a pharmaceutically acceptable salt or stereoisomer thereof, wherein m represents 2.

In yet another embodiment, the present invention provides compound of formula (IH):

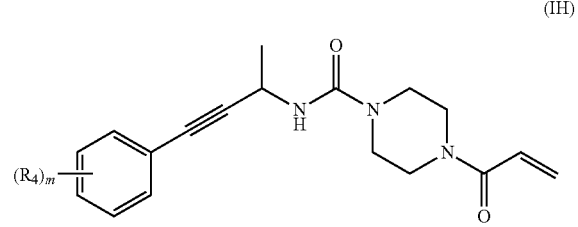

(IH)

or a pharmaceutically acceptable salt or stereoisomer thereof;

wherein $R_4$ and m are as defined in compound of formula (I).

According to one embodiment, specifically provided is compound of formula (IH) or a pharmaceutically acceptable salt or stereoisomer thereof, wherein $R_4$ represents halo.

According to one embodiment, specifically provided is compound of formula (IH) or a pharmaceutically acceptable salt or stereoisomer thereof, wherein $R_4$ represents chloro.

According to one embodiment, specifically provided is compound of formula (IH) or a pharmaceutically acceptable salt or stereoisomer thereof, wherein m represents 2.

According to yet another embodiment, the present invention provides a compound, or a pharmaceutically acceptable salt or a stereoisomer thereof, selected from:

| Example | Structure |
|---|---|
| 1 | ![structure](Cl, Cl-phenyl-C≡C-CH(CH3)-NH-C(O)-piperazine-C(O)-CH=CH2) |
| 1a | ![structure](Cl, Cl-phenyl-C≡C-CH(CH3)-NH-C(O)-piperazine-C(O)-CH=CH2) (Isomer-1) |

-continued
| Example | Structure |
|---|---|
| 1b | 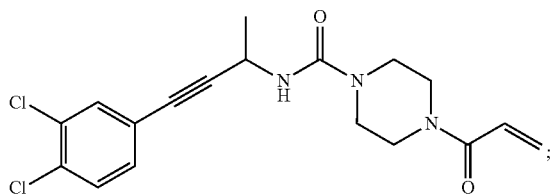 [SMILES: C=CC(=O)N1CCN(C(=O)NC(C)C#Cc2ccc(Cl)c(Cl)c2)CC1]<br>(Isomer-2) |
| 2 | 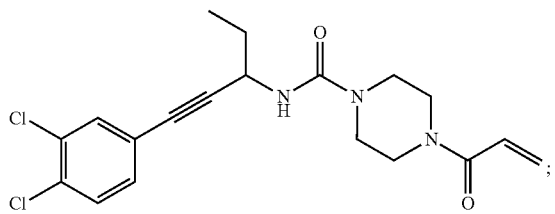 [SMILES: C=CC(=O)N1CCN(C(=O)NC(C#Cc2ccc(Cl)c(Cl)c2)CC)CC1] |
| 2a | 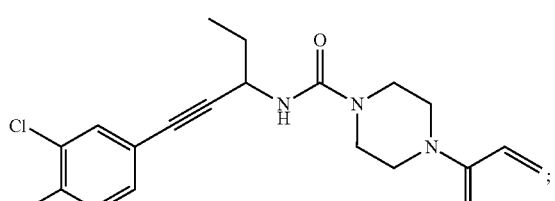<br>(Isomer-1) |
| 2b | 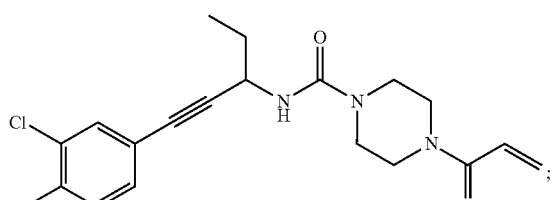<br>(Isomer-2) |
| 3 | 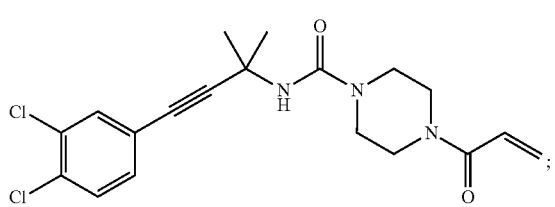 [SMILES: C=CC(=O)N1CCN(C(=O)NC(C)(C)C#Cc2ccc(Cl)c(Cl)c2)CC1] |
| 4 | 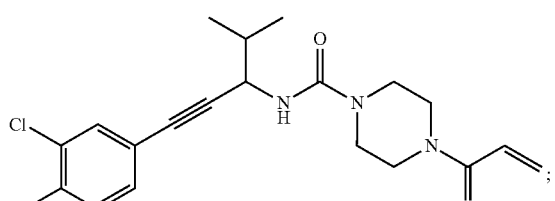 |
| 5 | 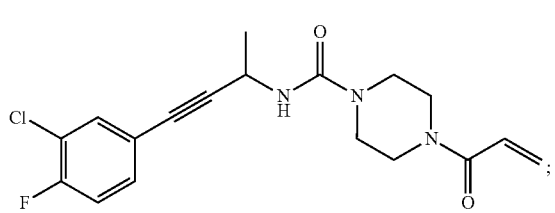 [SMILES: C=CC(=O)N1CCN(C(=O)NC(C)C#Cc2ccc(F)c(Cl)c2)CC1] |

-continued

| Example | Structure |
|---|---|
| 6 | 3-chloro-4-(trifluoromethyl)phenyl-C≡C-CH(CH₃)-NH-C(O)-N(piperazine)-C(O)-CH=CH₂ |
| 7 | 3-chloro-4-methylphenyl-C≡C-CH(CH₃)-NH-C(O)-N(piperazine)-C(O)-CH=CH₂ |
| 8 | 3,4-dichlorophenyl-C≡C-CH(CH₃)-NH-C(O)-N(piperazine)-(azetidine)-C(O)-CH=CH₂ |
| 9 | naphthalen-2-yl-C≡C-CH(CH₃)-NH-C(O)-N(piperazine)-C(O)-CH=CH₂ |
| 10 | 1H-indazol-5-yl-C≡C-CH(CH₃)-NH-C(O)-N(piperazine)-C(O)-CH=CH₂ |
| 11 | 1-methyl-1H-indazol-4-yl-C≡C-CH(CH₃)-NH-C(O)-N(piperazine)-C(O)-CH=CH₂ |
| 12 | 3,4-dichlorophenyl-C≡C-CH(CH₃)-NH-C(O)-N(piperidine)-NH-C(O)-CH=CH₂ |

-continued
| Example | Structure |
|---|---|
| 13 | 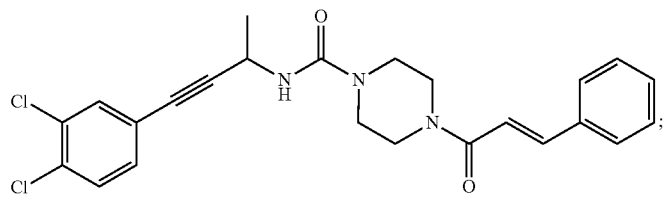 [SMILES: CC(C#Cc1ccc(Cl)c(Cl)c1)NC(=O)N1CCN(C(=O)/C=C/c2ccccc2)CC1] |
| 14 | 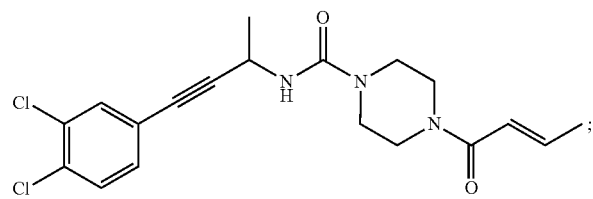 [SMILES: C/C=C/C(=O)N1CCN(C(=O)NC(C)C#Cc2ccc(Cl)c(Cl)c2)CC1] |
| 15 | 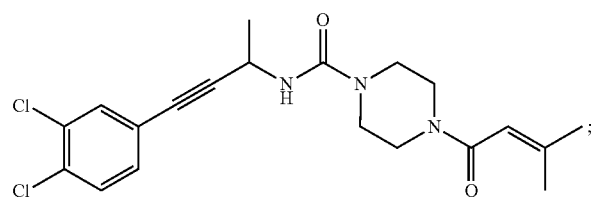 [SMILES: CC(C)=CC(=O)N1CCN(C(=O)NC(C)C#Cc2ccc(Cl)c(Cl)c2)CC1] |
| 16 | 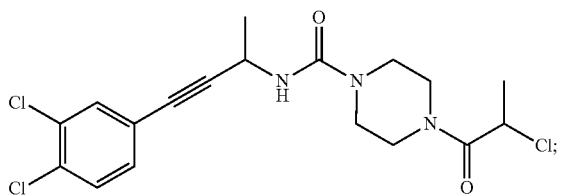 [SMILES: CC(C#Cc1ccc(Cl)c(Cl)c1)NC(=O)N1CCN(C(=O)C(C)Cl)CC1] |
| 17 | 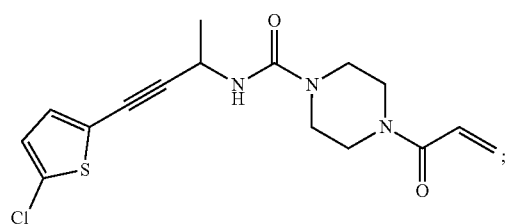 [SMILES: C=CC(=O)N1CCN(C(=O)NC(C)C#Cc2ccc(Cl)s2)CC1] |
| 18 | 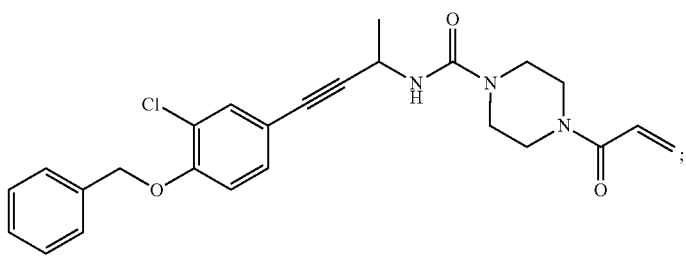 [SMILES: C=CC(=O)N1CCN(C(=O)NC(C)C#Cc2ccc(OCc3ccccc3)c(Cl)c2)CC1] |
| 19 | 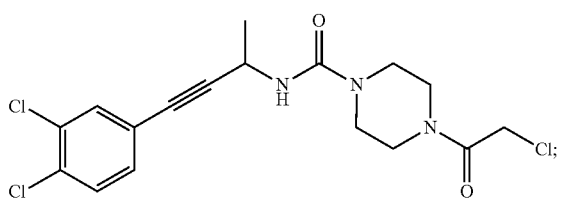 [SMILES: CC(C#Cc1ccc(Cl)c(Cl)c1)NC(=O)N1CCN(C(=O)CCl)CC1] |

-continued
| Example | Structure |
|---|---|
| 20 | 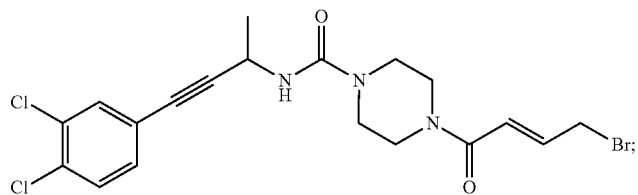 [SMILES: CC(C#Cc1ccc(Cl)c(Cl)c1)NC(=O)N1CCN(C(=O)/C=C/CBr)CC1] |
| 21 | 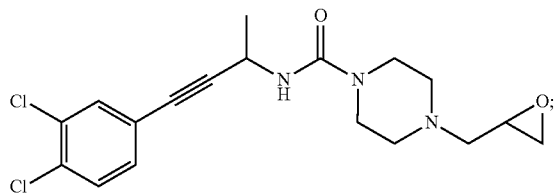 [SMILES: CC(C#Cc1ccc(Cl)c(Cl)c1)NC(=O)N1CCN(CC2CO2)CC1] |
| 22 | 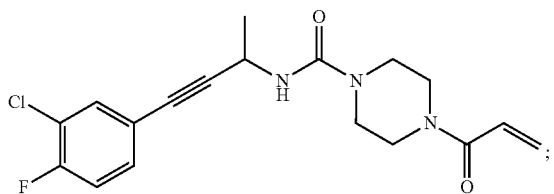 [SMILES: C=CC(=O)N1CCN(C(=O)NC(C)C#Cc2ccc(F)c(Cl)c2)CC1] |
| 23 | 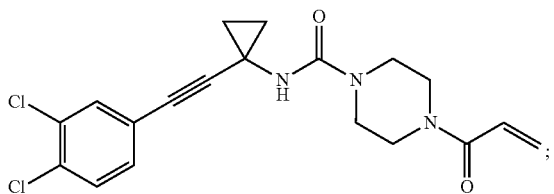 [SMILES: C=CC(=O)N1CCN(C(=O)NC2(C#Cc3ccc(Cl)c(Cl)c3)CC2)CC1] |
| 24 | 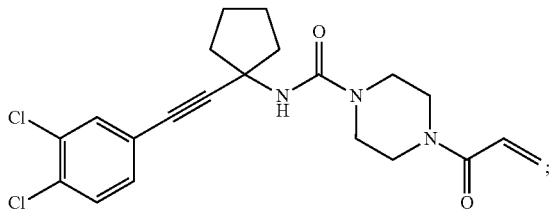 [SMILES: C=CC(=O)N1CCN(C(=O)NC2(C#Cc3ccc(Cl)c(Cl)c3)CCCC2)CC1] |
| 25 | 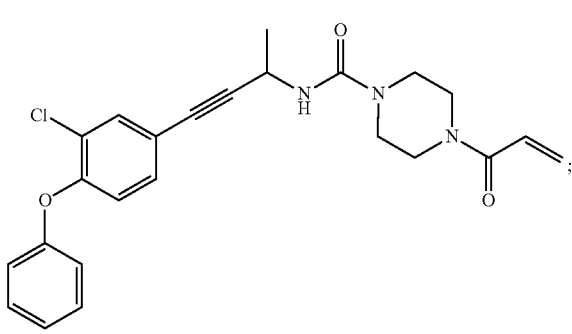 [SMILES: C=CC(=O)N1CCN(C(=O)NC(C)C#Cc2ccc(Oc3ccccc3)c(Cl)c2)CC1] |
| 26 | 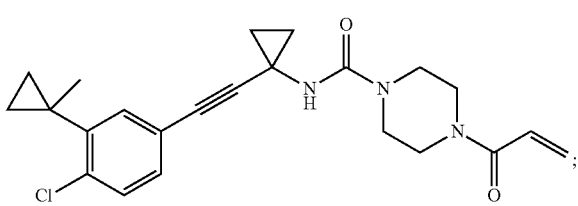 [SMILES: C=CC(=O)N1CCN(C(=O)NC2(C#Cc3ccc(Cl)c(C4(C)CC4)c3)CC2)CC1] |

-continued
| Example | Structure |
|---|---|
| 27 | 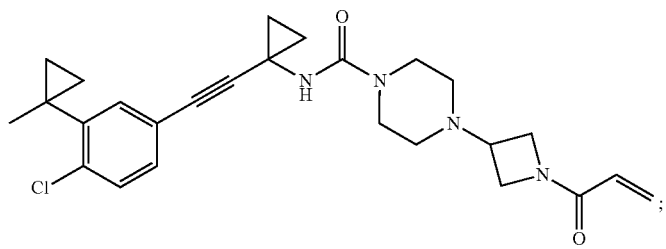 [SMILES: C=CC(=O)N1CC(N2CCN(C(=O)NC3(C#Cc4ccc(Cl)c(C5(C)CC5)c4)CC3)CC2)C1] |
| 28 | 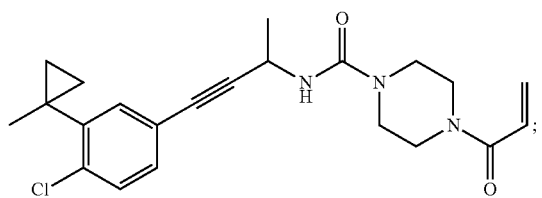 [SMILES: C=CC(=O)N1CCN(C(=O)NC(C)C#Cc2ccc(Cl)c(C3(C)CC3)c2)CC1] |
| 29 | 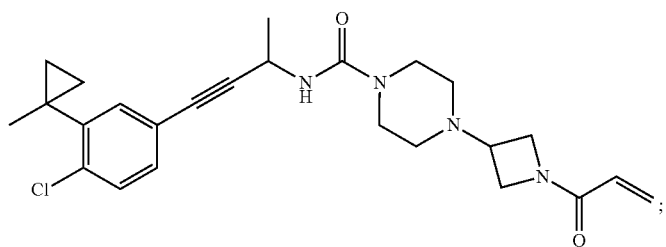 [SMILES: C=CC(=O)N1CC(N2CCN(C(=O)NC(C)C#Cc3ccc(Cl)c(C4(C)CC4)c3)CC2)C1] |
| 30 | 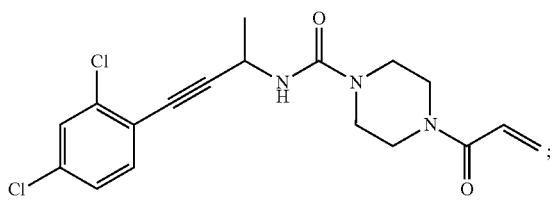 [SMILES: C=CC(=O)N1CCN(C(=O)NC(C)C#Cc2ccc(Cl)cc2Cl)CC1] |
| 31 | 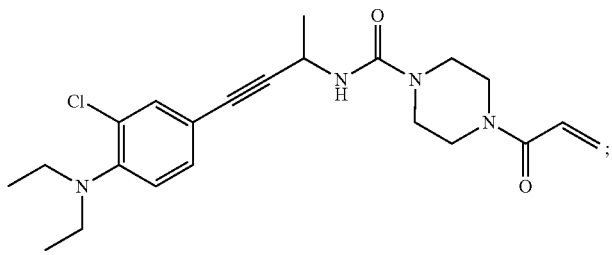 [SMILES: C=CC(=O)N1CCN(C(=O)NC(C)C#Cc2ccc(N(CC)CC)c(Cl)c2)CC1] |
| 32 | 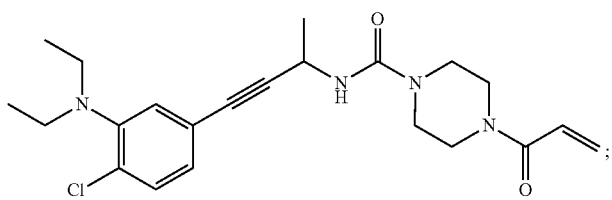 [SMILES: C=CC(=O)N1CCN(C(=O)NC(C)C#Cc2ccc(Cl)c(N(CC)CC)c2)CC1] |

-continued
| Example | Structure |
|---|---|
| 33 | 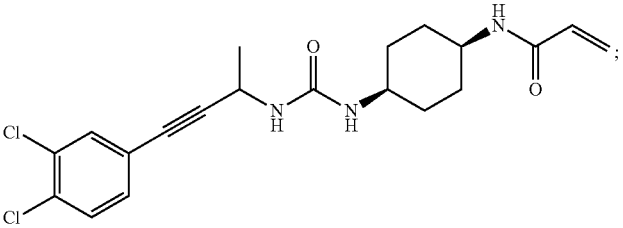 [SMILES: C=CC(=O)N[C@H]1CC[C@@H](NC(=O)NC(C)C#Cc2ccc(Cl)c(Cl)c2)CC1] |
| 34 | 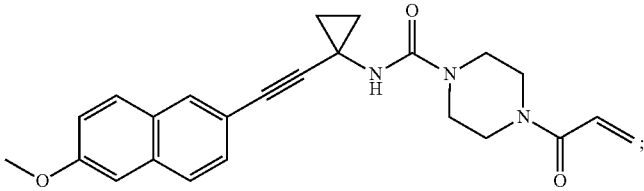 [SMILES: C=CC(=O)N1CCN(C(=O)NC2(C#Cc3ccc4cc(OC)ccc4c3)CC2)CC1] |
| 35 | 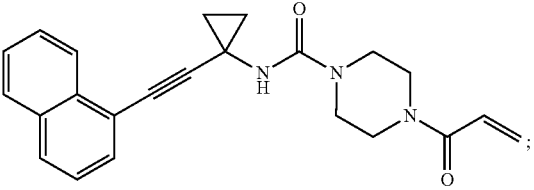 |
| 36 | 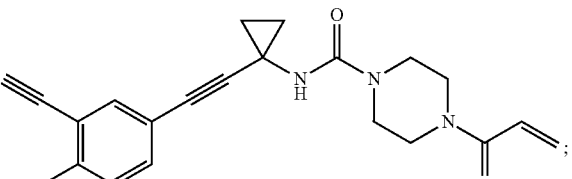 |
| 37 | 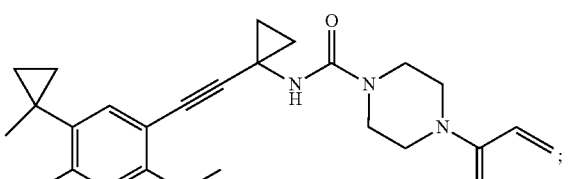 |
| 38 | 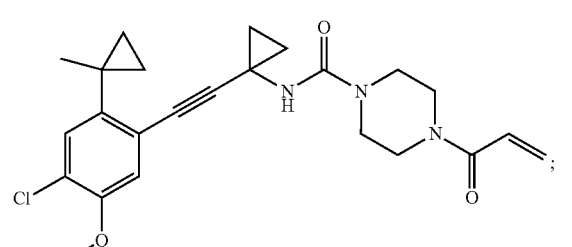 |
| 39 | 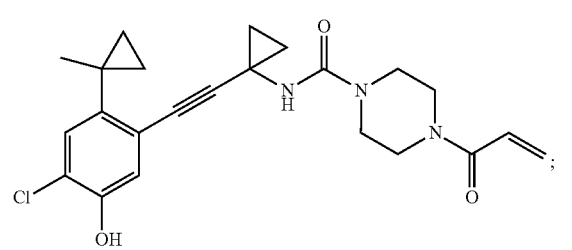 [SMILES: C=CC(=O)N1CCN(C(=O)NC2(C#Cc3cc(O)c(Cl)cc3C3(C)CC3)CC2)CC1] |

-continued
| Example | Structure |
|---|---|
| 40 | 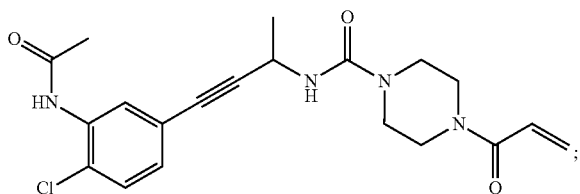 [SMILES: C=CC(=O)N1CCN(C(=O)NC(C)C#Cc2ccc(Cl)c(NC(C)=O)c2)CC1] |
| 41 | 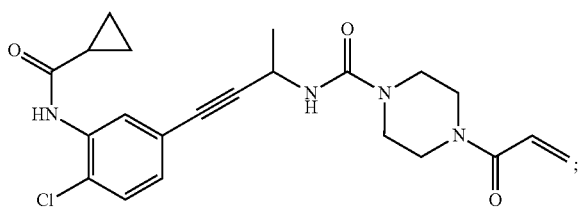 [SMILES: C=CC(=O)N1CCN(C(=O)NC(C)C#Cc2ccc(Cl)c(NC(=O)C3CC3)c2)CC1] |
| 42 | 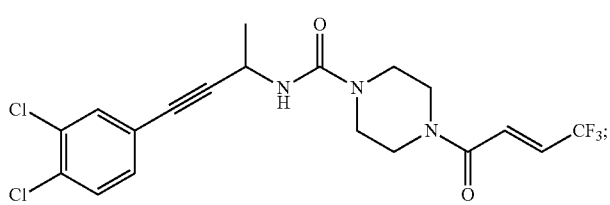 |
| 42a | 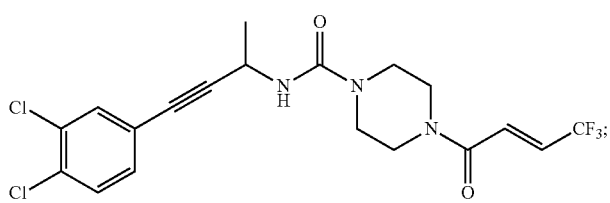 [SMILES: CC(C#Cc1ccc(Cl)c(Cl)c1)NC(=O)N1CCN(C(=O)/C=C/C(F)(F)F)CC1]<br>(Isomer-1) |
| 42b | 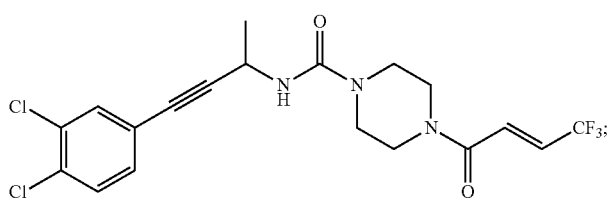<br>(Isomer-2) |
| 43 | 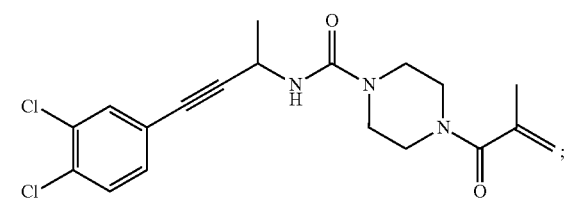 [SMILES: C=C(C)C(=O)N1CCN(C(=O)NC(C)C#Cc2ccc(Cl)c(Cl)c2)CC1] |
| 44 | 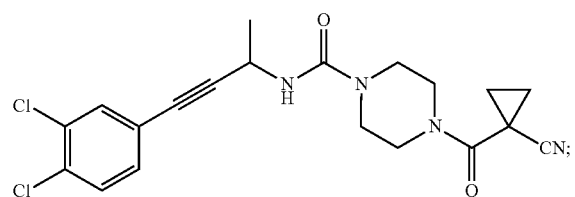 [SMILES: CC(C#Cc1ccc(Cl)c(Cl)c1)NC(=O)N1CCN(C(=O)C2(C#N)CC2)CC1] |

-continued
| Example | Structure |
|---|---|
| 45 | 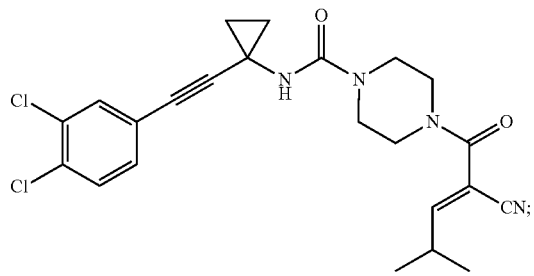 [SMILES: CC(C)/C=C(\C#N)C(=O)N1CCN(C(=O)NC2(C#Cc3ccc(Cl)c(Cl)c3)CC2)CC1] |
| 46 | 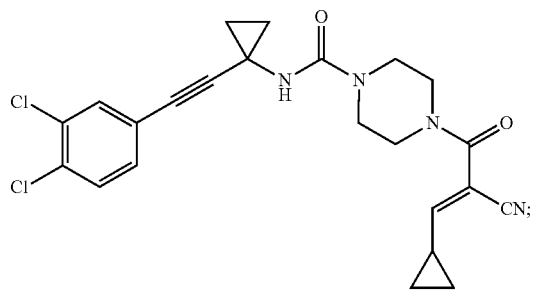 [SMILES: N#C/C(=C\C1CC1)C(=O)N1CCN(C(=O)NC2(C#Cc3ccc(Cl)c(Cl)c3)CC2)CC1] |
| 47 | 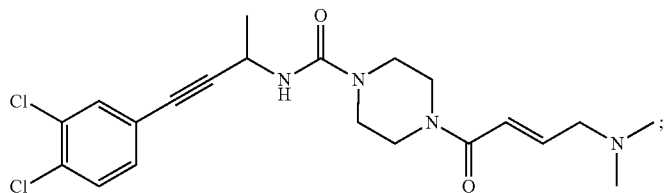 [SMILES: CC(C#Cc1ccc(Cl)c(Cl)c1)NC(=O)N1CCN(C(=O)/C=C/CN(C)C)CC1] |
| 48a | 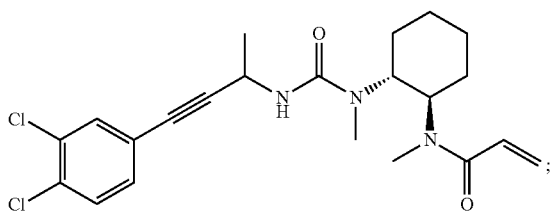 (Isomer-1) |
| 48b | 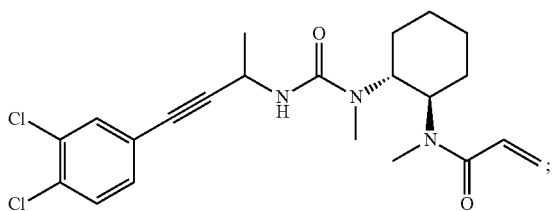 (Isomer-2) |
| 49 | 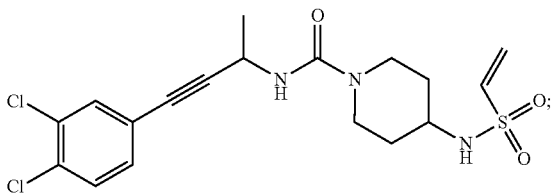 [SMILES: C=CS(=O)(=O)NC1CCN(C(=O)NC(C)C#Cc2ccc(Cl)c(Cl)c2)CC1] |

-continued
| Example | Structure |
|---------|-----------|
| 50 | 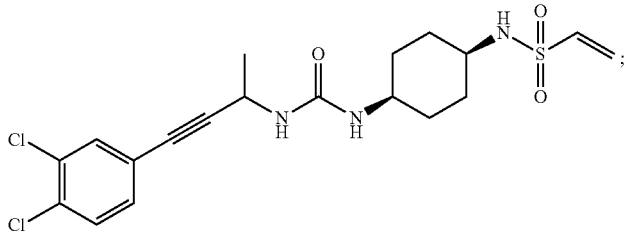 [SMILES: C=CS(=O)(=O)N[C@H]1CC[C@@H](NC(=O)NC(C)C#Cc2ccc(Cl)c(Cl)c2)CC1] |
| 51 | 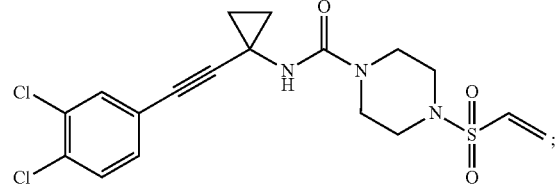 [SMILES: C=CS(=O)(=O)N1CCN(C(=O)NC2(C#Cc3ccc(Cl)c(Cl)c3)CC2)CC1] |
| 52 | 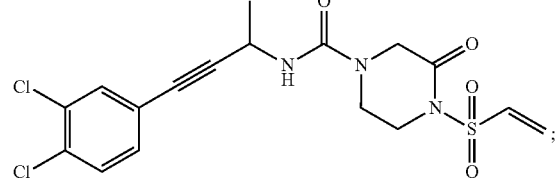 |
| 53 | 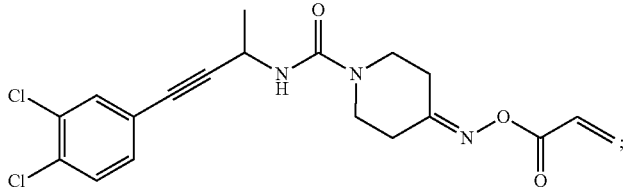 [SMILES: C=CC(=O)ON=C1CCN(C(=O)NC(C)C#Cc2ccc(Cl)c(Cl)c2)CC1] |
| 54 | 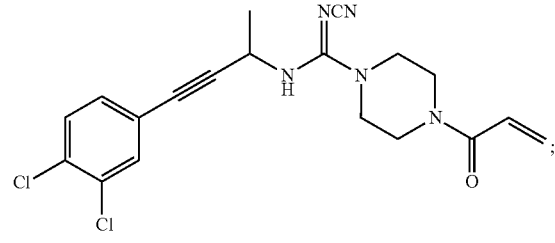 |
| 55 | 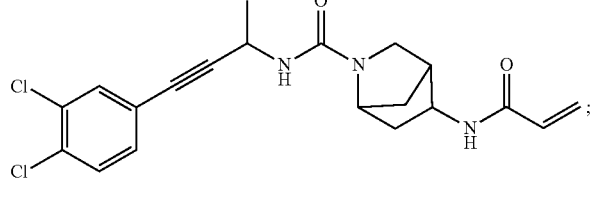 |
| 56 | 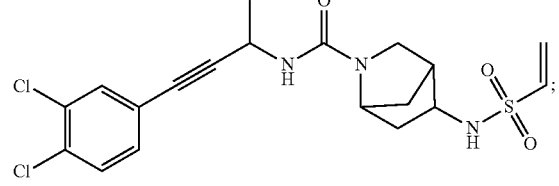 |

| Example | Structure |
|---|---|
| 57 | (structure) |
| 58 | (structure) |
| 59 | (structure) |
| 60 | (structure) |
| 61 | (structure) |
| 62 | (structure) |
| 63 | (structure) |

-continued
| Example | Structure |
|---|---|
| 64 | 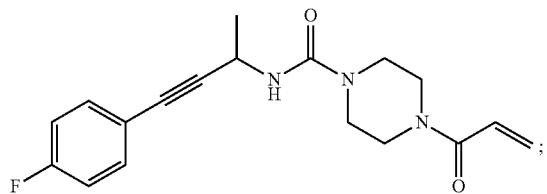 [SMILES: C=CC(=O)N1CCN(C(=O)NC(C)C#Cc2ccc(F)cc2)CC1] |
| 65 | 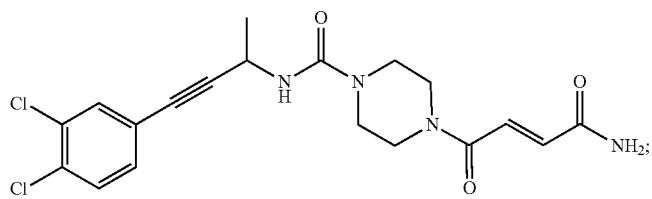 [SMILES: CC(C#Cc1ccc(Cl)c(Cl)c1)NC(=O)N1CCN(C(=O)/C=C/C(N)=O)CC1] |
| 66 | 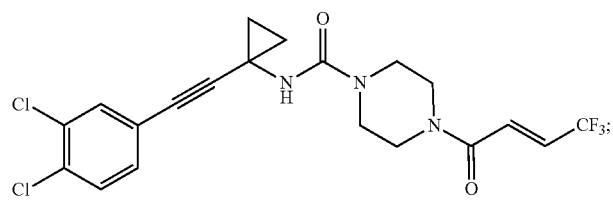 [SMILES: O=C(/C=C/C(F)(F)F)N1CCN(C(=O)NC2(C#Cc3ccc(Cl)c(Cl)c3)CC2)CC1] |
| 67 | 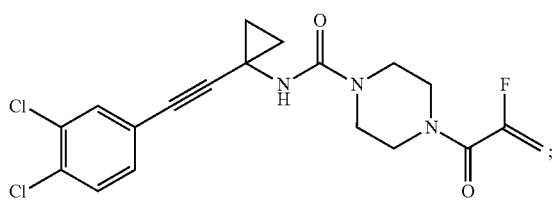 [SMILES: C=C(F)C(=O)N1CCN(C(=O)NC2(C#Cc3ccc(Cl)c(Cl)c3)CC2)CC1] |
| 68 | 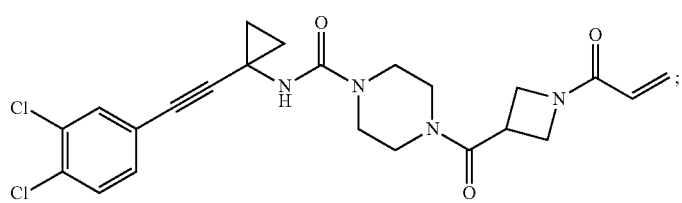 [SMILES: C=CC(=O)N1CC(C(=O)N2CCN(C(=O)NC3(C#Cc4ccc(Cl)c(Cl)c4)CC3)CC2)C1] |
| 69 | 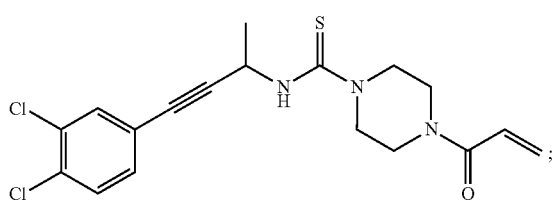 [SMILES: C=CC(=O)N1CCN(C(=S)NC(C)C#Cc2ccc(Cl)c(Cl)c2)CC1] |
| 70 | 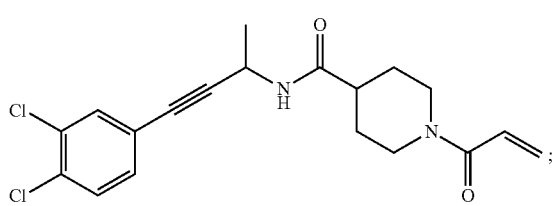 [SMILES: C=CC(=O)N1CCC(C(=O)NC(C)C#Cc2ccc(Cl)c(Cl)c2)CC1] |

-continued
| Example | Structure |
|---|---|
| 71 | 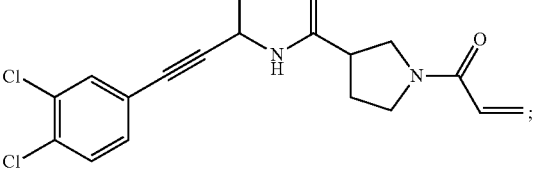<br>Isomer-1 |
| 72 | 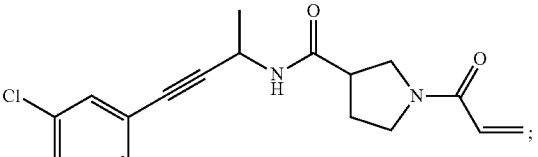<br>Isomer-2 |
| 73 | 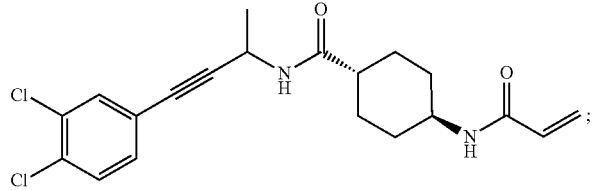 [SMILES: C=CC(=O)N[C@H]1CC[C@H](C(=O)NC(C)C#Cc2ccc(Cl)c(Cl)c2)CC1] |
| 74 | 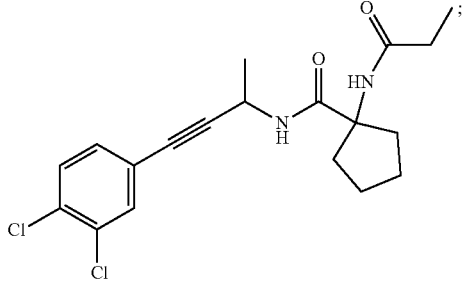 [SMILES: CCC(=O)NC1(C(=O)NC(C)C#Cc2ccc(Cl)c(Cl)c2)CCCC1] |
| 75 | 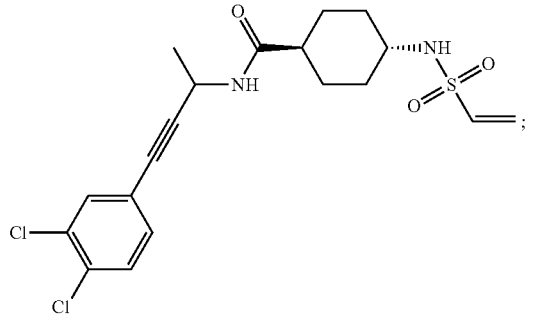 [SMILES: C=CS(=O)(=O)N[C@H]1CC[C@H](C(=O)NC(C)C#Cc2ccc(Cl)c(Cl)c2)CC1] |
| 76 | 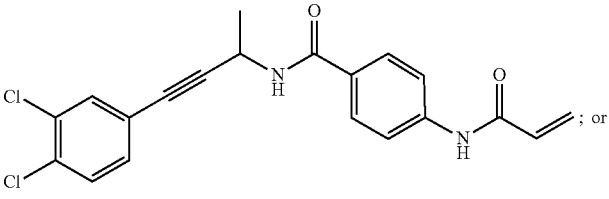 [SMILES: C=CC(=O)Nc1ccc(C(=O)NC(C)C#Cc2ccc(Cl)c(Cl)c2)cc1] |

| Example | Structure |
|---|---|
| 77 | 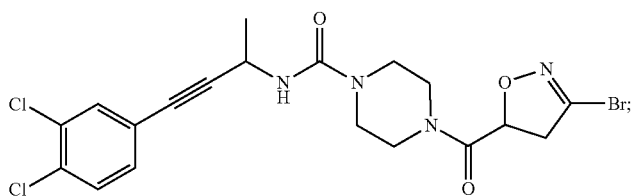 [SMILES: CC(C#Cc1ccc(Cl)c(Cl)c1)NC(=O)N1CCN(C(=O)C2CC(Br)=NO2)CC1] |

In a certain embodiments, the present invention relates to a pharmaceutical composition, comprising at least one compound of formula (I), or a pharmaceutically acceptable salt or a stereoisomer thereof, and a pharmaceutically acceptable carrier or excipient.

In a certain embodiments, the present invention relates to a compound or a pharmaceutically acceptable salt or a stereoisomer thereof, for use as a medicament.

In a certain embodiments, the pharmaceutical composition according to compound of formula (I), further comprising at least one agent selected from an anticancer agent, a chemotherapy agent, and an antiproliferative compound.

In certain embodiments, the compounds of the present invention are expected to be useful in the therapy of proliferative diseases such as cancers, including but not limited to carcinoma, including that of the breast, liver, lung, colon, kidney, bladder, including small cell lung cancer, non-small cell lung cancer, head and neck, thyroid, esophagus, stomach, pancreas, ovary, gall bladder, cervix, prostate and skin, including squamous cell carcinoma.

In certain embodiments, the compounds of the present invention can be administered in the form of a pharmaceutical composition to a patient in need of treatment of a haematological malignancies which include but not limited to leukemias and lymphomas which include but not limited to hematopoietic tumors of lymphoid lineage, acute lymphoblastic leukemia, acute lymphocytic leukemia, small lymphocytic lymphoma, Hodgkins lymphoma, non-Hodgkins lymphoma, B-cell lymphoma, T-cell lymphoma, hairy cell lymphoma, myeloma, mantle cell lymphoma, and Burkett's lymphoma, hematopoietic tumors of myeloid lineage, including acute and chronic myelogenous leukemias, myelodysplastic syndrome and promyelocytic leukemia.

In certain embodiments, the pharmaceutical composition is useful for treating a patient with a proliferative disease. In certain embodiments, the pharmaceutical composition is useful for treating a patient with cancer. In certain embodiments, the pharmaceutical composition is useful for treating a patient with a lymphoma. In certain embodiments, the pharmaceutical composition is useful for treating a patient with Hodgkin's lymphoma, Burkitt's lymphoma, non-Hodgkin's lymphoma, diffuse large B-cell lymphoma, or MALT lymphoma. In certain embodiments, the pharmaceutical composition is useful for treating a patient with diffuse large B-cell lymphoma.

Pharmaceutical Compositions

In certain embodiments, present invention provides a pharmaceutical composition comprising the compound of formula (I) and a pharmaceutically acceptable salt or a stereoisomer thereof, and a pharmaceutically acceptable carrier or excipient.

In certain embodiments, the pharmaceutical composition of the invention further comprises at least one agent selected from an anticancer agent, a chemotherapy agent, and an antiproliferative compound.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers or finely divided solid carriers or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

In certain embodiments, present invention provides a combination comprising the compound of formula (I) and pharmaceutically acceptable salt or a stereoisomer thereof, and one or more therapeutically active co-agents.

In certain embodiments, the present invention provides use of the compounds as disclosed in the present invention for the preparation of a medicament for the treatment of cancer.

Methods of Treatment

In certain embodiments, the present invention provides compounds for use as a medicament.

In certain embodiments, the invention provides the use of the compounds of the present invention in the manufacturing of medicament.

In certain embodiments, the invention provides the a method of treating cancer or proliferative disorder, comprising administration of a therapeutically effective amount of a formula (I) or a pharmaceutically acceptable salt or a stereoisomer thereof In certain embodiments, the present invention provides methods for inhibiting growth of tumour cells and/or metastasis by administering a therapeutically effective amount of compound of formula (I) or a pharmaceutically acceptable salt or a stereoisomer thereof.

In certain embodiments, the present invention provides methods for treating cancer or proliferative disorder, by administering a therapeutically effective amount of compound of formula (I) or a pharmaceutically acceptable salt or a stereoisomer thereof.

In certain embodiments, the cancer or proliferative disorder is selected from solid tumor, benign or malignant tumor, carcinoma of the brain, kidney, liver, stomach, vagina, ovaries, gastric tumors, breast, bladder colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, papillary carcinoma, seminoma, melanoma; hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulnemia (WM), splenic marginal zone lymphoma, intravascular large B-cell lymphoma, plasmacytoma and multiple myeloma.

In certain embodiments, the cancer or proliferative disorder is selected from lymphoma, leukemia, breast cancer, lung cancer (non-small cell lung cancer), colon cancer, colorectal cancer, brain cancer (glioma, medulloblastoma and ependymoma), familial adenomatous polyposis (FAP), and Barrett's esophagus.

In certain embodiments, the invention provides the compounds of formula (I), pharmaceutically acceptable salt or a stereoisomer thereof, for use in the treatment of a cancer, an inflammatory disorder, an autoimmune disease, chronic graft versus host disease, metabolic disorder, a hereditary disorder, a hormone-related disease, immunodeficiency disorders, a condition associated with cell death, a destructive bone disorder, thrombin-induced platelet aggregation, liver disease or cardiovascular disorder.

In certain embodiments, the invention provides the compounds of formula (I), pharmaceutically acceptable salt or a stereoisomer thereof, for use in the management of cytokine release syndrome associated with T cell-engaging therapies including CAR-T therapy.

In certain embodiments, the use of compound of a formula (I) or a pharmaceutically acceptable salt or a stereoisomer thereof in the manufacture of a medicament for the treatment of cancer, an inflammatory disorder, an autoimmune disease, chronic graft versus host disease, metabolic disorder, a hereditary disorder, a hormone-related disease, immunodeficiency disorders, a condition associated with cell death, a destructive bone disorder, thrombin-induced platelet aggregation, liver disease or cardiovascular disorder.

In certain embodiments, the invention provides a method of managing a cytokine release syndrome associated with T cell-engaging therapies including CAR-T therapy comprising administration of therapeutically effective amount of compound of formula (I).

In certain embodiments, the invention provides the use of the compounds of the present invention in the manufacturing of medicament for the treatment and prevention of a proliferative disease. In certain embodiments, the proliferative disease is cancer. In certain embodiments, the proliferative disease is benign neoplasm, a disease associated with angiogenesis, an inflammatory disease, an autoinflammatory disease, chronic graft versus host disease, or an autoimmune disease. In certain embodiments, the cancer is a lymphoma. In certain embodiments, the cancer is leukemia. In certain embodiments, the cancer is Hodgkin's lymphoma. In certain embodiments, the cancer is non-Hodgkin's lymphoma. In certain embodiments, the cancer is Burkitt's lymphoma. In certain embodiments, the cancer is diffuse large B-cell lymphoma (DLBCL). In certain embodiments, the cancer is MALT lymphoma. In some embodiments, the cancer is germinal center B-cell-like diffuse large B-cell lymphoma (GCB-DLBCL) or primary mediastinal B-cell lymphoma (PMBL). In some embodiments, the cancer is activated B-cell-like diffuse large B-cell lymphoma (ABC-DLBCL).

In any one of the foregoing embodiments, the cancer or proliferative disorder is selected the group consisting of a solid tumor, benign or malignant tumor, carcinoma of the brain, kidney, liver, stomach, vagina, ovaries, gastric tumors, breast, bladder colon, prostate, pancreas, lung, cervix, testis, skin, bone or thyroid; sarcoma, glioblastomas, neuroblastomas, multiple myeloma, gastrointestinal cancer, a tumor of the neck and head, an epidermal hyperproliferation, psoriasis, prostate hyperplasia, a neoplasia, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, papillary carcinoma, seminoma, melanoma; hematological malignancies selected from leukemia, diffuse large B-cell lymphoma (DLBCL), activated B-cell-like DLBCL, chronic lymphocytic leukemia (CLL), chronic lymphocytic lymphoma, primary effusion lymphoma, Burkitt lymphoma/leukemia, acute lymphocytic leukemia, B-cell pro lymphocytic leukemia, lymphoplasmacytic lymphoma, Waldenstrom's macroglobulnemia (WM), splenic marginal zone lymphoma, intravascular large B-cell lymphoma, plasmacytoma and multiple myeloma.

In certain embodiments, the present invention provides the use of the compounds of this invention to modulate pathways impacting cancer, inflammatory disorders and autoimmune diseases.

In certain embodiments, the pathway impacted by the compounds of this invention includes growth-promoting pathways origniating from cell surface receptors.

In certain embodiments, the growth-promoting pathway impacted by the compounds of this invention includes epidermal growth factor receptor (EGFR) signaling.

In certain embodiments, the compounds of this invention specifically inhibit one or more components of the EGFR signaling including K-Ras, B-Raf, MEK and ERK.

In certain embodiments, the growth-promoting pathway impacted by the compounds of this invention includes B cell receptor (BCR) pathway.

In certain embodiments, the compounds of this invention inhibit one or more components of the BCR pathway including CARD11-BCL10-MALT1 (CBM) complex.

In certain embodiments, the compounds of this invention inhibit one or more components of the BCR pathway leading to inhibition of cleavage of substrates of MALT1 protease including A20 and RelB.

In certain embodiments, the compounds of this invention inhibit one or more components of the BCR pathway leading to inhibition of transcription factor NFkB.

In certain embodiments, the compounds of this invention inhibit one or more components of the BCR pathway leading to inhibition of secretion of cytokines such as IL-6 and IL-10.

In certain embodiments, the pathway impacted by the compounds of this invention includes T cell receptor (TCR) pathway.

In certain embodiments, the compounds of this invention inhibit one or more components of the TCR pathway leading to inhibition of secretion of cytokines such as IL-17 and IFN-γ.

The method(s) of treatment of the present patent application comprise administering a safe and effective amount of a compound according to formula (I) or pharmaceutically acceptable salt thereof or a stereoisomer thereof, to a patient (particularly a human) in need thereof.

In certain embodiments, the present invention provides the use of the compounds of this invention to manage cytokine release syndrome associated with T cell-engaging therapies.

In certain embodiments, the present invention provides the use of the compounds of this invention to manage cytokine release syndrome associated with therapy with T cells expressing chimeric antigen receptor (CAR-T).

In certain embodiments, the compound of formula (I) can be used for treatment of Cancers include: lymphoma and leukemia.

In certain embodiments, the compounds of formula (I) can be used for treatment of Cancers include: breast cancer.

In certain embodiments, the compounds of formula (I) can be used for treatment of Cancers include: lung cancer, in particular non-small cell lung cancer.

In certain embodiments, the compounds of formula (I) can be used for treatment of Cancers include: colon cancer and colorectal cancer.

In certain embodiments, the compounds of formula (I) can be used for treatment of Cancers include: brain cancer, including glioma, medulloblastoma and ependymoma.

In certain embodiments, the compounds of formula (I) can be used for treatment of Cancers include: familial adenomatous polyposis (FAP).

In certain embodiments, the compounds of formula (I) can be used for treatment of Cancers include: Barrett's esophagus.

Definitions

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an oxo, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heteroaryl, a heterocycloalkyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to saturated aliphatic groups, including but not limited to $C_1$-$C_{10}$ straight-chain alkyl groups or $C_3$-$C_{10}$ branched-chain alkyl groups. Preferably, the "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. The "alkyl" group may be optionally substituted.

As used herein, the term "heteroalkyl" refers to a straight- or branched-chain alkyl group in which one or more of carbon atoms have been replaced by a heteroatom selected from S, O, P and N; wherein the 'alkyl' group is as defined above. Exemplary 'heteroalkyl's include alkyl ethers, secondary and tertiary alkyl amines, amides, alkyl sulfides and alkyl disulfides. The group, may be a terminal group or a bridging group.

As used herein, the term "alkenyl" refers to a carbon chain which contains at least one carbon-carbon double bond, and which may be linear or branched or combinations thereof. Examples of "alkenyl" include, but are not limited to, vinyl, allyl, isopropenyl, pentenyl, hexenyl, heptenyl, 1-propenyl, 2-butenyl and 2-methyl-2-butenyl.

By analogy, the expression "alkenylene" refers to a divalent "alkenyl" radical as above defined.

As used herein, the term "alkynyl" refers to straight or branched carbon chains with one or more triple bonds wherein the number atoms is in the range 2 to 6.

By analogy, the expression "alkynylene" refers to a divalent "alkynyl" radical as above defined.

As used herein, the term "halo" or "halogen" alone or in combination with other term(s) means fluorine, chlorine, bromine or iodine.

As used herein, the term "haloalkyl" means alkyl substituted with one or more halogen atoms, wherein the halo and alkyl groups are as defined above. The term "halo" is used herein interchangeably with the term "halogen" means F, Cl, Br or I. Examples of "haloalkyl" include but are not limited to fluoromethyl, difluoromethyl, chloromethyl, trifluoromethyl and 2,2,2-trifluoroethyl.

As used herein, the term "hydroxy" or "hydroxyl" alone or in combination with other term(s) means —OH.

As used herein the term "hydroxyalkyl" or "hydroxylalkyl" means alkyl substituted with one or more hydroxyl groups, wherein the alkyl groups are as defined above.

Examples of "hydroxyalkyl" include but are not limited to, hydroxymethyl, hydroxyethyl, hydroxypropyl and propan-2-ol.

The term "ester", as used herein, refers to a group —C(O)O$R_{11}$ wherein $R_{11}$ represents a hydrocarbyl group.

The term "carboxy" or "carboxylic acid", as used herein, refers to a group represented by the formula —CO$_2$H.

The term "thioester", as used herein, refers to a group —C(O)S$R^{11}$ or —SC(O)$R^{11}$ wherein $R^{11}$ represents a hydrocarbyl.

As used herein, the term "hydrocarbyl" is a group having a carbon atom directly attached to the remaining part of the molecule having hydrocarbon character.

As used herein, the term "oxo" refers to =O group.

As used herein, the term "alkoxy" refers to the group —O-alkyl, where alkyl groups are as defined above. Exemplary $C_1$-$C_{10}$ alkoxy group include but are not limited to methoxy, ethoxy, n-propoxy, n-butoxy or t-butoxy. An alkoxy group can be optionally substituted with one or more suitable groups.

As used herein, the term "alkoxyaryl" refers to the group —O-alkyl, which is attached aryl group, where alkyl and aryl groups are as defined in this specification.

As used herein, the term "cyano" refers to —CN group.

As used herein, "amino" refers to an —NH$_2$ group.

As used herein, "amide" or "amido" refers to an —CONH$_2$ group.

As used herein, "alkylamino" or "cycloalkylamino", refer to an —NH$_2$ group, wherein nitrogen atom of said group being attached to one or two alkyl or cycloalkyl groups respectively. Representative examples of an "alkylamino" and "cycloalkylamino" groups include, but are not limited to —NHCH$_3$ and —NH-cyclopropyl. The term "alkylamino" also includes dialkylamino (e.g., —N(CH$_3$)$_2$) groups.

"Aminoalkyl" refers to an alkyl group, as defined above, wherein one or more of the alkyl group's hydrogen atom has been replaced with an amino group as defined above. Representative examples of an aminoalkyl group include, but are not limited to —CH$_2$NH$_2$, —CH$_2$CH$_2$NH$_2$, —CH(CH$_3$)NH$_2$, —CH$_2$CH(CH$_3$)NH$_2$. An aminoalkyl group can be unsubstituted or substituted with one or more suitable groups.

As used herein the term "cycloalkyl" alone or in combination with other term(s) means —$C_3$-$C_{10}$ saturated cyclic hydrocarbon ring. A cycloalkyl may be a single ring, which typically contains from 3 to 7 carbon ring atoms. Examples of single-ring cycloalkyls include but are not limited to cyclopropyl, cyclobutyl, cyclopentyl, cyclohexyl and cycloheptyl. A cycloalkyl may alternatively be polycyclic or contain more than one ring. Examples of polycyclic cycloalkyls include bridged, fused and spirocyclic carbocyclyls.

As used herein, the term "heterocycloalkyl" refers to a non-aromatic, saturated or partially saturated, monocyclic or polycyclic ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen, and sulfur. The term "heterocycloalkyl" also refers to the bridged bicyclic ring system having at least one heteroatom or heterogroup selected from O, N, S, S(O), S(O)$_2$, NH or C(O). Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocycloalkyl" includes azetidinyl, pyrrolidinyl, morpholinyl and piperidinyl. All heterocycloalkyl are optionally substituted by one or more aforesaid groups.

As used herein, the term "(heterocycloalkyl)alkyl" refers to the group alkyl, attached heterocycloalkyl group, where 'alkyl' and 'heterocycloalkyl' groups are as defined in this specification.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, pyrazolopyrimidyl, furopyridinyl, purinyl, benzothiadiazolyl, benzooxadiazolyl, benzotriazolyl, benzotriadiazolyl, carbazolyl, dibenzothienyl, acridinyl and the like. Preferably "heteroaryl" refers to 5- to 6-membered ring selected from the group consisting of furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more aforesaid groups.

As used herein, the term "aryl" is optionally substituted monocyclic, bicyclic or polycyclic aromatic hydrocarbon ring system of about 6 to 14 carbon atoms. Examples of a $C_6$-$C_{14}$ aryl group include, but are not limited to phenyl, naphthyl, biphenyl, anthryl, fluorenyl, indanyl, biphenylenyl and acenaphthyl. Aryl group can be unsubstituted or substituted with one or more suitable groups.

As used herein, the term "aryloxy" refers to the group —O-aryl, where aryl groups are as defined above. Exemplary "aryloxy" group include but are not limited to phenoxy or napthyl-oxy.

The term "acyl" refers to a group R—CO— wherein R is an optionally substituted alkyl group defined above. Examples of 'acyl' groups are, but not limited to, $CH_3CO—$, $CH_3CH_2CO—$, $CH_3CH_2CH_2CO—$ or $(CH_3)_2CHCO—$.

The term "heteroatom" as used herein designates a sulfur, nitrogen or oxygen atom. As used herein, the term 'compound(s)' comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "pharmaceutical composition" refers to a composition(s) containing a therapeutically effective amount of at least one compound of formula (I) or a pharmaceutically acceptable salt thereof; and a pharmaceutically acceptable carrier.

The pharmaceutical composition(s) usually contain(s) about 1% to 99%, for example, about 5% to 75%, or from about 10% to about 30% by weight of the compound of formula (I) or (II) or pharmaceutically acceptable salts thereof. The amount of the compound of formula (I) or pharmaceutically acceptable salts thereof in the pharmaceutical composition(s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

As used herein, the term "treat", "treating" and "treatment" refer to a method of alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" that may be interchangeable with 'patient', refers to an animal, preferably a mammal, and most preferably a human.

As used herein, the term, "therapeutically effective amount" refers to an amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a diseases or disorder, in particular their use in diseases or disorder associated with cancer. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compound of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium or zinc salts.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The present invention also provides methods for formulating the disclosed compounds as for pharmaceutical administration.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

The term "stereoisomers" refers to any enantiomers, diastereoisomers or geometrical isomers of the compounds of formula (I), wherever they are chiral or when they bear one or more double bonds. When the compounds of the formula (I) and related formulae are chiral, they can exist in racemic or in optically active enantiomeric form. It should be understood that the invention encompasses all stereochemical isomeric forms, including diastereomeric, enantiomeric and epimeric forms, as well as d-Isomers and l-Isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric Isomers. The present invention includes all cis, trans, syn, anti, entgegen (E) and zusammen (Z) Isomers as well as the appropriate mixtures thereof.

The compounds of the present invention may be used as single drug or as a pharmaceutical composition in which the compound is mixed with various pharmacologically acceptable materials.

The compounds of the invention are typically administered in the form of a pharmaceutical composition. Such compositions can be prepared using procedures well known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents and solvents.

The pharmaceutical composition can be administered by oral, parenteral or inhalation routes. Examples of the parenteral administration include administration by injection, percutaneous, transmucosal, transnasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action. Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

The pharmaceutical compositions of the present patent application may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I.

Isotopically labeled compounds of the present inventions can generally be prepared by following procedures analogous to those disclosed in the schemes and/or in the examples herein below, by substituting an isotopically labeled reagent for a non-isotopically labeled reagent.

The following abbreviations refer respectively to the definitions herein: BBr$_3$—Boron tribromide; DCM—Dichloromethane; DMA—Dimethylacetamide; DMSO—Dimethylsulfoxide; DIPEA—N,N-Diisopropylethylamine; DPPA—Diphenylphosphoryl azide; EDCl or EDC.HCl—1-Ethyl-3-(3-dimethylaminopropyl)carbodiimide hydrochloride; NaHCO$_3$—Sodium bicarbonate; EtOH—Ethanol; EtI—Ethyliodide; Dioxane.HCl;—Hydrochloric acid in dioxane; Na$_2$SO$_4$—Sodium sulphate; NaHMDS—Sodium bis(trimethylsilyl)amide; Na$_2$CO$_3$—Sodium carbonate; Na$_2$S$_2$O$_3$-sodium thiosulphate; H$_2$O—water; br—Broad; Å—Angstrom; °C.—Degree Celsius; conc—Concentrated; CHCl$_3$—Chloroform; CDCl$_3$//chloroform-d—Deuterated Chloroform; DMSO-d$_6$—Deuterated dimethylsulfoxide; CH$_2$Cl$_2$—DCM—Dichloromethane; DMF—N,N-Dimethylformamide; Et$_2$O—Diethyl ether; g—Gram; h—Hours; HOBT—Hydroxybenzotriazole; $^1$H—Proton; HCl—Hydrochloric acid; Hz—Hertz; IPA—Isopropyl alcohol; J—Coupling Constant; LC-MS—Liquid Chromatography—Mass Spectroscopy; LiCl—Lithium Chloride; LiOH—Lithium hydroxide; HATU-1-[Bis(dimethylamino)methylene]-1H-1,2,3-triazolo[4,5-b]pyridinium-3-oxide hexafluorophosphate; HPLC—High-performance liquid chromatography; chiral HPLC—chiral high-performance liquid chromatography; MeOH—methanol; M—Molar; MHz—Mega Hertz (frequency); MS—Mass Spectroscopy; mmol—Milli Mole; mL—Milli Litre; min—Minutes; mol—Moles; M$^+$—Molecular ion; m/z-mass to charge ratio; N—Normality; NMR—Nuclear Magnetic Resonance; NMM—N-methylmorpholine; Et$_3$N or TEA—Triethylamine; ppm—Parts per million; rt/RT—Room temperature; s—Singlet; d—Doublet, t—Triplet; q—Quartet; m—Multiplet; dd—doublet of doublets; td—triplet of doublets; qd—quartet of doublets; ddd—doublet of doublet of doublets; dt—doublet of triplets; ddt—doublet of doublet of triplets; p-pentet; TBTU—O-(Benzotriazol-1-yl)-N,N,N',N'-tetramethyluronium tetrafluoroborate; TLC—Thin Layer Chromatography; THF—Tetrahydrofuran;%—Percentage; μ—Micron; μL—Micro liter; μM-Micro molor; δ—Delta; anh.—anhydrous; and ±—racemic mixture.

General Modes of Preparation:

Following general guidelines apply to all experimental procedures described here. Until otherwise stated, experiments are performed under positive pressure of nitrogen, temperature describes are the external temperature (i.e. oil bath temperature). Reagents and solvents received from vendors are used as such without any further drying or purification. Molarities mentioned here for reagents in solutions are approximate as it was not verified by a prior titration with a standard. All reactions are stirred under magnetic stir bar. Cooling to minus temperature was done by acetone/dry ice or wet ice/salts. Magnesium sulfate and sodium sulfate were used as solvent drying agent after reaction work up and are interchangeable. Removing of solvents under reduced pressure or in vacuo or concentration of the reaction mixture means distilling of solvents in rotary evaporator.

Compounds of this invention may be made by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

The specifics of the process for preparing compounds of the present invention are detailed in the experimental section.

The present invention shall be illustrated by means of some examples, which are not construed to be viewed as limiting the scope of the invention.

The present invention relates to novel substituted alkynylene derivatives of formula (I) which are useful as anticancer agents and to pharmaceutical compositions may be useful in methods provided herein for the treatment or prevention of proliferative disease conditions including various types of Lymphoma cancers.

Each embodiment is provided by way of explanation of the invention, and not by way of limitation of the invention. In fact, it will be apparent to those skilled in the art that various modifications and variations can be made to the compounds, compositions and methods described herein without departing from the scope or spirit of the invention. For instance, feature illustrated or described as part of one embodiment can be applied to another embodiment to yield a still further embodiment. Thus it is intended that the present invention include such modifications and variations and their equivalents. Other objects, features, and aspects of the present invention are disclosed in, or are obvious from the following detailed description. It is to be understood by one of ordinary skill in the art that present discussion is a description of exemplary embodiments only, and is not to be constructed as limiting the broader aspects of the present invention Experimental Unless otherwise stated, work-up includes distribution of the reaction mixture between the organic and aqueous phases, separation of layers and drying the organic layer over anhydrous sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase.

Analysis for the compounds of the present invention unless mentioned, was conducted in the general methods well known to the person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

It will be apparent to those skilled in the art that many modifications, both to materials and methods, may be practiced without departing from the scope of the invention. Some of the intermediates were taken to next step based on TLC results, without further characterization, unless otherwise specified.

The MS (Mass Spectral) data provided in the examples were obtained using the equipment(s)-API 2000 LC/MS/MS/Triplequad; Agilent Technologies/LC/MS/DVL/Singlequad; Shimadzu LCMS-2020/Singlequad.

The NMR data provided in the examples were obtained using the equipment(s)—1H-NMR: Varian 400 MHz and Varian 300 MHz.

The HPLC performed for the provided examples using the equipments-AgilentTechnologies 1200 Series; AgilentTechnologies 1100 Series; Shimadzu (UFLC) Prominence; Shimadzu Nexera-UHPLC.

Compound purifications were performed on Combi-Flash® unless otherwise mentioned.

Intermediate-1: Aryl Halides

The following compounds are typically commercially available or may be made by techniques well-known to those skilled in the art. The products were used for the preparation of compounds of present invention and/or intermediates thereof.

| Intermediate | Structure | IUPAC |
|---|---|---|
| 1a | (Cl, Cl, I substituted benzene) | 1,2-dichloro-4-iodobenzene |
| 1b | (Cl, F, I substituted benzene) | 2-chloro-1-fluoro-4-iodobenzene |
| 1c | (Cl, CF$_3$, I substituted benzene) | 2-chloro-4-iodo-1-(trifluoromethyl)benzene |
| 1d | (Cl, CH$_3$, I substituted benzene) | 2-chloro-4-iodo-1-methylbenzene |
| 1e | (Cl, F, Br substituted benzene) | 4-bromo-2-chloro-1-fluorobenzene |
| 1f | (Cl, I substituted thiophene) | 2-chloro-5-iodothiophene |
| 1g | (Cl, OBn, Br substituted benzene) | 1-(benzyloxy)-4-bromo-2-chlorobenzene |

-continued

| Intermediate | Structure | IUPAC |
|---|---|---|
| 1h | 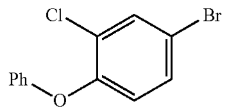 | 4-bromo-2-chloro-1-phenoxybenzene |
| 1i | 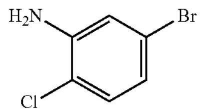 | 5-bromo-2-chloroaniline |
| 1j | 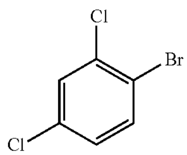 | 1-bromo-2,4-dichlorobenzene |
| 1k | 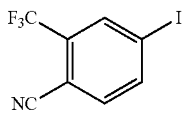 [SMILES: N#Cc1ccc(I)cc1C(F)(F)F] | 4-iodo-2-(trifluoromethyl)benzonitrile |
| 1l | 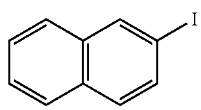 [SMILES: Ic1ccc2ccccc2c1] | 2-iodonaphthalene |
| 1m | 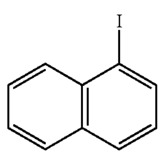 [SMILES: Ic1cccc2ccccc12] | 1-iodonaphthalene |
| 1n | 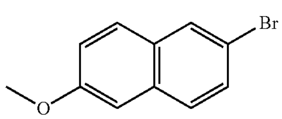 | 2-bromo-6-methoxynaphthalene |
| 1o | 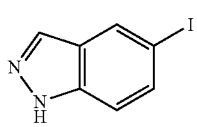 | 5-iodo-1H-indazole |
| 1p | 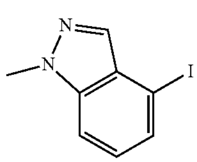 | 4-iodo-1-methyl-1H-indazole |
| 1q | 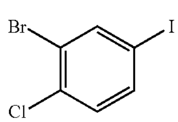 | 2-bromo-1-chloro-4-iodobenzene |

Intermediate-1r:
4-bromo-1-chloro-2-(1-methylcyclopropyl)benzene

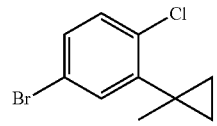

Step-1: 5-bromo-2-chloro-N-methoxy-N-methylbenzamide

To a stirred solution of 5-bromo-2-chlorobenzoic acid (11.0 g, 46.72 mmol) in DMF (75 mL) was added N,O-dimethylhydroxylamine hydrochloride (5.46 g, 56.07 mmol), HATU (26.6 g, 84.10 mmol) and DIPEA (18.1 g, 140.16 mmol) at RT and stirred for 16 h at RT. After completion of reaction, it was poured into ice water; the solid obtained was filtered and purified by Combiflash® silica gel column (hexanes/EtOAc=90/10) to obtain the title compound (11.0 g, 82%). LCMS: m/z=277.5 [M]+.

Step-2: 1-(5-bromo-2-chlorophenyl)ethan-1-one

To a stirred solution of 5-bromo-2-chloro-N-methoxy-N-methylbenzamide (Step-1) (11.0 g, 39.49 mmol) in THF (100 mL) was added methyl magnesium bromide (3.0M in THF) (19.7 mL, 59.24 mmol) at 0° C. under inert atmosphere and stirred for 16 h at RT. After completion of reaction, it was quenched by 1N HCl and extracted with diethyl ether. The ether layer was dried and concentrated and purified by Combiflash® silica gel column (hexanes/EtOAc=95/5) to obtain the title compound (7.0 g, 76.0%). LCMS: m/z=Not ionized. The product obtained was taken to the next step without purification.

Step-3: 4-bromo-1-chloro-2-(prop-1-en-2-yl)benzene

To a stirred suspension of Methyltriphenylphosphonium bromide (26.8 g, 75.10 mmol) in THF (50 mL) was added n-butyl lithium (2.0M in hexane) (37.5 mL, 75.10 mmol) at 0° C. The reaction mixture was stirred for 5 min at 0° C. and 1-(5-bromo-2-chlorophenyl)ethan-1-one (Step-2) (7.0 g, 30.04 mmol) in THF (50 mL) was added at 0° C. and stirred for 16 h at RT. After completion of reaction, it was quenched by 1N HCl and extracted with diethyl ether. The ether layer was dried and concentrated to obtain the crude compound. The crude compound was purified by Combiflash® silica gel column (hexanes/EtOAc=95/5) to get the title compound (5.0 g, 71.42%). This compound was taken for further step without purification.

Step-4: 4-bromo-1-chloro-2-(1-methylcyclopropyl)benzene

To a stirred solution of diethyl zinc (1.0M in hexane) (43.2 mL, 43.2 mmol) in DCM (25 mL) was added slowly to the solution of TFA (4.9 g, 43.2 mmol) in DCM (15 mL) at 0° C. and stirred for 20 min at 0° C. A solution of diiodomethane (11.5 g, 43.2 mmol) in DCM (30 mL) was added at 0° C. to the reaction mixture and stirred for 20 min at 0° C. A solution of 4-bromo-1-chloro-2-(prop-1-en-2-yl)benzene (Step-3) (2.0 g, 8.65 mmol) in DCM (30 mL) was added to the reaction mixture at RT and stirred for 16 h at RT. Then the reaction mixture was diluted with pentane and washed with 1N HCl, saturated NaHCO₃ solution and brine. The organic layer was dried and concentrated to get the title compound (2.0 g, 94.3%). LCMS: m/z=Not ionized.

Intermediate-1s:
4-bromo-2-chloro-N,N-diethylaniline

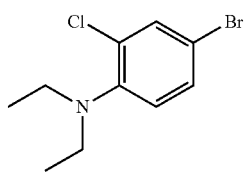

To a stirred solution of 4-bromo-2-chloroaniline (1.8 g, 8.82 mmol) in dry THF (20 mL) was added NaHMDS (11.5 mL 69.68 mmol) followed by EtI (0.9 ml, 2.95 mmol) at RT. The reaction mixture was stirred at RT for 1 h. The reaction mixture was quenched with aqueous NH₄Cl solution and extracted with EtOAc (2×50 mL), dried over Na₂SO₄ and concentrated under reduced pressure to afford the title compound (1.5 g, 75%), LCMS: m/z=264.0[M+2]⁺.

Intermediate-1t:
5-bromo-2-chloro-N,N-diethylaniline

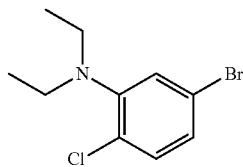

The title compound was prepared as per the procedure described for the preparation of Intermediate-1s. Yield: 76%; LCMS: m/z=262.2 [M+H]⁺.

Intermediate-1u: 1-chloro-4-iodo-5-methoxy-2-(1-methylcyclopropyl)benzene

Step-1: 4-chloro-2-methoxy-5-(1-methylcyclopropyl)aniline

The title intermediate was synthesized as per reported procedure in patent US20140288045 A1 and used for next step.

Step-2: 1-chloro-4-iodo-5-methoxy-2-(1-methylcyclopropyl)benzene

To a stirred solution of 4-chloro-2-methoxy-5-(1-methylcyclopropyl)aniline (0.8 g, 3.97 mmol) in con. HCl (3.8 mL), water (3.8 mL) added a solution of NaNO2 (0.3 g, 4.53 mmol) in water at −5° C. After stirred for 15 min added a solution of Potassium Iodide (1.2 g, 7.55 mmol). The reaction mixture was stirred at RT for 30 min. The reaction mixture was extracted with EtOAc (2×50 mL), dried over Na₂SO₄ and concentrated and purified by Combiflash® silica gel column (hexanes/ethylacetate=95/5) to afford the title compound (0.8 g, 74%), LCMS: m/z=264.0[M+2]⁺.

Intermediate-1v: 1-chloro-4-iodo-2-methoxy-5-(1-methylcyclopropyl)benzene

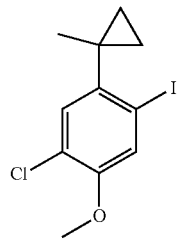

The above intermediate was prepared essentially by the method described in US2014/288045A1 and step-2 in preparation of intermediate-1u with appropriate variations in reactants, quantities of reagents, solvents and reaction conditions. Yield=59%; LCMS: No Ionization. Proceeded for next step.

The following compounds are typically commercially available or may be made by techniques well-known to those skilled in the art. The products were used for the preparation of compounds of present invention and/or intermediates thereof.

| Intermediate | Structure | IUPAC |
| --- | --- | --- |
| 2a | 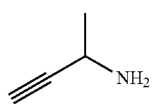 | but-3-yn-2-amine (±) |
| 2b | 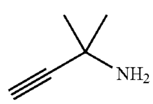 | 2-methylbut-3-yn-2-amine |
| 2c | 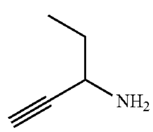 | pent-1-yn-3-amine (±) |
| 2d | 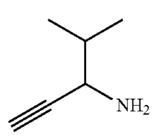 | 4-methylpent-1-yn-3-amine (±) |

The following compounds are typically commercially available or may be made by techniques well-known to those skilled in the art. The products were used for the preparation of compounds of present invention and/or intermediates thereof.

| Intermediate | Structure | IUPAC |
| --- | --- | --- |
| 3a | 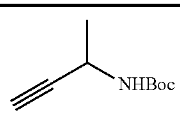 | tert-butyl but-3-yn-2-ylcarbamate (±) |
| 3b | 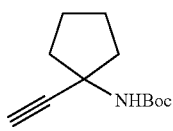 | tert-butyl (1-ethynylcyclopropyl)carbamate |

Intermediate-3c: tert-Butyl (1-ethynylcyclopentyl)carbamate

Step-1: 1-((tert-butoxycarbonyl) amino) cyclopentane-1-carboxylic acid

To a stirred suspension of 1-aminocyclopentane-1-carboxylic acid (1.00 g, 7.742 mmol) in 1,4 dioxane (10.0 mL) were added 1N NaOH solution in water (26.0 mL) and di-tert-butyl dicarbonate (1.40 mL, 6.101 mmol) at RT and it was stirred for 14 h. The reaction mixture was poured into ice water and extracted with DCM. The combined DCM layers were washed with water and brine; dried over sodium sulphate; evaporated under reduced pressure to afford the title compound (1.201 g crude). LCMS: m/z=230.3[M+H]$^{+}$.

Step 2: 1-((tert-butoxycarbonyl)amino)cyclopentane-1-carboxylic (isobutyl carbonic) anhydride To a stirred suspension of 1-((tert-butoxycarbonyl)amino) cyclopentane-1-carboxylic acid (1.20 g, 5.234 mmol) in dimethoxy ethane (30.0 mL) were added 4-methylmorpholine (0.58 mL, 5.286 mmol), isobutyl chloroformate (0.68 mL, 5.286 mmol) at −15° C. and it was stirred for 1 h. The reaction mixture was allowed to warm to RT and it was stirred for another 1 h and the reaction mixture was evaporated under reduced pressure to afford the title compound (1.782 g crude). The obtained crude was carried for the next step without further purification.

Step-3: tert-butyl (1-(hydroxymethyl) cyclopentyl) carbamate

To a stirred suspension of 1-((tert-butoxycarbonyl) amino) cyclopentane-1-carboxylic (isobutyl carbonic) anhydride (1.780 g, 5.404 mmol) in dimethoxy ethane (20.0 mL) was added sodium borohydride (0.78 g, 27.019 mmol) in water (3.0 mL) at −5° C. dropwise and it was stirred at RT for 1 h. The reaction mixture was poured into ice water extracted with ethyl acetate. The combined ethyl acetate layers were washed with water, brine; dried over sodium sulphate, evaporated under reduced pressure to afford the title compound (0.903 g, 77.84%). The compound obtained above was carried for the next step without further analysis.

Step-4: tert-butyl (1-formylcyclopentyl)carbamate

To a stirred suspension of tert-butyl (1-(hydroxymethyl) cyclopentyl) carbamate (0.980 g, 4.552 mmol) in dichloromethane (25.0 mL) was added Dess-Martin periodinane (2.51 g, 5.918 mmol) at 0° C. portion wise and it was stirred at RT for 2 h. The reaction mixture was poured in to hexane; filtered through Celite® and it was washed with DCM. The collected filtrate was dried over sodium sulphate and evaporated under reduced pressure.

The obtained residue was purified by Combiflash® on silica gel (hexanes/ethyl acetate=90/10) to afford the title compound (0.540 g, 55.67%). The compound obtained above was carried for the next step without further analysis.

Step-5: tert-butyl (1-ethynylcyclopentyl) carbamate

To a stirred suspension of 4-acetamidobenzenesulfonyl azide (0.732 g, 3.047 mmol) in acetonitrile (30.0 mL) were added dimethyl (2-oxopropyl) phosphonate (0.466 g, 2.813 mmol) at 0° C. and it was stirred at RT for 2 h. tert-butyl (1-formylcyclopentyl) carbamate (0.980 g, 4.552 mmol) in methanol (30.0 mL) was added dropwise to reaction mixture at RT and it was stirred for 2 h. The reaction mixture was filtered through Celite® pad. The collected filtrate was evaporated under reduced pressure. The obtained residue was purified by Combiflash® on silica gel (hexanes/ethyl acetate=95/05) to afford the title compound (0.300 g, 61.22%). LCMS: not ionized. The obtained product was used for further without purification.

The following compounds are typically commercially available or may be made by techniques well-known to those skilled in the art. The products were used for the preparation of compounds of present invention and/or intermediates thereof.

| Intermediate | Structure | IUPAC |
|---|---|---|
| 4a | 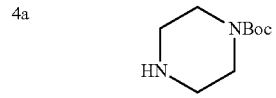 | tert-butyl piperazine-1-carboxylate |
| 4b | 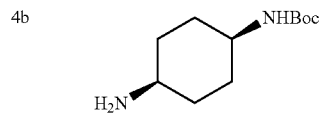 | Cis-tert-butyl ((1s,4s)-4-aminocyclohexyl) carbamate (±). |
| 4c | 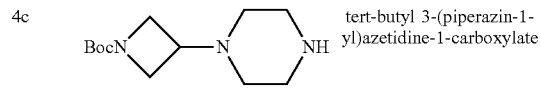 | tert-butyl 3-(piperazin-1-yl)azetidine-1-carboxylate |
| 4d | (piperazinone structure) | Piperazin-2-one |
| 4e | (diamine structure) | (1R,2R)-N1,N2-dimethylcyclohexane-1,2-diamine |
| 4f | 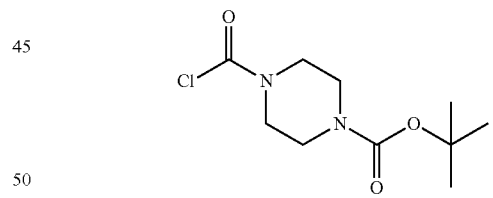 | 1-(2,2,2-trifluoroacetyl)-1$\lambda^4$-piperidin-4-one |

Intermediate-5: tert-Butyl 4-(chlorocarbonyl) piperazine-1-carboxylate

A solution of tert-butyl piperazine-1-carboxylate (10.0 g, 53.76 mmol) in DCM (50 mL) was treated with pyridine (6.37 g, 80.64 mmol) and triphosgene (7.97 g, 26.88 mmol, dissolved in 50 mL DCM) at 0° C. The resulting yellow solution was stirred at RT for 1 h. The reaction mixture was partioned between DCM and 1NHCl (150 ml); DCM layer was dried and concentrated to obtain the title compound (11.8 g, 89%). This compound was taken for next step without purification.

The following intermediates were prepared essentially by the method described in Bioorganic & Medicinal Chemistry Letters, 2000, Vol. 10, No. 20, pp. 2357-2360 with appropriate variations in reactants, quantities of reagents, solvents and reaction conditions.

| Intermediate | Structure | IUPAC |
|---|---|---|
| 5a | (structure) | tert-butyl (1-(chlorocarbonyl) piperidin-4-yl)carbamate |
| 5b | (structure) | tert-butyl 3-(4-(chlorocarbonyl) piperazin-1-yl)azetidine-1-carboxylate |

The following compounds are typically commercially available or may be made by techniques well-known to those skilled in the art. The products were used for the preparation of compounds of present invention and/or intermediates thereof.

| Intermediate | Structure | |
|---|---|---|
| 6a | (structure) | 1-(piperazin-1-yl) prop-2-en-1-one |
| 6b | (structure) | Ethyl (E)-4-oxo-4-(4-(2,2,2-trifluoroacetyl)-4$\lambda^4$-piperazin-1-yl)but-2-enoate |
| 6c | (structure) | 4-(1H-imidazol-1-yl) piperidin-1-ium 2,2,2-trifluoroacetate |
| 6d | (structure) | 1-(1-(2,2,2-trifluoroacetyl)-1l4-piperidin-4-yl)-1H-pyrrole-2,5-dione |

Intermediate-6e: N-(2-(2, 2,2-trifluoroacetyl)-2-azabicyclo [2.2.1] heptan-5-yl) acrylamide (±)

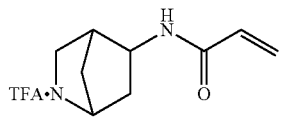

Step-1: tert-butyl 5-acrylamido-2-azabicyclo[2.2.1]heptane-2-carboxylate (±)

To a suspension of tert-butyl 5-amino-2-azabicyclo[2.2.1] heptane-2-carboxylate (±) (0.300 g, 1.41 mmol) in dichloromethane (10 mL) and triethylamine (0.580 mL, 4.23 mmol) was added acryloyl chloride (0.127 g, 1.41 mmol) at 0° C. and stirred for 1 h at room temperature. The reaction mixture was diluted with dichloromethane and washed with saturated NaHCO₃ solution, dried over anhydrous sodium sulphate and concentrated. The crude obtained was purified by CombiFlash® on silica gel (ethyl acetate=100%) to obtain the title compound (0.180 g, 48%). LCMS: m/z=167.3 [M-100]⁺

Step-2: N-(2-(2, 2,2-trifluoroacetyl)-2-azabicyclo [2.2.1] heptan-5-yl) acrylamide (±)

To a solution of tert-butyl 5-acrylamido-2-azabicyclo [2.2.1]heptane-2-carboxylate (±) (0.180 g, 0.670 mmol) in dichloromethane (5 mL), TFA (0.2 mL) was added at 0° C. and stirred at room temperature for 4 h, the reaction mixture was concentrated to obtain the title compound (0.280 g, crude). LCMS: m/z=167.1 [M-100]⁺

Intermediate-6f: N-(2-azabicyclo[2.2.1]heptan-5-yl) ethenesulfonamide (TFA salt)(±)

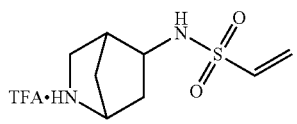

Step-1: tert-butyl 5-(vinylsulfonamido)-2-azabicyclo [2.2.1]heptane-2-carboxylate(±)

To a suspension of tert-butyl 5-amino-2-azabicyclo[2.2.1] heptane-2-carboxylate (±) (0.500 g, 2.350 mmol) and triethylamine (0.970 mL, 7.060 mmol), chloroethyl sulfonyl chloride (0.383 g, 2.35 mmol) was added at 0° C. and stirred for 1 h at room temperature. The reaction mixture was diluted with dichloromethane and washed with saturated NaHCO₃ solution, dried over anhydrous sodium sulphate and concentrated to get the crude compound which was purified by CombiFlash® (ethyl acetate=100%) to obtain the title compound (0.250 g, 358%). LCMS: m/z=203.2 [M+H-100]⁺.

Step-2 N-(2-azabicyclo[2.2.1]heptan-5-yl)ethenesulfonamide (TFA salt)(±). (±)

To a solution of tert-butyl 5-(vinylsulfonamido)-2-azabicyclo[2.2.1]heptane-2-carboxylate (±) (0.250 g, 0.827 mmol) in dichloromethane (10 mL), TFA (0.5 mL) was added at 0° C. and stirred at room temperature for 4 h. The reaction mixture was concentrated to obtain the title compound (0.300 g, crude). LCMS: m/z=203.2 [M+H-100]⁺.

Intermediate-6 g: N-allyl-N-(piperidin-4-yl)acrylamide (TFA Salt)

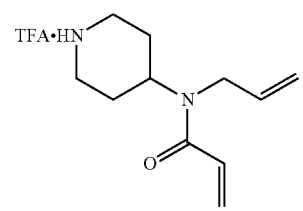

The title intermediate was synthesized as per analogues synthesis procedure described in Organic Letters, 2013, vol. 15, No. 8, p. 1986-1989.

Intermediate-6 h: (E)-3-(dimethylamino)-2-(piperazine-1-carbonyl)acrylonitrile.TFA salt

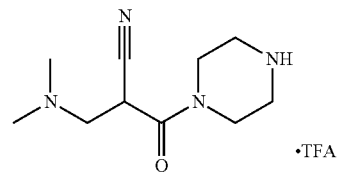

Step-1: tert-butyl 4-(2-cyanoacetyl) piperazine-1-carboxylate

To a stirred suspension of 2-cyanoacetic acid (2.85 g, 33.548 mmol) in acetonitrile (50.0 mL) were added TBTU (10.77 g, 33.548 mmol) at RT and it was stirred for 2 h. After 2 h tert-butyl piperazine-1-carboxylate (5.00 g, 26.838 mmol) was added at RT and it was further stirred for 14 h. The reaction mixture was evaporated under reduced pressure, the obtained residue was separated between water and EtOAc (1:1). The combined EtOAc layers were washed with water and brine. Dried over Na₂SO₄ and evaporated under reduced pressure. The obtained residue was purified by Combiflash® on silica gel (DCM/MeOH=99/1) to afford the title compound (2.80 g, 41.27%). LCMS: m/z=254.30[M]⁺.

Step-2: tert-butyl 4-(2-cyano-3-(dimethylamino) acryloyl) piperazine-1-carboxylate To a stirred suspension of tert-butyl 4-(2-cyanoacetyl) piperazine-1-carboxylate (1.00 g, 3.947 mmol) in DMF (10.0 mL) was added DMF-DMA (10.0 mL, 75.277 mmol) at RT and it was heated to 100° C. for 5 h. Reaction mixture was poured in to ice water, extracted with EtOAc. The combined EtOAc layers were washed with brine, water. Dried over Na₂SO₄ and evaporated under reduced pressure to afford the title compound (0.902 g crude). LCMS: m/z=309.38[M+H]⁺.

Step-3: (E)-3-(dimethylamino)-2-(piperazine-1-carbonyl)acrylonitrile.TFAsalt To a stirred suspension of tert-butyl 4-(2-cyano-3-(dimethyl amino) acryloyl) piperazine-1-carboxylate (0.20 g, 0.648 mmol) in DCM (5.0 mL) was added TFA (0.50 mL, 6.529 mmol) at RT and it was stirred for 5 h. Reaction mixture was evaporated under reduced pressure, the obtained residue was triturated with diethyl ether to afford the title compound (0.195 g crude). LCMS: m/z=209.30[M+H]$^+$.

Intermediate-6i: 3-oxo-3-(piperazin-1-yl)propanenitrile (TFA salt)

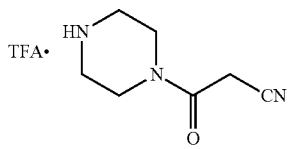

To a stirred suspension of tert-butyl 4-(2-cyanoacetyl) piperazine-1-carboxylate (0.30 g, 1.184 mmol) in DCM (5.0 mL) was added TFA (0.50 mL, 6.529 mmol) at RT and it was stirred for 14 h. The reaction mixture was evaporated under reduced pressure, the obtained residue was triturated with diethyl ether to afford the title compound (0.280 g crude). LCMS: m/z=154.19[M]$^{+1}$.

The following compounds are typically commercially available or may be made by techniques well-known to those skilled in the art. The products were used for the preparation of compounds of present invention and/or intermediates thereof.

Intermediate-8: tert-Butyl 4-(but-3-yn-2-ylcarbamoyl) piperazine-1-carboxylate (±)

To a stirred solution of but-3-yn-2-amine (±) (Intermediate 2a) (5.00 g, 72.34 mmol) in dichloromethane (100 mL), tert-butyl 4-(chlorocarbonyl) piperazine-1-carboxylate (Intermediate 5) (17.90 g, 72.34 mmol) and DIPEA (37.60 mL, 217 mmol) were added at RT. The reaction mixture, after being stirred at RT for 16 h, washed with saturated NaHCO$_3$ solution and brine. The dichloromethane layer was collected, dried and concentrated. The crude obtained was purified by Combiflash® on silica gel (hexanes/ethyl acetate=65/35) to get the title compound (8.00 g, 39.4%). LCMS: m/z=282.2 [M+H]+.

The following intermediates were prepared essentially by the method described in Intermediate-8 with appropriate variations in reactants, quantities of reagents, solvents and reaction conditions. The characterization data of the compounds are summarized herein below table.

| Intermediate | Structure | |
|---|---|---|
| 7a | 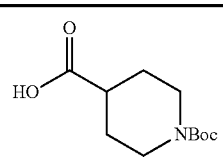 | 1-(tert-butoxycarbonyl) piperidine-4-carboxylic acid |
| 7b | 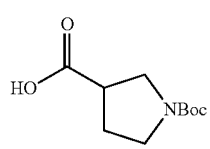 [SMILES: CC(C)(C)OC(=O)N1CCC(C(=O)O)C1] | 1-(tert-butoxycarbonyl) pyrrolidine-3-carboxylic acid |
| 7c | 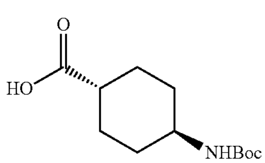 [SMILES: CC(C)(C)OC(=O)N[C@H]1CC[C@H](C(=O)O)CC1] | Trans-(1r,4r)-4-((tert-butoxycarbonyl)amino)cyclohexane-1-carboxylic acid (±) |
| 7d | 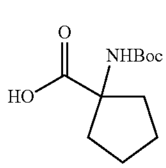 | 1-((tert-butoxycarbonyl)amino)cyclopentane-1-carboxylic acid |

| Intermediate | Structure | IUPAC | Yield (%)/ Analytical Data |
|---|---|---|---|
| 8a | 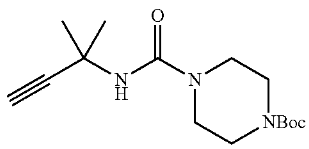 [SMILES: C#CC(C)(C)NC(=O)N1CCN(C(=O)OC(C)(C)C)CC1] | tert-butyl 4-((2-methylbut-3-yn-2-yl)carbamoyl) piperazine-1-carboxylate | Yield: 28.2% LCMS: NA |
| 8b | 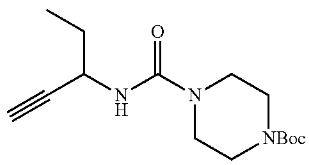 [SMILES: C#CC(CC)NC(=O)N1CCN(C(=O)OC(C)(C)C)CC1] | tert-butyl 4-(pent-1-yn-3-ylcarbamoyl) piperazine-1-carboxylate (±) | Yield: 22.8% LCMS: m/z = 240.2 [M − 56]+ |
| 8c | 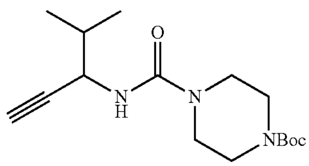 [SMILES: C#CC(NC(=O)N1CCN(C(=O)OC(C)(C)C)CC1)C(C)C] | tert-butyl 4-((4-methylpent-1-yn-3-yl)carbamoyl) piperazine-1-carboxylate (±) | Yield: 8.0% LCMS: No ionisation |
| 8d | 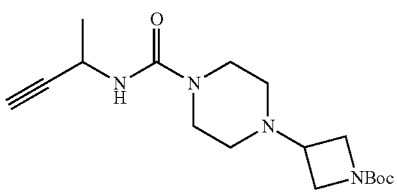 [SMILES: C#CC(C)NC(=O)N1CCN(C2CN(C(=O)OC(C)(C)C)C2)CC1] | tert-butyl 3-(4-(but-3-yn-2-ylcarbamoyl) piperazin-1-yl)azetidine-1-carboxylate (±) | Yield: 42.0% LCMS: m/z = 337.2 [M + H]+ |
| 8e | 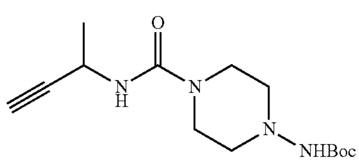 [SMILES: C#CC(C)NC(=O)N1CCN(NC(=O)OC(C)(C)C)CC1] | tert-butyl (1-(but-3-yn-2-ylcarbamoyl) piperidin-4-yl)carbamate (±) | Yield: crude LCMS: NA |
| 8f | 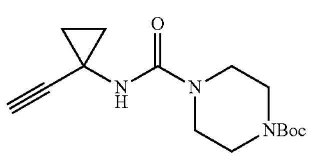 [SMILES: C#CC1(NC(=O)N2CCN(C(=O)OC(C)(C)C)CC2)CC1] | tert-butyl 4-((1-ethynylcyclopropyl)carbamoyl) piperazine-1-carboxylate | Yield: crude LCMS: NA |

Intermediate-9: tert-Butyl 4-(but-3-yn-2-ylcarbamoyl) piperidine-1-carboxylate (±)

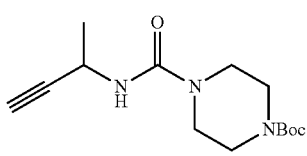 [SMILES: C#CC(C)NC(=O)N1CCN(C(=O)OC(C)(C)C)CC1]

To a stirred solution of but-3-yn-2-amine (Intermediate 2a) (0.5 g, 7.042 mmol) and 1-(tert-butoxycarbonyl) piperidine-4-carboxylic acid (Intermediate 7a) (1.61 g, 7.042) in dichloromethane (50 mL) were added diisopropylethylamine (3.73 mL, 21.126 mmol) and HATU (3.21 g, 8.450 mmol) at 0° C. After stirring 4 hour at RT, the reaction mixture was washed with saturated sodium bicarbonate solution. The dichloromethane layer was dried and concentrated. The crude compound was purified by Combiflash® column chromatography (hexanes/ethylacetate=75/25) to obtain the title compound (0.600 g, 30%). This product was taken for the next step without purification.

The following compounds were prepared essentially by the procedure described in the preparation of Intermediate-9 with appropriate variations in reactants, reagents and reaction conditions.

| Intermediate | Structure | IUPAC | Yield (%) & Analytical Data |
|---|---|---|---|
| 9a | ![structure] | tert-butyl 3-(but-3-yn-2-ylcarbamoyl) pyrrolidine-1-carboxylate (±) | Yield: 35%; LCMS: NA |
| 9b | ![structure] | tert-butyl ((1r,4r)-4-(but-3-yn-2-ylcarbamoyl)cyclohexyl) carbamate (±) | Yield: Crude LCMS: NA |

Intermediate-10: tert-butyl (1-((4-chloro-2-methoxy-5-(1-methylcyclopropyl) phenyl) ethynyl)cyclopropyl)carbamate

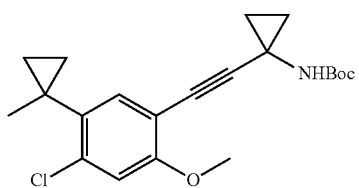 [SMILES: COc1cc(Cl)c(C2(C)CC2)cc1C#CC1(NC(=O)OC(C)(C)C)CC1]

To a solution of 1-chloro-4-iodo-5-methoxy-2-(1-methylcyclopropyl)benzene (1u) (0.600 g, 2.11 mmol), tert-butyl (1-ethynylcyclopropyl)carbamate (Intermediate 3b) (0.460 g, 2.53 mmol) and triethyl amine (0.642 mL, 6.439 mmol) in DMF (10 mL) was purged with argon gas for 20 min. Then CuI (0.79 g, 4.15 mmol) and Tetrakis(triphenylphosphine) palladium(O) (0.080 g, 0.423 mmol) were added at RT and the reaction mixture was again purged for 10 min. The reaction mixture was stirred for 2 h at 90° C. The reaction mixture was filtered through celite pad. The Collected filtrate was partitioned between Ethyl acetate and water (1:1). The EtOAc layer was dried; concentrated and purified by combiFlash® silica gel column (hexanes/EtOAc=80/20) to obtain the title compound (0.480 g, 57.61%). LCMS: m/z=276.3 [M-100]$^+$.

The following intermediates were prepared essentially by the method of Intermediate 10 with appropriate variations in reactants, reagents and reaction conditions.

| Intermediate | Structure | IUPAC | Yield (%) & Analytical Data |
|---|---|---|---|
| 10a | ![structure] | tert-butyl (1-((3,4-dichlorophenyl)ethynyl) cyclopropyl)carbamate | Yield: 62%; LCMS: m/z = 226.1 [M + H − 100]$^+$ |
| 10b | ![structure] | tert-butyl (4-(3-chloro-4-phenoxyphenyl)but-3-yn-2-yl)carbamate (±) | Yield: 50.8%; LCMS: m/z = 315.9 [M + H − 56]+. |

-continued

| Intermediate | Structure | IUPAC | Yield (%) & Analytical Data |
|---|---|---|---|
| 10c | 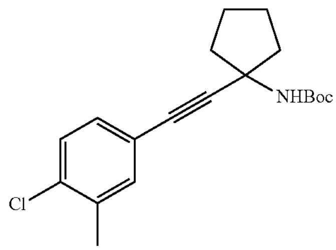 [SMILES: Cc1cc(C#CC2(NC(=O)OC(C)(C)C)CCCC2)ccc1Cl] | tert-butyl (1-((3,4-dichlorophenyl)ethynyl)cyclopentyl)carbamate | Yield: 59%; LCMS: m/z = Not ionized |
| 10d | 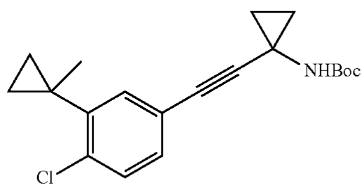 [SMILES: CC(C)(C)OC(=O)NC1(C#Cc2ccc(Cl)c(C3(C)CC3)c2)CC1] | tert-butyl (1-((4-chloro-3-(1-methylcyclopropyl)-phenyl)ethynyl)cyclopropyl)carbamate | Yield: 63%; LCMS: m/z = Not ionized |
| 10e | 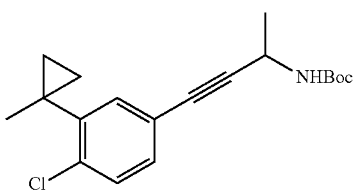 [SMILES: CC(C#Cc1ccc(Cl)c(C2(C)CC2)c1)NC(=O)OC(C)(C)C] | tert-butyl (4-(4-chloro-3-(1-methylcyclopropyl)phenyl)but-3-yn-2-yl)carbamate(±) | Yield: 81.5%; LCMS: m/z = 234.2[M + H − 100]+ |
| 10f | 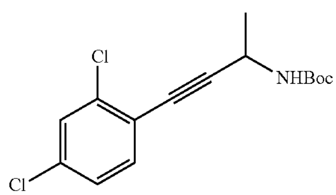 [SMILES: CC(C#Cc1ccc(Cl)cc1Cl)NC(=O)OC(C)(C)C] | tert-butyl (4-(2,4-dichlorophenyl)but-3-yn-2-yl)carbamate (±) | Yield: 27%; LCMS: m/z = NA |
| 10g | 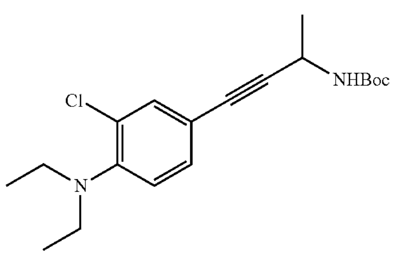 [SMILES: CCN(CC)c1ccc(C#CC(C)NC(=O)OC(C)(C)C)cc1Cl] | tert-butyl (4-(3-chloro-4-(diethylamino)phenyl)but-3-yn-2-yl)carbamate(±) | Yield: 37%; LCMS: m/z = 351.3[M + H]+. |
| 10h | 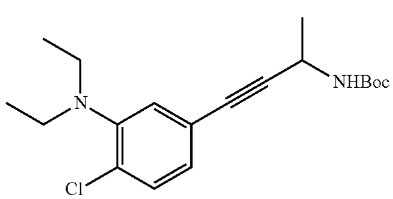 [SMILES: CCN(CC)c1cc(C#CC(C)NC(=O)OC(C)(C)C)ccc1Cl] | tert-butyl (4-(4-chloro-3-(diethylamino)phenyl)but-3-yn-2-yl)carbamate (±) | Yield: 60%; LCMS: m/z = 351.2[M + H]+. |
| 10i | 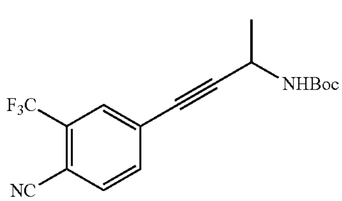 [SMILES: CC(C#Cc1ccc(C#N)c(C(F)(F)F)c1)NC(=O)OC(C)(C)C] | tert-butyl (4-(4-cyano-3-(trifluoromethyl)phenyl)but-3-yn-2-yl)carbamate(±) | Yield: 10.79% LCMS: m/z = 339.33 [M + H]+. |

-continued

| Intermediate | Structure | IUPAC | Yield (%) & Analytical Data |
|---|---|---|---|
| 10j | 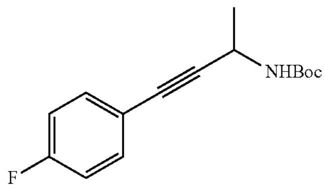 [SMILES: CC(C#Cc1ccc(F)cc1)NC(=O)OC(C)(C)C] | tert-butyl (4-(4-fluorophenyl)but-3-yn-2-yl)carbamate | Yield: 42.3% LCMS: m/z = 264.3 [M + H]+. |
| 10k | 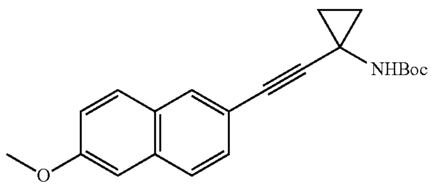 | tert-butyl (1-((6-methoxynaphthalen-2-yl)ethynyl)cyclopropyl)carbamate | Yield: crude LCMS: m/z = 236.2 [M − 100]+. |
| 10l | 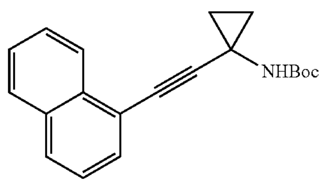 [SMILES: CC(C)(C)OC(=O)NC1(C#Cc2cccc3ccccc23)CC1] | tert-butyl (1-(naphthalen-1-ylethynyl)cyclopropyl)carbamate | Yield: 99% LCMS: m/z = 206 [M − 100]+ |
| 10m | 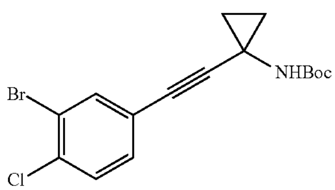 [SMILES: CC(C)(C)OC(=O)NC1(C#Cc2ccc(Cl)c(Br)c2)CC1] | tert-butyl (1-((3-bromo-4-chlorophenyl)ethynyl)cyclopropyl)carbamate | Yield: 73% LCMS: m/z = 372.3[M + 2]+ |
| 10n | 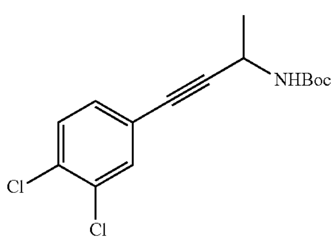 [SMILES: CC(C#Cc1ccc(Cl)c(Cl)c1)NC(=O)OC(C)(C)C] | tert-butyl (4-(3,4-dichlorophenyl)but-3-yn-2-yl)carbamate | Yield: 36.8%, LCMS: m/z = 214.2 [M − 100]+ |
| 10o | 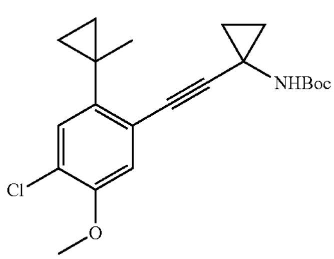 | tert-butyl (1-((4-chloro-5-methoxy-2-(1-methylcyclopropyl)phenyl)ethynyl)cyclopropyl)carbamate | Yield: 80% LCMS: m/z = 276.9 [M − 100]+ |

The Boc protected intermediates (10b, 10n and 10k) treated with dioxane.HCl for 16 h at RT. The reaction mixture was concentrated, the crude product was titurated with diethyl ether to give corresponding hydrochloride salt (11, 11a, 11b)

| Intermediate | Structure | IUPAC | Yield (%) & Analytical Data |
|---|---|---|---|
| 11 | 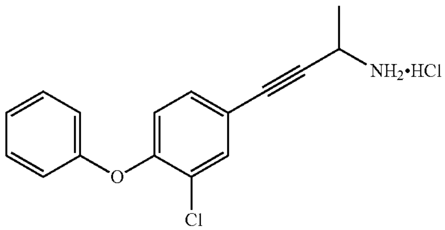 | 4-(3-chloro-4-phenoxyphenyl)but-3-yn-2-amine hydrochloride (±) | Yield: 100% LCMS: m/z = 271.9 [M + H]+. |
| 11a | 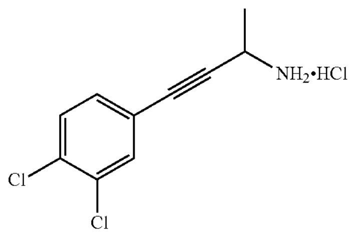 | 4-(3,4-dichlorophenyl)but-3-yn-2-amine (±) | Yield: 93% LCMS: m/z = 214.0[M]+. |
| 11b | 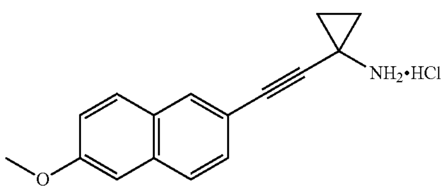 | 1-((6-methoxynaphthalen-2-yl)ethynyl)cyclopropan-1-amine hydrochloride | Crude LCMS: m/z = 236.3 [M + 1]+. (Free base) |

The Boc protected intermediates (10, 10a, 10c-10j) treated with dioxane.HCl for 16 h at RT. The reaction mixture was concentrated, the crude product was dissolved in dichloromethane and washed with aqueous bicarbonate solution to get corresponding amine free base (Intermediates 11c-11x).

| Intermediate | Structure | | Yield (%) & Analytical Data |
|---|---|---|---|
| 11c | 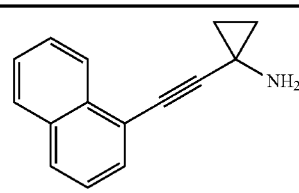 | 1-(naphthalen-1-ylethynyl)-cyclopropan-1-amine | Yield: 89%; LCMS: m/z = 208.2[M + H]+. |
| 11d | 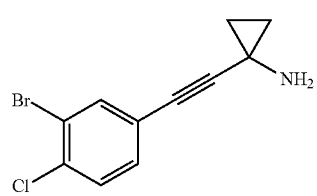 [SMILES: NC1(C#Cc2ccc(Cl)c(Br)c2)CC1] | 1-((3-bromo-4-chlorophenyl)-ethynyl)cyclopropan-1-amine | Yield: 99% LCMS: 270.2 [M + H] |
| 11e | 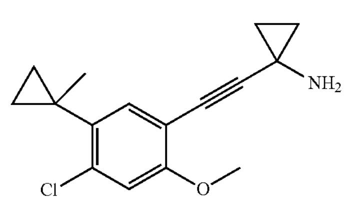 [SMILES: COc1cc(Cl)c(C2(C)CC2)cc1C#CC1(N)CC1] | 1-((4-chloro-2-methoxy-5-(1-methylcyclopropyl)phenyl)-ethynyl)cyclopropan-1-amine | Yield: 90% LCMS: 276.3 [M + H] |

-continued

| Intermediate | Structure | | Yield (%) & Analytical Data |
|---|---|---|---|
| 11o | 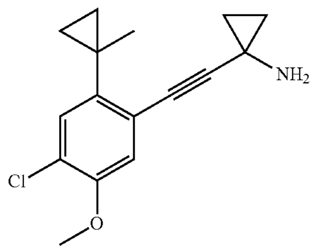 [SMILES: COc1cc(C#CC2(N)CC2)c(C2(C)CC2)cc1Cl] | 1-((4-chloro-5-methoxy-2-(1-methylcyclopropyl)phenyl)-ethynyl)cyclopropan-1-amine | Yield: 85%; LCMS: 276.3 [M + H] |
| 11p | 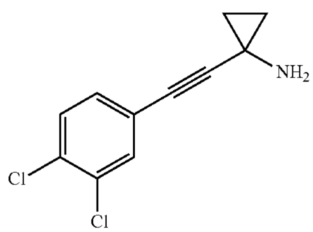 [SMILES: NC1(C#Cc2ccc(Cl)c(Cl)c2)CC1] | 1-((3,4-dichlorophenyl)-ethynyl)cyclopropan-1-amine | Yield: 92.5%; LCMS: m/z = 226.2 |
| 11q | 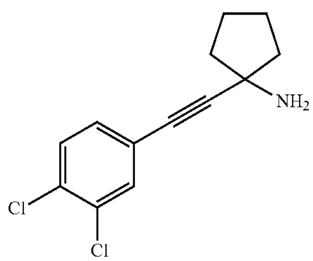 [SMILES: NC1(C#Cc2ccc(Cl)c(Cl)c2)CCCC1] | 1-((3,4-dichlorophenyl)-ethynyl)cyclopentan-1-amine | Yield: Crude; LCMS: m/z = NA |
| 11r | 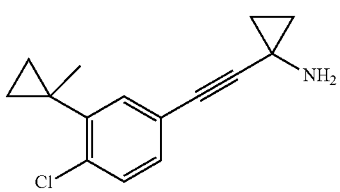 [SMILES: CC1(c2cc(C#CC3(N)CC3)ccc2Cl)CC1] | N-(1-((4-chloro-3-(1-methyl-cyclopropyl)-phenyl)ethynyl)-cyclopropyl)-12-chloranamine | Yield: 94% LCMS: m/z = 246.3 [M + H]+. |
| 11s | 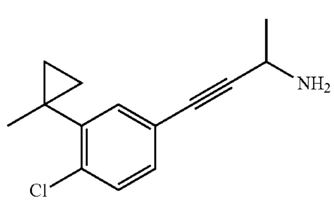 [SMILES: CC(N)C#Cc1ccc(Cl)c(C2(C)CC2)c1] | 4-(4-chloro-3-(1-methylcyclopropyl)phenyl)-but-3-yn-2-amine(±) | Yield: 92%; LCMS: m/z = not ionized |
| 11t | 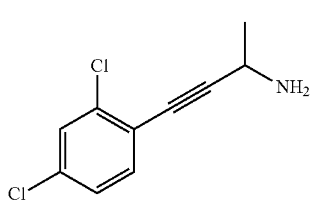 | 4-(2,4-dichlorophenyl)but-3-yn-2-amine(±) | Yield: 99%; LCMS: m/z = 214 [M]+. |

| Intermediate | Structure | | Yield (%) & Analytical Data |
|---|---|---|---|
| 11u | 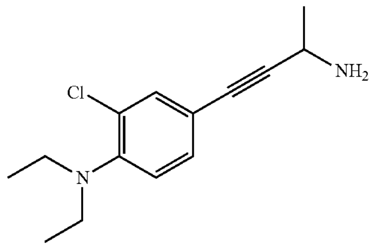 [SMILES: CCN(CC)c1ccc(C#CC(C)N)cc1Cl] | 4-(3-aminobut-1-yn-1-yl)-2-chloro-N,N-diethylaniline(±) | Yield: 83%; LCMS: m/z = 251.1 [M + H]+. |
| 11v | 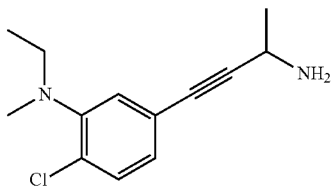 | 5-(3-aminobut-1-yn-1-yl)-2-chloro-N,N-diethylaniline(±) | Yield: 80%; LCMS: m/z = 251.2 [M + H]+. |
| 11w | 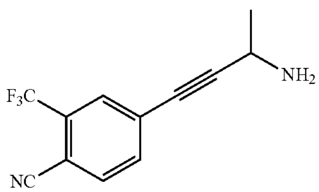 [SMILES: CC(N)C#Cc1ccc(C#N)c(C(F)(F)F)c1] | 4-(3-aminobut-1-yn-1-yl)-2-(trifluoromethyl)benzonitrile (±) | Yield:crude; LCMS: m/z = 239.21 [M + H]+. |
| 11x | 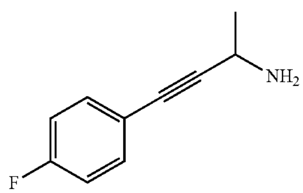 | 4-(4-fluorophenyl)but-3-yn-2-amine. | Yield:crude; LCMS: m/z = 164.2 [M]+[1]. |

Intermediate-12: Phenyl (4-(3,4-dichlorophenyl)but-3-yn-2-yl)carbamate (±)

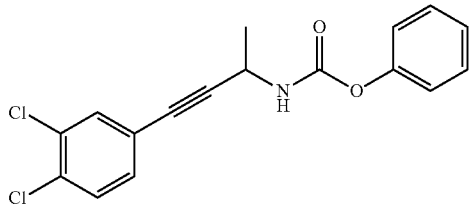 [SMILES: CC(C#Cc1ccc(Cl)c(Cl)c1)NC(=O)Oc1ccccc1]

To a stirred suspension of Intermediate 11 (1.3 g, 6.07 mmol) in THF (30 mL) was added phenyl chloroformate (1.23 g, 7.89 mmol) at 0° C. and it was stirred for 16 h at RT. The reaction mixture was diluted with ethyl acetate and washed with saturated NaHCO$_3$. The combined EtOAc layers were washed with water and brine, dried over Na$_2$SO$_4$ and evaporated under reduced pressure. The obtained residue was purified by Combiflash® on silica gel (hexanes/ethyl acetate=80/20) to afford the title compound (1.5 g, 73.9%). LCMS: m/z=214.2 [M-120]+.

The following intermediates were prepared essentially by the method of preparing Intermediate 12 with appropriate variations in reactants, reagents and reaction conditions.

| Intermediate | Structure | IUPAC | Yield (%) & Analytical Data |
|---|---|---|---|
| 12a | 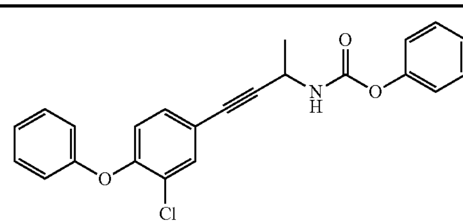 | Phenyl (4-(3-chloro-4-phenoxyphenyl)-but-3-yn-2-yl)-carbamate (±). | Yield: 71.7%; LCMS: m/z = 392.0 [M + H]+. |

-continued

| Intermediate | Structure | IUPAC | Yield (%) & Analytical Data |
|---|---|---|---|
| 12b | 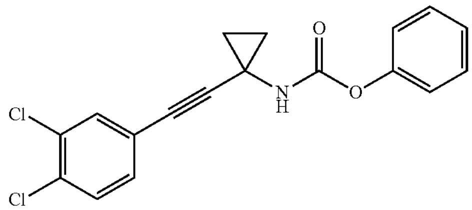 [SMILES: O=C(NC1(C#Cc2ccc(Cl)c(Cl)c2)CC1)Oc1ccccc1] | phenyl (1-((3,4-dichlorophenyl)-ethynyl)cyclopropyl)carbamate | Yield: 58% LCMS: m/z = Not ionized |
| 12c | 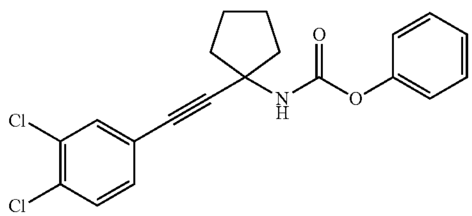 [SMILES: O=C(NC1(C#Cc2ccc(Cl)c(Cl)c2)CCCC1)Oc1ccccc1] | phenyl (1-((3,4-dichlorophenyl)-ethynyl)cyclopentyl)carbamate | Yield: 65% LCMS: m/z not ionized |
| 12d | 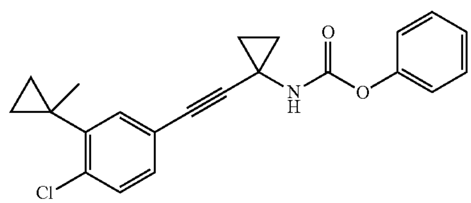 [SMILES: CC1(c2cc(C#CC3(NC(=O)Oc4ccccc4)CC3)ccc2Cl)CC1] | phenyl (1-((4-chloro-3-(1-methylcyclopropyl)phenyl)-ethynyl)cyclopropyl)carbamate | Yield: 84%; LCMS: m/z = Not ionized |
| 12e | 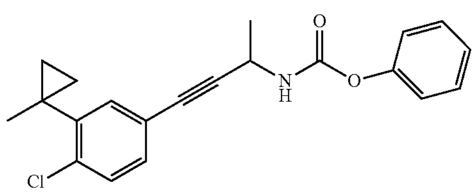 | phenyl (4-(4-chloro-3-(1-methylcyclopropyl)phenyl)-but-3-yn-2-yl)-carbamate(±). | Yield: 85%; LCMS: m/z = 234 [M + H − 120]+ |
| 12f | 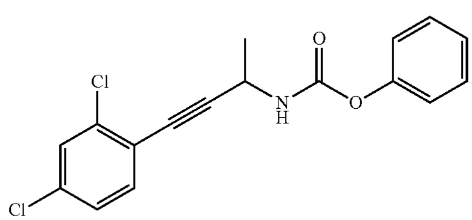 [SMILES: CC(C#Cc1ccc(Cl)cc1Cl)NC(=O)Oc1ccccc1] | phenyl (4-(2,4-dichlorophenyl)-but-3-yn-2-yl)-carbamate (±). | Yield: 60%; LCMS: m/z = NA |
| 12g | 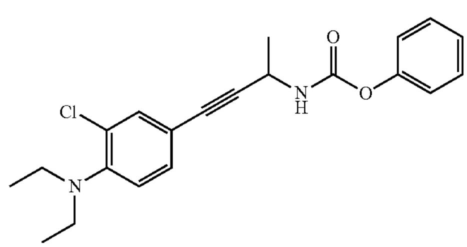 [SMILES: CCN(CC)c1ccc(C#CC(C)NC(=O)Oc2ccccc2)cc1Cl] | phenyl (4-(3-chloro-4-(diethylamino)-phenyl)but-3-yn-2-yl)-carbamate(±). | Yield: 54%; LCMS: m/z = 371.2 [M + H]+ |
| 12h | 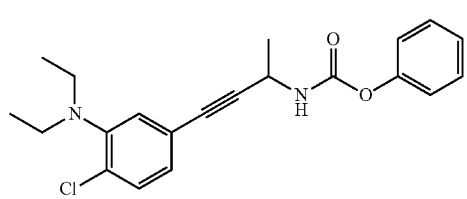 [SMILES: CCN(CC)c1cc(C#CC(C)NC(=O)Oc2ccccc2)ccc1Cl] | phenyl (4-(4-chloro-3-(diethylamino)phenyl)-but-3-yn-2-yl)-carbamate (±). | Yield: 14%; LCMS: m/z = 371.2 [M + H]+ |

-continued

| Intermediate | Structure | IUPAC | Yield (%) & Analytical Data |
|---|---|---|---|
| 12i | 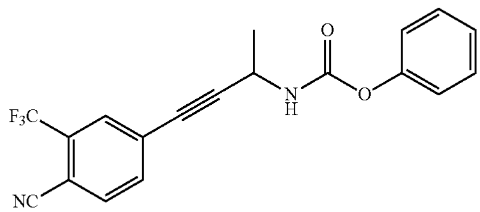 [SMILES: CC(C#Cc1ccc(C#N)c(C(F)(F)F)c1)NC(=O)Oc1ccccc1] | phenyl (4-(4-cyano-3-(trifluoromethyl)phenyl)but-3-yn-2-yl)carbamate (±). | Yield: 36.3%; LCMS: m/z = 359.32 [M + H]+ |
| 12j | 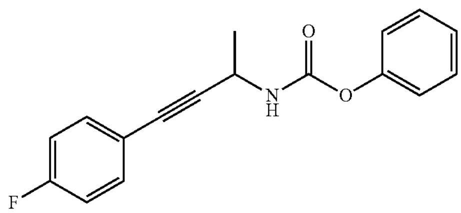 [SMILES: CC(C#Cc1ccc(F)cc1)NC(=O)Oc1ccccc1] | phenyl (4-(4-fluorophenyl)-but-3-yn-2-yl)carbamate | Yield: 32.7%; LCMS: m/z = 284.3[M + H]+. |
| 12k | 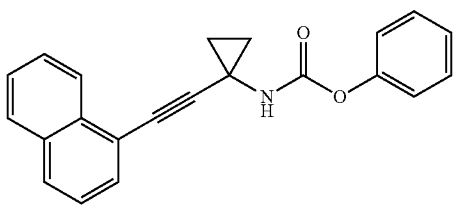 [SMILES: O=C(NC1(C#Cc2cccc3ccccc23)CC1)Oc1ccccc1] | phenyl (1-(naphthalen-1-ylethynyl)cyclopropyl)carbamate | Yield: 94%; LCMS: m/z = 208.2 [M − 120]+. |
| 12l | 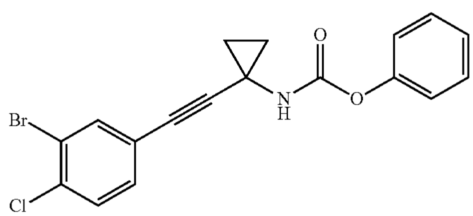 | phenyl (1-((3-bromo-4-chlorophenyl)ethynyl)cyclopropyl)carbamate | Yield: 90%; LCMS: m/z = 272.1 [M − 120]+. |
| 12m | 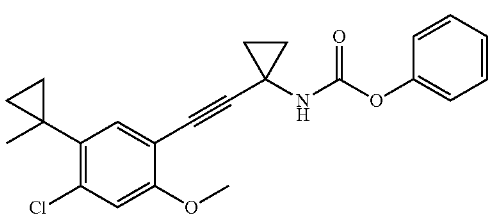 [SMILES: COc1cc(Cl)c(C2(C)CC2)cc1C#CC1(NC(=O)Oc2ccccc2)CC1] | phenyl (1-((4-chloro-2-methoxy-5-(1-methylcyclopropyl)phenyl)ethynyl)cyclopropyl)carbamate | Yield: 56%; LCMS: m/z = 396.3[M + H]+. |
| 12n | 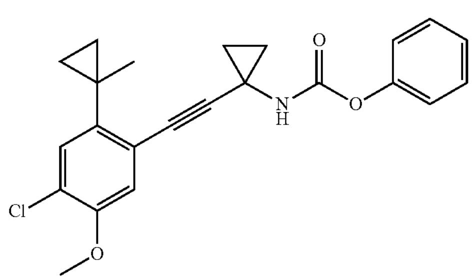 [SMILES: COc1cc(C#CC2(NC(=O)Oc3ccccc3)CC2)c(C2(C)CC2)cc1Cl] | phenyl (1-((4-chloro-5-methoxy-2-(1-methylcyclopropyl)phenyl)ethynyl)cyclopropyl)carbamate | Yield: 69%; LCMS: m/z = 396.3[M + H]+. |
| 12o | 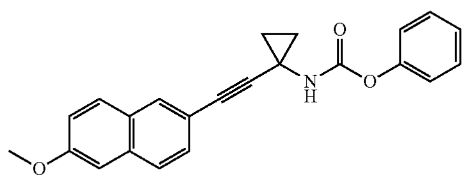 [SMILES: COc1ccc2cc(C#CC3(NC(=O)Oc4ccccc4)CC3)ccc2c1] | phenyl (1-((6-methoxynaphthalen-2-yl)ethynyl)cyclopropyl)carbamate | Crude LCMS: m/z = 358.3 [M + H]+. |

Intermediate-13: Phenyl(E)-N'-cyano-N-(4-(3,4-dichlorophenyl)but-3-yn-2-yl)carbamimidate (±)

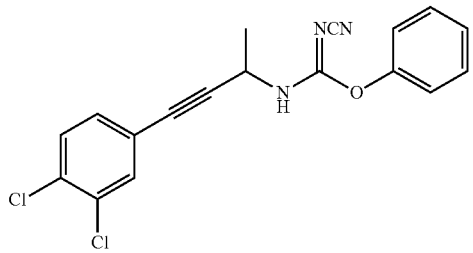

To a stirred solution of intermediate 11 (0.5 g, 1.996 mmol) and diphenyl cyanocarbonimidate (0.475 g, 1.996 mmol) in acetonitrile (30 mL) was added triethylamine (0.0.833 mL, 5.988 mmol) at RT and stirred for 16 h at RT. After completion of reaction, the reaction mixture was concentrated under reduced pressure. The residue obtained was purified by Combiflash® column on silica gel (hexanes/ethyl acetate=75/25) to give the title compound (0.5 g, 70%). LCMS: m/z 358.2 [M]$^+$

Intermediate-14: 1,2-dichloro-4-(3-isocyanatobut-1-yn-1-yl)benzene(±)

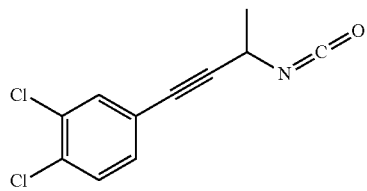

To a stirred solution of Intermediate 11a (0.200 g, 0.833 mmol) in DCM (10 mL) was added triposgene (0.0915 g, 0.308 mmol) and Sat. NaHCO$_3$ (10 mL) solution at 0° C. Then reaction mixture was stirred 1 h at RT. After completion of the reaction, DCM layer was separated and concentrated to obtain title compound (0.200 g, crude). The product obtained was taken for further steps without purification.

Intermediate-15: tert-Butyl 4-((1-((3,4-dichlorophenyl)ethynyl)cyclopentyl) carbamoyl) piperazine-1-carboxylate

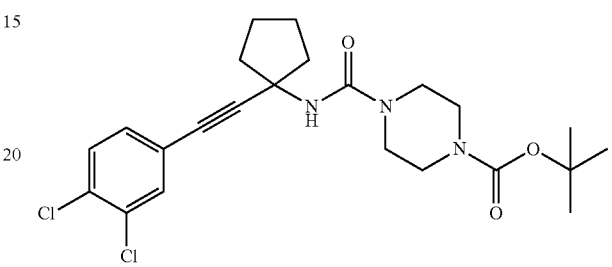

To a stirred suspension of intermediate 12c (0.180 g, 0.481 mmol) in DMSO (5.0 mL) was added tert-butyl piperazine-1-carboxylate (0.098 g, 0.529 mmol) and triethyl amine (0.20 mL, 1.443 mmol) at RT and it was heated to 60° C. for 16 h. The reaction mixture was poured into ice water and extracted with EtOAc. The combined EtOAc layers were washed with brine, water and dried over Na$_2$SO$_4$ and evaporated under reduced pressure. The obtained residue was purified by Combiflash® on silica gel (hexanes/ethyl acetate=60/40) to afford the title compound (0.204 g, 30.44%). LCMS: m/z=366.3 [M+H-100]$^+$.

The following intermediates were prepared essentially by the method of preparing Intermediate 15.

| Intermediate | Structure | IUPAC | Yield (%) & Analytical Data |
|---|---|---|---|
| 15a | ![structure] | tert-butyl 4-((4-(3-chloro-4-phenoxyphenyl)-but-3-yn-2-yl)-carbamoyl) piperazine-1-carboxylate (±). | Yield: 54%; LCMS: m/z = 484.2 [M + H]+. |
| 15b | ![structure] | tert-butyl 4-((4-(3-chloro-4-(diethylamino) phenyl)but-3-yn-2-yl)carbamoyl) piperazine-1-carboxylate (±). | Yield: 66%; LCMS: m/z = 464.2 [M + H]+. |

| Intermediate | Structure | IUPAC | Yield (%) & Analytical Data |
|---|---|---|---|
| 15c | 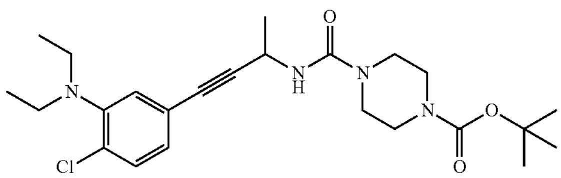 [SMILES: CCN(CC)c1cc(C#CC(C)NC(=O)N2CCN(C(=O)OC(C)(C)C)CC2)ccc1Cl] | tert-butyl 4-((4-(4-chloro-3-(diethylamino)phenyl)but-3-yn-2-yl)carbamoyl)piperazine-1-carboxylate (±). | Yield: 80%; LCMS: m/z = 463.4 [M + H]+. |
| 15d | 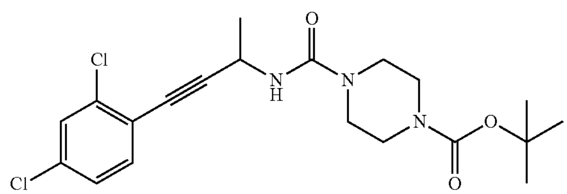 [SMILES: CC(C#Cc1ccc(Cl)cc1Cl)NC(=O)N1CCN(C(=O)OC(C)(C)C)CC1] | tert-butyl 4-((4-(2,4-dichlorophenyl)but-3-yn-2-yl)carbamoyl)piperazine-1-carboxylate(±). | Yield: 78%; LCMS: m/z = 425.9 [M]+. |
| 15e | 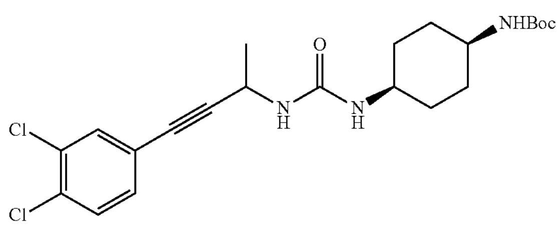 [SMILES: CC(C#Cc1ccc(Cl)c(Cl)c1)NC(=O)N[C@H]1CC[C@@H](NC(=O)OC(C)(C)C)CC1] | Cis-tert-butyl-((1s,4s)-4-(3-(4-(3,4-dichlorophenyl)but-3-yn-2-yl)ureido)-cyclohexyl)-carbamate (±) | Yield: 90%; LCMS: m/z = 354.2[M + H]+ |
| 15f | 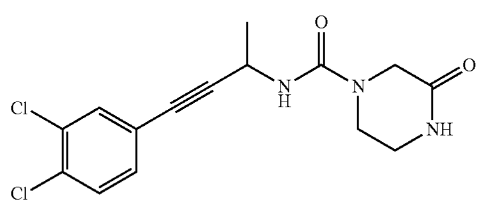 [SMILES: CC(C#Cc1ccc(Cl)c(Cl)c1)NC(=O)N1CCNC(=O)C1] | N-(4-(3,4-dichlorophenyl)but-3-yn-2-yl)-3-oxo-piperazine-1-carboxamide (±). | Yield: 99%; LCMS: m/z = 340.1 [M]+. |
| 15g | 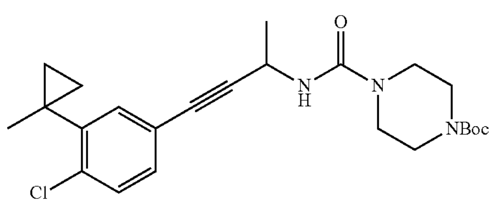 [SMILES: CC(C#Cc1ccc(Cl)c(C2(C)CC2)c1)NC(=O)N1CCN(C(=O)OC(C)(C)C)CC1] | tert-butyl 4-((4-(4-chloro-3-(1-methylcyclopropyl)phenyl)-but-3-yn-2-yl)carbamoyl)piperazine-1-carboxylate (±). | Yield: 68.7%; LCMS: m/z = 446.4 [M + H]+. |
| 15h | 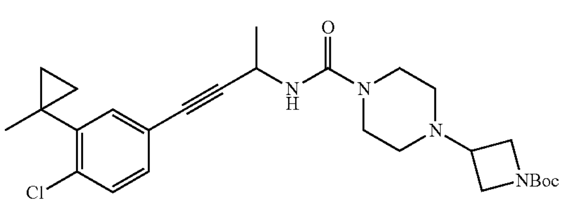 [SMILES: CC(C#Cc1ccc(Cl)c(C2(C)CC2)c1)NC(=O)N1CCN(C2CN(C(=O)OC(C)(C)C)C2)CC1] | tert-butyl 3-(4-((4-(4-chloro-3-(1-methylcyclopropyl)phenyl)but-3-yn-2-yl)-carbamoyl)piperazin-1-yl)-azetidine-1-carboxylate(±). | Yield: 58%; LCMS: m/z = 502.4 [M + H]+. |
| 15i | 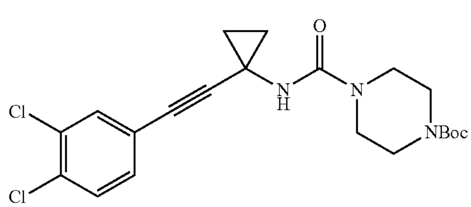 [SMILES: CC(C)(C)OC(=O)N1CCN(C(=O)NC2(C#Cc3ccc(Cl)c(Cl)c3)CC2)CC1] | tert-butyl 4-((1-((3,4-dichlorophenyl)ethynyl)-cyclopropyl)-carbamoyl)-piperazine-1-carboxylate | Yield: 100%; LCMS: m/z = 381.8 [M + H]+ |

| Intermediate | IUPAC | Yield (%) & Analytical Data |
|---|---|---|
| 15j | tert-butyl 4-((1-((4-chloro-3-(1-methylcyclopropyl)phenyl)-ethynyl)cyclopropyl)carbamoyl)piperazine-1-carboxylate | Yield: 56%; LCMS: Not analysed |
| 15k | tert-butyl 3-(4-((1-((4-chloro-3-(1-methylcyclopropyl)phenyl)-ethynyl)cyclopropyl)carbamoyl)piperazin-1-yl)-azetidine-1-carboxylate | Yield: 57%; LCMS: m/z = 513.4[M]+. |
| 15l | tert-butyl 4-((1-((6-methoxy-naphthalen-2-yl)ethynyl)cyclopropyl)carbamoyl)piperazine-1-carboxylate | Yield: Crude; LCMS: m/z = 450.4 [M]+. |
| 15m | tert-butyl 4-((1-(naphthalen-1-ylethynyl)cyclopropyl)carbamoyl)piperazine-1-carboxylate | Yield: 40%; LCMS: m/z = 420.4[M + H]+ |
| 15n | tert-butyl 4-((1-((3-bromo-4-chlorophenyl)-ethynyl)cyclopropyl)carbamoyl)piperazine-1-carboxylate | Yield: 54%; LCMS: m/z = 426[M − 56]+ |
| 15o | tert-butyl 4-((1-((4-chloro-2-methoxy-5-(1-methylcyclopropyl)phenyl)-ethynyl)cyclopropyl)carbamoyl)piperazine-1-carboxylate | Yield: 74%; LCMS: m/z = 488.4[M+]+ |
| 15p | tert-butyl 4-((1-((4-chloro-5-methoxy-2-(1-methylcyclopropyl)phenyl)-ethynyl)cyclopropyl)carbamoyl)piperazine-1-carboxylate | Yield: 80%; LCMS: m/z = 488.2[M+]+ |

Intermediate 15q: tert-butyl 4-((1-((4-chloro-3-ethynylphenyl)ethynyl) cyclopropyl) carbamoyl) piperazine-1-carboxylate

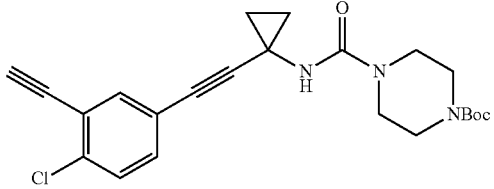 [SMILES: C#Cc1cc(C#CC2(NC(=O)N3CCN(C(=O)OC(C)(C)C)CC3)CC2)ccc1Cl]

Step-1: tert-butyl 4-((1-((4-chloro-3-((trimethylsilyl) ethynyl) phenyl)ethynyl) cyclopropyl) carbamoyl) piperazine-1-carboxylate

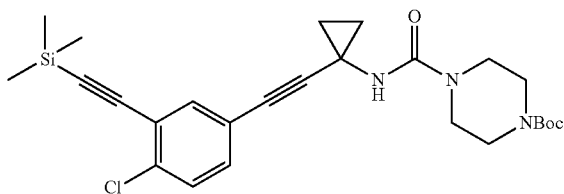 [SMILES: CC(C)(C)OC(=O)N1CCN(C(=O)NC2(C#Cc3ccc(Cl)c(C#C[Si](C)(C)C)c3)CC2)CC1]

To a solution of tert-butyl 4-((1-((3-bromo-4-chlorophenyl)ethynyl)cyclopropyl)carbamoyl) piperazine-1-carboxylate (15n) (0.150 g, 0.311 mmol), ethynyltrimethylsilane (0.046 g, 2.53 mmol) and triethyl amine (2 ml) in DMF (1 mL) was purged with argon gas for 10 min. Then CuI (0.006 g, 0.031 mmol) and Tetrakis(triphenylphosphine) palladium (O) (0.022 g, 0.031 mmol) were added at RT. The reaction mixture was incubated in microwave at 140° C. stirred for 4 h. The reaction mixture was concentrated under reduced pressure. The crude obtained above was purified by combiFlash® silica gel column (hexanes/EtOAc=60/40) to obtain the title compound (0.080 g, Impure). LCMS: m/z=500.5 [M+H]+.

Step-2: tert-butyl 4-((1-((4-chloro-3-ethynylphenyl) ethynyl)cyclopropyl)carbamoyl) piperazine-1-carboxylate

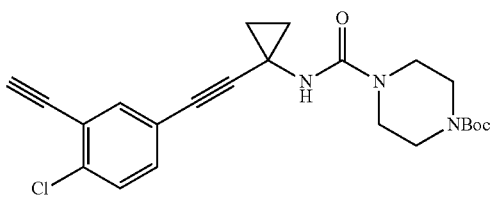 [SMILES: C#Cc1cc(C#CC2(NC(=O)N3CCN(C(=O)OC(C)(C)C)CC3)CC2)ccc1Cl]

To a stirred solution of tert-butyl 4-((1-((4-chloro-3-((trimethylsilyl)ethynyl) phenyl)ethynyl) cyclopropyl) carbamoyl)-piperazine-1-carboxylate (0.080 g, 0.160 mmol) in methanol (1 ml) was added K$_2$CO$_3$ (0.133 g, 0.480 mmol) and stirred for 1 h at room temperature. The reaction mixture was concentrated and purified by Combiflash® on silica gel (hexanes/EtOAc=60/40) to give the title compound (0.070 g, Impure). LCMS: m/z=428.3[M+H].

Intermediate-15r: N-(4-(3,4-dichlorophenyl) but-3-yn-2-yl)-4-oxopiperidine-1-carboxamide (±)

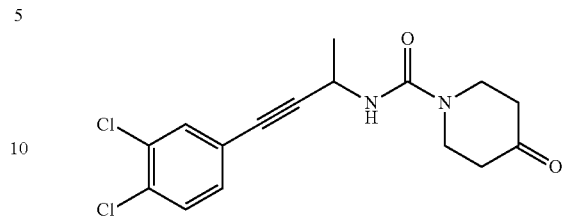

To a stirred suspension of Intermediate 12 (0.100 g, 0.299 mmol) and 4-oxopiperidin-1-ium 2,2,2-trifluoroacetate (0.076 g, 0.359 mmol) in DMSO (3.0 mL) was added triethyl amine (0.12 mL, 0.897 mmol) at RT and stirred for 14 h. The reaction mixture was poured into ice water and extracted with EtOAc. The combined EtOAc layers were washed with water and brine; dried over Na$_2$SO$_4$ and evaporated under reduced pressure. The obtained residue was purified by Combiflash® on silica gel (DCM/MeOH=98/02) to afford the title compound (0.095 g, 94.05%) as a solid. LCMS: m/z=339.3 [M+H]+.

Intermediate-15s: N-(4-(3,4-dichlorophenyl) but-3-yn-2-yl)-4-(hydroxyimino) piperidine-1-carboxamide (±)

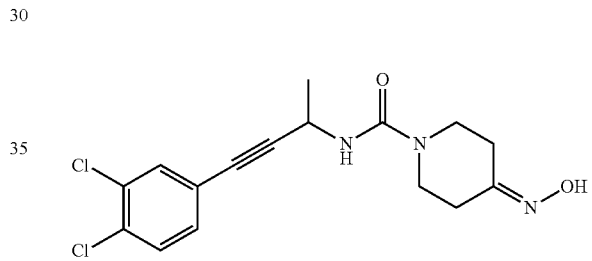

To a stirred suspension of N-(4-(3,4-dichlorophenyl)but-3-yn-2-yl)-4-oxopiperidine-1-carboxamide (Intermediate 15l) (0.090 g, 0.265 mmol) in Ethanol (4.0 mL) were added saturated sodium bicarbonate (0.036 g, 0.531 mmol) and Hydroxylamine hydrochloride (0.036 g, 0.531 mmol) at 0° C. The reaction mixture was allowed to warm to RT and stirred for 14 h and then was evaporated under reduced pressure. The obtained residue was taken in water extracted with EtOAc, the combined EtOAc layers were washed with brine; dried over Na$_2$SO$_4$ and evaporated under reduced pressure (0.090 g 45.74%). LCMS: m/z=354.3 [M+H]+.

Intermediate-15t: tert-butyl 4-((4-(3,4-dichlorophenyl)but-3-yn-2-yl) carbamoyl) piperazine-1-carboxylate (±)

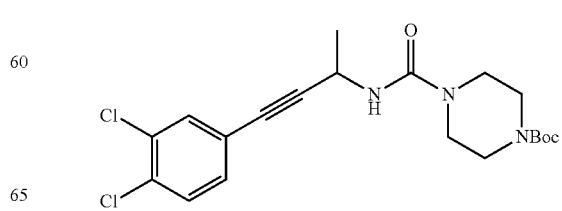

To a solution of 1,2-dichloro-4-iodobenzene (Intermediate 1a) (5.6 g, 20.75 mmol), tert-butyl 4-(but-3-yn-2-ylcarbamoyl) piperazine-1-carboxylate (Intermediate 8) (7 g, 24.91 mmol) and triethyl amine (8.66 mL, 62.25 mmol) in DMF (100 mL) was purged with argon gas for 20 min. Then Copper Iodide (0.79 g, 4.15 mmol) and Tetrakis(triphenylphosphine) palladium(O) (2.39 g, 2.07 mmol) were added at RT and the reaction mixture was again purged for 10 min. The reaction mixture was stirred for 2 h at 80° C. After completion of reaction, it was poured into ice water and extracted with EtOAc. The EtOAc layer was dried; concentrated and purified by combiFlash® silica gel column (hexanes/EtOAc=40/60) to obtain the title compound (7.0 g, 79.8%). LCMS: m/z=426.1 [M]+.

The following compounds were prepared essentially by the method of preparing Intermediate-15t with appropriate variations in reactants, reagents and reaction conditions.

| Intermediate | Structure | IUPAC | Yield (%)/Analytical Data |
|---|---|---|---|
| 15u | 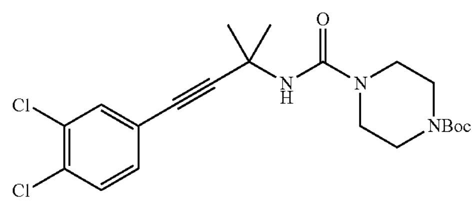 [SMILES: CC(C)(C#Cc1ccc(Cl)c(Cl)c1)NC(=O)N1CCN(C(=O)OC(C)(C)C)CC1] | tert-butyl 4-((4-(3,4-dichlorophenyl)-2-methylbut-3-yn-2-yl)carbamoyl)piperazine-1-carboxylate | Yield:50.3% LCMS: m/z = 384.1 [M − 56]+ |
| 15v | | tert-butyl 4-((1-(3,4-dichlorophenyl)pent-1-yn-3-yl)carbamoyl)piperazine-1-carboxylate (±) | Yield: 54.2% LCMS: m/z = 440.1 [M + H]+ |
| 15w | 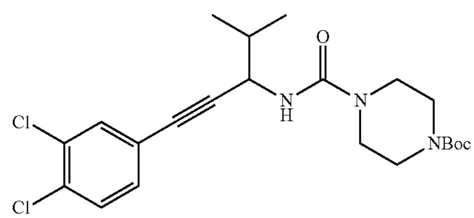 | tert-butyl 4-((1-(3,4-dichlorophenyl)-4-methylpent-1-yn-3-yl)carbamoyl)piperazine-1-carboxylate (±) | Yield: 50.78% LCMS: m/z = 398.8 [M − 56]+ |
| 15x | 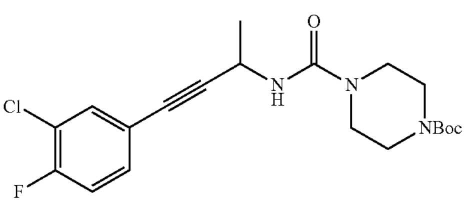 [SMILES: CC(C#Cc1ccc(F)c(Cl)c1)NC(=O)N1CCN(C(=O)OC(C)(C)C)CC1] | tert-butyl 4-((4-(3-chloro-4-fluorophenyl)-but-3-yn-2-yl)carbamoyl)piperazine-1-carboxylate(±) | Yield: 35.7% LCMS: m/z = 410.1 [M + H]+ |
| 15y | | tert-butyl 4-((4-(3-chloro-4-(trifluoromethyl)phenyl)but-3-yn-2-yl)carbamoyl)piperazine-1-carboxylate(±) | Yield: 64%; LCMS: m/z = 404.0 [M − 56]+ |
| 15z | 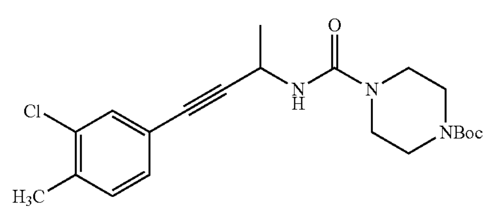 [SMILES: Cc1ccc(C#CC(C)NC(=O)N2CCN(C(=O)OC(C)(C)C)CC2)cc1Cl] | tert-butyl 4-((4-(3-chloro-4-methylphenyl)-but-3-yn-2-yl)carbamoyl)piperazine-1-carboxylate (±) | Yield: 43.16% LCMS: m/z = 350.2 [M − 56]+ |

-continued

| Intermediate | Structure | IUPAC | Yield (%)/ Analytical Data |
|---|---|---|---|
| 15aa | 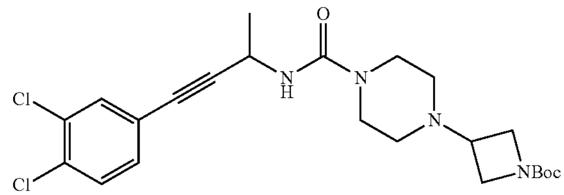 [SMILES: CC(C#Cc1ccc(Cl)c(Cl)c1)NC(=O)N1CCN(C2CN(C(=O)OC(C)(C)C)C2)CC1] | tert-butyl 3-(4-((4-(3,4-dichlorophenyl)-but-3-yn-2-yl)carbamoyl)piperazin-1-yl)azetidine-1-carboxylate (±) | Yield: 40%<br>LCMS: m/z = 481.1 [M + H]+ |
| 15ab | 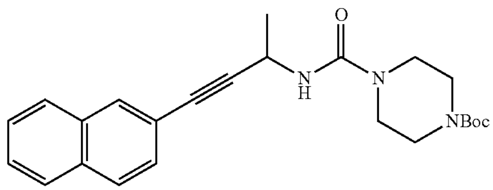 [SMILES: CC(C#Cc1ccc2ccccc2c1)NC(=O)N1CCN(C(=O)OC(C)(C)C)CC1] | tert-butyl 4-((4-(naphthalen-2-yl)but-3-yn-2-yl)carbamoyl)piperazine-1-carboxylate(±) | Yield: 53.0%<br>LCMS: m/z = 408.3 [M + H]+ |
| 15ac | 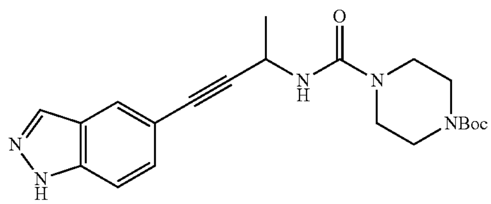 [SMILES: CC(C#Cc1ccc2[nH]ncc2c1)NC(=O)N1CCN(C(=O)OC(C)(C)C)CC1] | tert-butyl 4-((4-(1H-indazol-5-yl)but-3-yn-2-yl)carbamoyl)piperazine-1-carboxylate | Yield: 56%<br>LCMS: m/z = 398.1 [M + H]+ |
| 15ad | 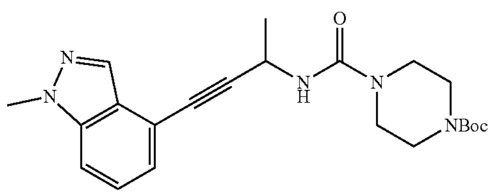 [SMILES: CC(C#Cc1cccc2c1cnn2C)NC(=O)N1CCN(C(=O)OC(C)(C)C)CC1] | tert-butyl 4-((4-(1-methyl-1H-indazol-4-yl)but-3-yn-2-yl)carbamoyl)piperazine-1-carboxylate(±) | Yield: 54%<br>LCMS: m/z = 412.1 [M + H]+ |
| 15ae | 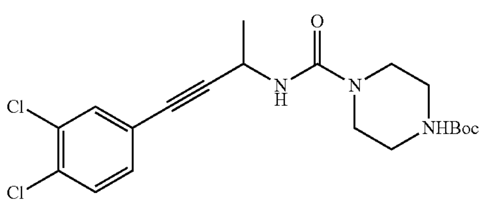 | tert-butyl (1-((4-(3,4-dichloro-phenyl)but-3-yn-2-yl)-carbamoyl)piperidin-4-yl)-carbamate(±) | Yield: 50%<br>LCMS: m/z = 440 [M + H]+ |
| 15af | 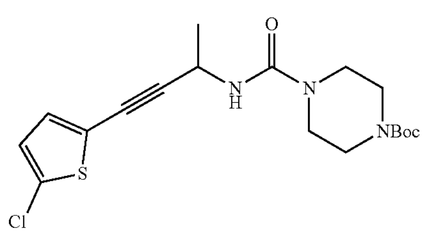 [SMILES: CC(C#Cc1ccc(Cl)s1)NC(=O)N1CCN(C(=O)OC(C)(C)C)CC1] | tert-butyl 4-((4-(5-chlorothio-phen-2-yl)but-3-yn-2-yl)-carbamoyl)piperazine-1-carboxylate (±) | Yield: 57.14%<br>LCMS: m/z = 398.3 [M + H]+ |
| 15ag | 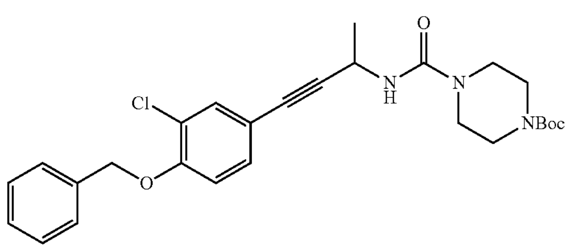 [SMILES: CC(C#Cc1ccc(OCc2ccccc2)c(Cl)c1)NC(=O)N1CCN(C(=O)OC(C)(C)C)CC1] | tert-butyl 4-((4-(4-(benzyloxy)-3-chlorophenyl)-but-3-yn-2-yl)-carbamoyl)piperazine-1-carboxylate (±) | Yield: 45.5%<br>LCMS: m/z = 498.6 [M + H]+ |

| Intermediate | Structure | IUPAC | Yield (%)/ Analytical Data |
|---|---|---|---|
| 15ah | 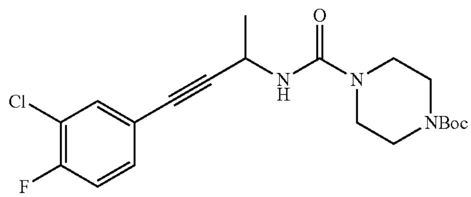 [SMILES: CC(C#Cc1ccc(F)c(Cl)c1)NC(=O)N1CCN(C(=O)OC(C)(C)C)CC1] | tert-butyl 4-((4-(3-chloro-4-fluorophenyl)-but-3-yn-2-yl)carbamoyl) piperazine-1-carboxylate (±) | Yield: 24.13% LCMS: m/z = 410 [M + H]+ |
| 15ai | 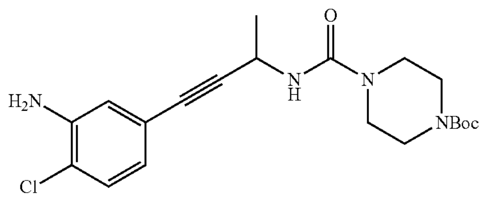 [SMILES: CC(C#Cc1ccc(Cl)c(N)c1)NC(=O)N1CCN(C(=O)OC(C)(C)C)CC1] | tert-butyl 4-((4-(3-amino-4-chlorophenyl)-but-3-yn-2-yl)carbamoyl) piperazine-1-carboxylate(±) | Yield: 23.66% LCMS: m/z = 407.3 [M + H]+ |

Intermediate-15aj: tert-Butyl 4-((4-(3-acetamido-4-chlorophenyl)but-3-yn-2-yl)carbamoyl) piperazine-1-carboxylate (±)

Intermediate-15ak: tert-Butyl 4-((4-(4-chloro-3-(cyclopropanecarboxamido) phenyl)but-3-yn-2-yl) carbamoyl) piperazine-1-carboxylate (±)

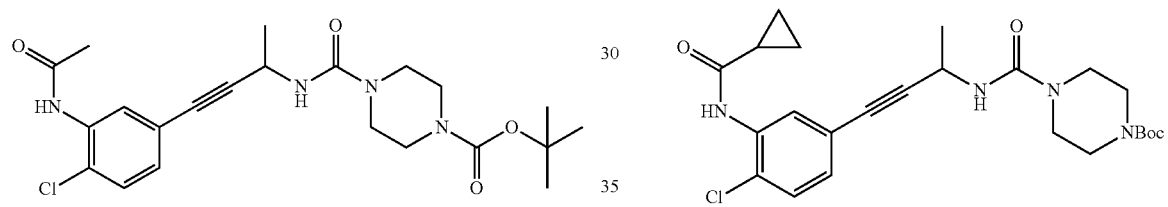

To a stirred solution of intermediate 15ai (0.200 g, 0.492 mmol) in DCM (25 mL) was added triethylamine (0.150 g, 1.47 mmol) and acetyl chloride at 0° C. The reaction mixture was stirred at room temperature for 16 h. The reaction mixture evaporated under reduced pressure. The crude obtained was purified by combiFlash® (60% EA in hexane) to afford the title compound (0.150 g, 68.1%) as a white solid. LCMS: m/z=349.3 [M+H-100]+.

The title compound was prepared as per the procedure described for the preparation of intermediate 15aj using Intermediate 15ai Yield: 64.3%; LCMS: m/z=375.3[M+H-100]+.

The following compounds were prepared essentially by the procedure described in the preparation of Intermediate 15t with appropriate variations in reactants, reagents and reaction conditions.

| Intermediate | Structure | IUPAC | Yield (%) & Analytical Data |
|---|---|---|---|
| 16 | 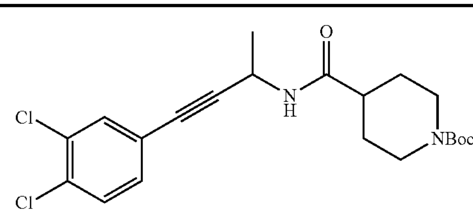 | tert-butyl 4-((4-(3,4-dichloro-phenyl)but-3-yn-2-yl)carbamoyl) piperidine-1-carboxylate (±) | Yield: 41 LCMS: m/z = 425.0[M + H]+ |
| 16a | 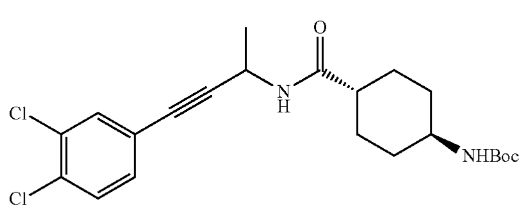 [SMILES: CC(C#Cc1ccc(Cl)c(Cl)c1)NC(=O)[C@H]1CC[C@H](NC(=O)OC(C)(C)C)CC1] | trans-tert-butyl-((1r,4r)-4-((4-(3,4-dichloro-phenyl)but-3-yn-2-yl)carbamoyl) cyclohexyl) carbamate (±) | Yield: 91 LCMS: m/z = 438.9[M + H]+ |

Intermediate-16b: tert-Butyl tert-butyl 3-(((S)-4-(3,4-dichlorophenyl)but-3-yn-2-yl)carbamoyl)pyrrolidine-1-carboxylate hydrochloride (±); and Intermediate-16c: tert-butyl 3-(((S)-4-(3,4-dichlorophenyl)but-3-yn-2-yl)carbamoyl)pyrrolidine-1-carboxylate hydrochloride (±)

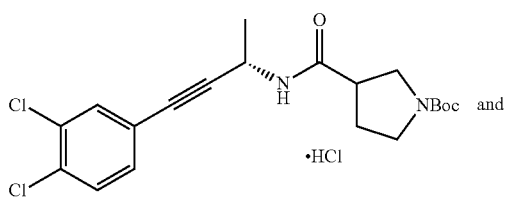

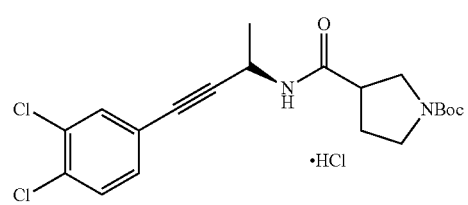

The title compounds were prepared as per the procedure described for the preparation of Intermediate 151 using Intermediate 9a and Intermediate 1a to get the mixture of isomers as crude. The crude compound was further purified by preparative TLC to obtain separated isomer 16b (Yield: 15%; LCMS: NA) & isomer 16c (Yield: 14%; LCMS: NA).

Intermediate 16d: tert-Butyl (1-((4-(3,4-dichlorophenyl)but-3-yn-2-yl)carbamoyl) cyclopentyl) carbamate (±)

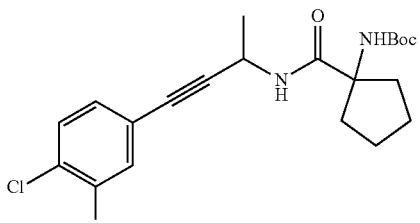

To a stirred suspension of Intermediate 11a (0.150 g, 0.5986 mmol) and 1-((tert-butoxycarbonyl)amino)cyclopentane-1-carboxylic acid (Intermediate 7d) (0.137 g, 0.5986 mmol) in DMF (4.0 mL) were added EDCl (0.126 g, 0.6585 mmol), HOBT (0.089 g, 0.6585 mmol) and triethyl amine (0.025 mL, 1.7960 mmol) at 0° C. and it was stirred for 14 h at RT. After completion of reaction, the reaction mixture was poured into ice water and extracted with EtOAc. The combined EtOAc layers were washed with water and brine; dried over $Na_2SO_4$ and evaporated under reduced pressure. The obtained crude was purified by Combiflash® on silica gel (hexanes/ethyl acetate=70/30) to afford the title compound (0.102 g crude). LCMS: m/z=325.2[M-100].

Intermediate-17: N-(4-(3,4-dichlorophenyl)but-3-yn-2-yl) piperazine-1-carboxamide hydrochloride (±)

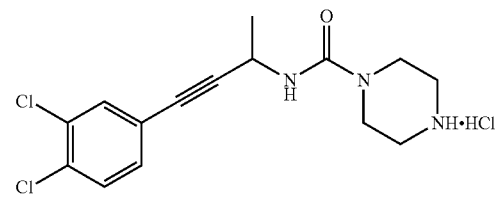

To a stirred solution of tert-butyl 4-((4-(3,4-dichlorophenyl)but-3-yn-2-yl)carbamoyl) piperazine-1-carboxylate (7.0 g, 16.43 mmol) in dioxane (100 mL), dioxane.HCl (70 mL) was added at 15° C. The reaction mixture was stirred for 16 h at RT. The reaction mixture was concentrated, the crude product was titurated with diethyl ether to afford the desired product (5.9 g, crude) and proceeded for next step.

The following intermediates were prepared essentially by the method of preparing Intermediate-17.

| Intermediate | Structure | IUPAC | Yield (%)/ Analytical Data |
|---|---|---|---|
| 17a | 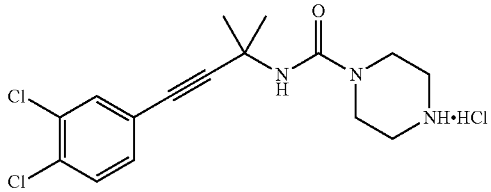 | N-(4-(3,4-dichlorophenyl)-2-methyl-but-3-yn-2-yl) piperazine-1-carboxamide hydrochloride | LCMS: m/z = 340.1 [M + H]+ |

| Intermediate | Structure | IUPAC | Yield (%)/Analytical Data |
|---|---|---|---|
| 17b | 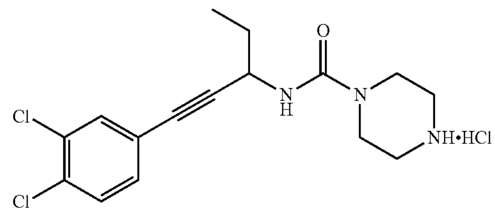 | N-(1-(3,4-dichlorophenyl)pent-1-yn-3-yl)piperazine-1-carboxamide hydrochloride (±) | Yield: Crude LCMS: m/z = NA |
| 17c | 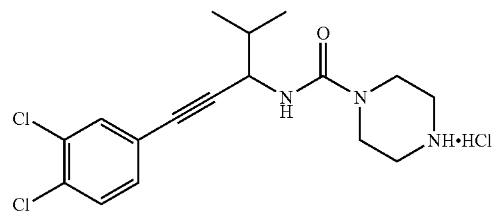 | N-(1-(3,4-dichlorophenyl)-4-methyl-pent-1-yn-3-yl)piperazine-1-carboxamide hydrochloride (±) | Yield: Crude LCMS: m/z = 353.95 [M + H]+ (Free base) |
| 17d | 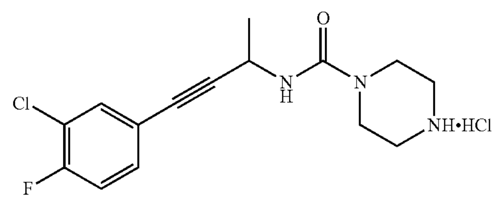 | N-(4-(3-chloro-4-fluorophenyl)but-3-yn-2-yl)piperazine-1-carboxamide hydrochloride (±) | Yield: Crude LCMS: m/z = 310.1 [M + H]+ (Free base) |
| 17e | 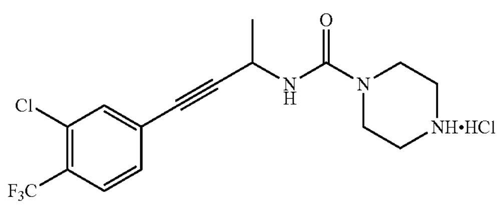 | N-(4-(3-chloro-4-(trifluoromethyl)phenyl)but-3-yn-2-yl)piperazine-1-carboxamide hydrochloride (±) | Yield: Crude LCMS: m/z = 359.7 [M + H]+ (Free base) |
| 17f | 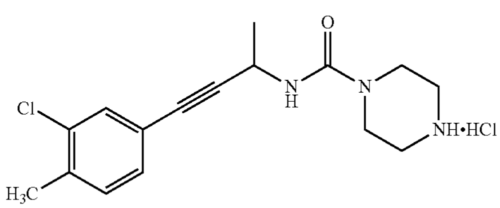 | N-(4-(3-chloro-4-methylphenyl)-but-3-yn-2-yl)-piperazine-1-carboxamide hydrochloride (±) | Yield: Crude LCMS: m/z = NA |
| 17g | 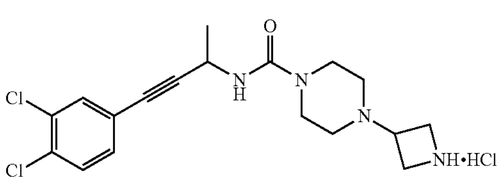 | 4-(azetidin-3-yl)-N-(4-(3,4-dichlorophenyl)but-3-yn-2-yl) piperazine-1-carboxamide hydrochloride (±) | Yield: 87% LCMS: m/z = 381.2 [M + H]+ (Free base) |
| 17h | 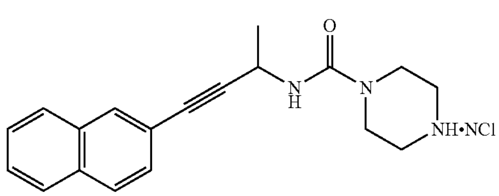 | N-(4-(naphthalen-2-yl)but-3-yn-2-yl)piperazine-1-carboxamide hydrochloride (±) | Yield: Crude LCMS: m/z = 308.2 [M + H]+ (Free base) |

-continued

| Intermediate | Structure | IUPAC | Yield (%)/ Analytical Data |
|---|---|---|---|
| 17i | 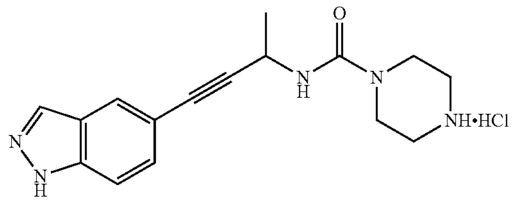 | N-(4-(1H-indazol-5-yl)but-3-yn-2-yl) piperazine-1-carboxamide hydrochloride (±) | Yield: 89% LCMS: m/z = 297.9 [M + H]+ (Free base) |
| 17j | 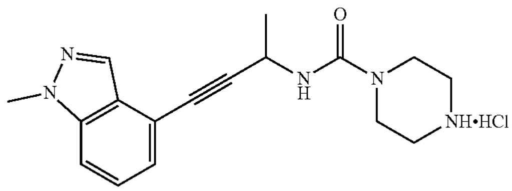 | N-(4-(1-methyl-1H-indazol-4-yl)-but-3-yn-2-yl) piperazine-1-carboxamide hydrochloride (±) | Yield: 74% LCMS: m/z = 311.8 [M + H]+ (Free base) |
| 17k | 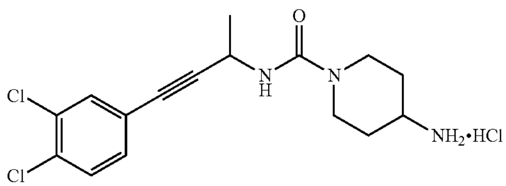 | 4-amino-N-(4-(3,4-dichlorophenyl)but-3-yn-2-yl) piperidine-1-carboxamide hydrochloride (±) | Yield: Crude LCMS: m/z = 340.1 [M + H]+ (Free base) |
| 17l | 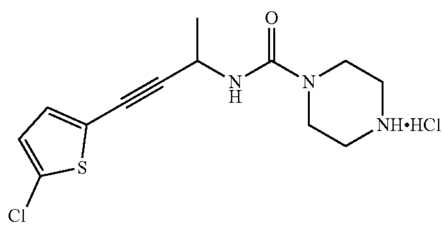 | N-(4-(5-chlorothiophen-2-yl)-but-3-yn-2-yl) piperazine-1-carboxamide hydrochloride (±) | Yield: Crude LCMS: m/z = NA |
| 17m | 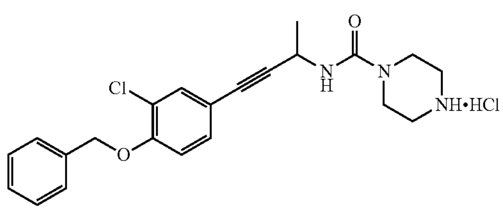 | N-(4-(4-(benzyloxy)-3-chlorophenyl)but-3-yn-2-yl) piperazine-1-carboxamide hydrochloride (±) | Yield: Crude LCMS: m/z = NA |
| 17n | 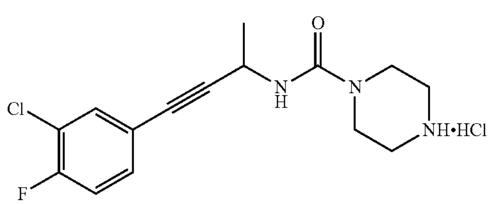 | N-(4-(3-chloro-4-fluorophenyl)-but-3-yn-2-yl) piperazine-1-carboxamide hydrochloride (±) | Yield: 94.5% LCMS: m/z = 310.3 [M + H]+ |
| 17o | 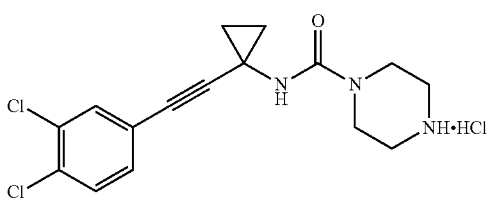 | N-(1-((3,4-dichlorophenyl) ethynyl)cyclopropyl) piperazine-1-carboxamide hydrochloride | Yield: 83.6%; LCMS: m/z = 338.2 [M]+. |

-continued

| Intermediate | Structure | IUPAC | Yield (%)/ Analytical Data |
|---|---|---|---|
| 17p | 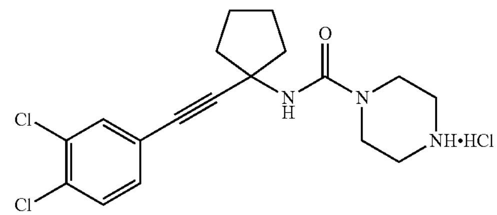 | N-(1-((3,4-dichlorophenyl)-ethynyl)cyclopentyl) piperazine-1-carboxamide hydrochloride | Yield: 88% LCMS: m/z = 368.2[M]+. |
| 17q | 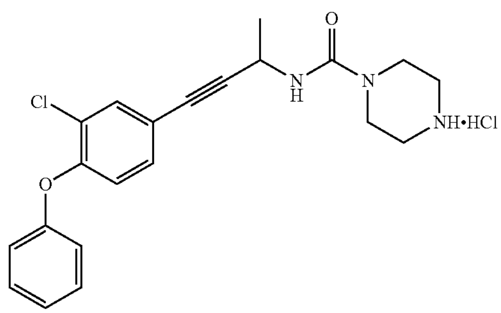 | N-(4-(3-chloro-4-phenoxyphenyl)-but-3-yn-2-yl) piperazine-1-carboxamide hydrochloride (±) | Yield: crude; LCMS: m/z = 384.1 [M + H]+. |
| 17r | 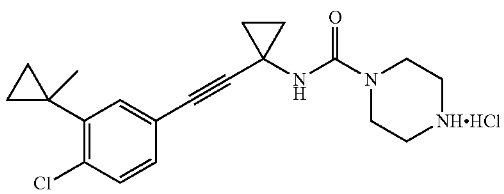 | N-(1-((4-chloro-3-(1-methyl-cyclopropyl)phenyl)ethynyl)-cyclopropyl) piperazine-1-carboxamide hydrochloride | Yield: crude; LCMS: m/z = 358.3 [M + H]+. |
| 17s | 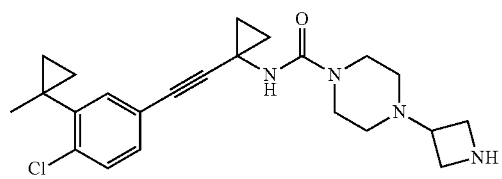 [SMILES: CC1(c2cc(C#CC3(NC(=O)N4CCN(C5CNC5)CC4)CC3)ccc2Cl)CC1] | 4-(azetidin-3-yl)-N-(1-((4-chloro-3-(1-methylcyclopropyl)phenyl)-ethynyl)cyclopropyl) piperazine-1-carboxamide | Yield: 100%; LCMS: m/z = 413.3 [M + H]+ |
| 17t | 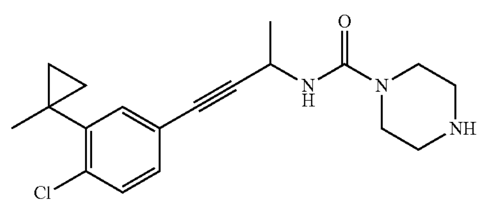 [SMILES: CC(C#Cc1ccc(Cl)c(C2(C)CC2)c1)NC(=O)N1CCNCC1] | N-(4-(4-chloro-3-(1-methylcyclopropyl)phenyl)-but-3-yn-2-yl) piperazine-1-carboxamide (±) | Yield: 100%; LCMS: m/z = 346.3 [M + H]+ |
| 17u | 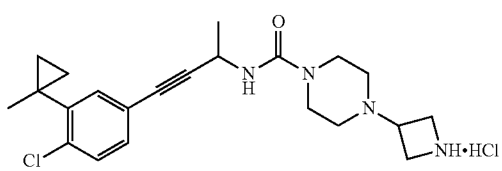 | 4-(azetidin-3-yl)-N-(4-(4-chloro-3-(1-methylcyclopropyl)phenyl) but-3-yn-2-yl) piperazine-1-carboxamide hydrochloride (±) | Yield: 92.6%; LCMS: m/z = 401.4 [M + H]+ |
| 17v | 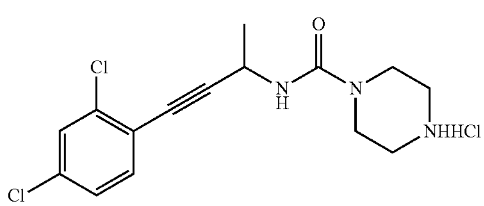 | N-(4-(2,4-dichlorophenyl)but-3-yn-2-yl) piperazine-1-carboxamide hydrochloride (±) | Yield: 94%; LCMS: m/z = 325.7 [M + H]+ |

-continued

| Intermediate | Structure | IUPAC | Yield (%)/ Analytical Data |
|---|---|---|---|
| 17w | [structure] | N-(4-(3-chloro-4-(diethylamino)phenyl)but-3-yn-2-yl)piperazine-1-carboxamide hydrochloride (±) | Yield: crude; LCMS: m/z = 362.3 [M + H]+ |
| 17x | [structure] | N-(4-(4-chloro-3-(diethylamino)phenyl)but-3-yn-2-yl)piperazine-1-carboxamide hydrochloride | Yield: crude; LCMS: m/z = 363.0 [M + H]+ |
| 17y | [structure] | Cis- 1-((1s,4s)-4-((l2-chloranyl)amino)cyclohexyl)-3-(4-(3,4-dichlorophenyl)but-3-yn-2-yl)urea (±). | Yield: 92% LCMS: Not ionized |
| 17z | [structure] | N-(1-((6-methoxynaphthalen-2-yl)ethynyl)cyclopropyl)piperazine-1-carboxamide hydrochloride | Crude LCMS: m/z = 350.3 [M + H]+ (Free base) |

The following Intermediates 17aa to 17ad were obtained by treating their respective Boc protected precursors with TFA in DCM and concentrated in vacuum.

| Intermediate | Structure | IUPAC | Yield (%)/ Analytical Data |
|---|---|---|---|
| 17aa | [structure] | N-(1-(naphthalen-1-ylethynyl)cyclopropyl)piperazine-1-carboxamide (TFASalt) | Yield: 85.6%; LCMS: m/z = 320.3 [M + H]+ (Free base) |
| 17ab | [structure] | N-(1-((4-chloro-3-ethynylphenyl)ethynyl)cyclopropyl) piperazine-1-carboxamide (TFA salt) | Yield: Crude LCMS: m/z = 328.3 [M + H]+ (Free base) |

| Inter-mediate | Structure | IUPAC | Yield (%)/ Analytical Data |
|---|---|---|---|
| 17ac | 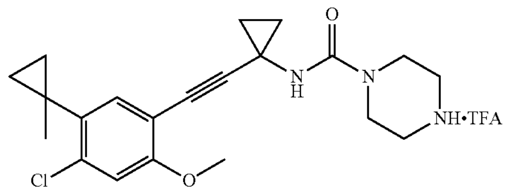 | N-(1-((4-chloro-2-methoxy-5-(1-methylcyclopropyl)phenyl)ethynyl)-cyclopropyl)piperazine-1-carboxamide (TFA salt) | Yield: 99% LCMS: m/z = 388.3 [M + H]+ (Free base) |
| 17ad | 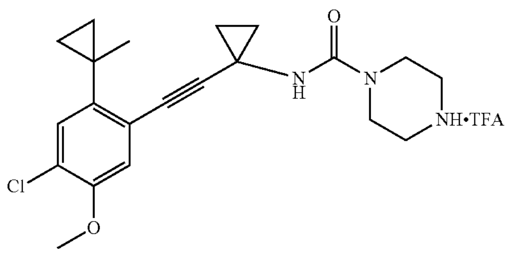 | N-(1-((4-chloro-5-methoxy-2-(1-methylcyclopropyl)phenyl)ethynyl)-cyclopropyl)piperazine-1-carboxamide (TFA salt) | Yield: 96% LCMS: m/z = 388.3 [M + H]+ (Free base) |

The compounds of Intermediates (17ae & 17af) were obtained by treating their respective HCl salt with sodium carbonate.

| Inter-mediate | Structure | IUPAC | Yield (%)/ Analysis |
|---|---|---|---|
| 17ae | 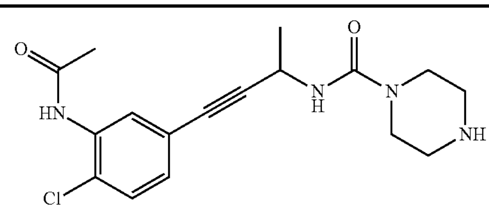 | N-(4-(3-acetamido-4-chlorophenyl)-but-3-yn-2-yl)piperazine-1-carboxamide (±) | Yield: 85.8% LCMS: m/z = 349.3 [M + H]+ |
| 17af | 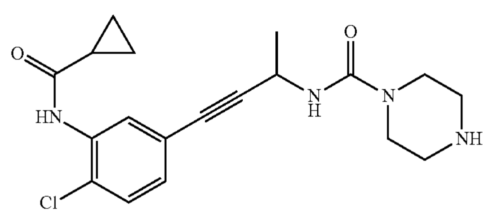 [SMILES: CC(C#Cc1ccc(Cl)c(NC(=O)C2CC2)c1)NC(=O)N1CCNCC1] | N-(4-(4-chloro-3-(cyclopropane-carboxamido)phenyl)but-3-yn-2-yl)piperazine-1-carboxamide (±) | Yield: 84.7% LCMS: m/z = 375.3 [M + H]+ |

Intermediate 17ag: Trans-3-(4-(3,4-dichlorophenyl)but-3-yn-2-yl)-1-methyl-1-(2-(methyl amino) cyclohexyl)urea(±)

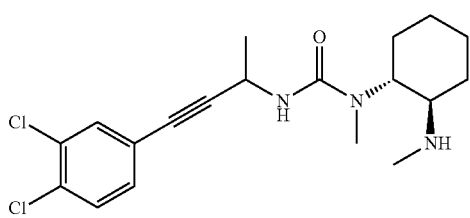 [SMILES: CN[C@@H]1CCCC[C@H]1N(C)C(=O)NC(C)C#Cc1ccc(Cl)c(Cl)c1]

To a stirred suspension of Intermediate 12 (0.150 g, 0.157 mmol) and trans-N1,N2-dimethylcyclohexane-1,2-diamine (±) (Intermediate 4e) (0.095 g, 0.718 mmol) in DMSO (5.0 mL) was added trimethylamine (0.18 mL, 2.992 mmol) at RT and stirred for 18 h. The reaction mixture was poured into ice water and extracted with EtOAc. The combined EtOAc layers were washed with water and brine; dried over $Na_2SO_4$ and evaporated under reduced pressure. The obtained residue was purified by Combiflash® on silica gel (DCM/MeOH=93/07) to afford the title compound (0.060 g, 35.08%) as a solid. LCMS: m/z=382.30 [M+H]+.

The following compounds were prepared essentially as per the procedure described for the preparation of Intermediate 17 with appropriate variations in reactants, reagents and reaction conditions.

| Intermediate | Structure | IUPAC | Yield (%)/Analytical Data |
|---|---|---|---|
| 18 | 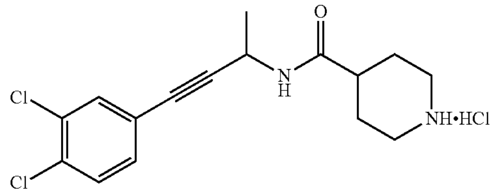 | N-(4-(3,4-dichlorophenyl)-but-3-yn-2-yl)piperidine-4-carboxamide hydrochloride (±) | Yield: 83%<br>LCMS: NA |
| 18a | 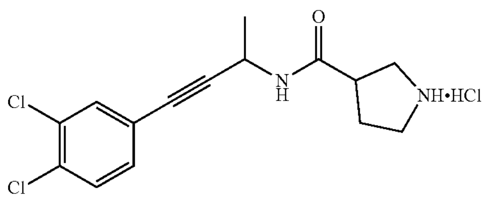 | N-(4-(3,4-dichlorophenyl)-but-3-yn-2-yl)pyrrolidine-3-carboxamide hydrochloride (±) (Isomer-1) | Yield: crude<br>LCMS: NA |
| 18b | 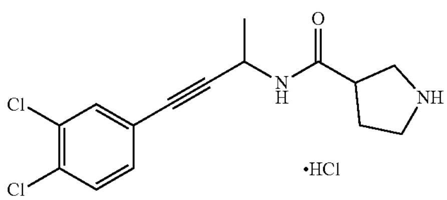 [SMILES: CC(C#Cc1ccc(Cl)c(Cl)c1)NC(=O)C1CCNC1 ; Cl] | N-(4-(3,4-dichlorophenyl)-but-3-yn-2-yl)pyrrolidine-3-carboxamide hydrochloride (±) (Isomer-2) | Yield: crude<br>LCMS: NA |
| 18c | 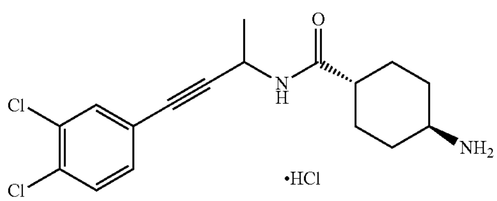 [SMILES: CC(C#Cc1ccc(Cl)c(Cl)c1)NC(=O)[C@H]1CC[C@H](N)CC1 ; Cl] | trans-(1r,4r)-4-amino-N-(4-(3,4-dichlorophenyl)but-3-yn-2-yl)cyclohexane-1-carboxamide hydrochloride (±) | Yield: 92%<br>LCMS:<br>m/z = 340.2<br>[M + H − 100]+ |
| 18d | 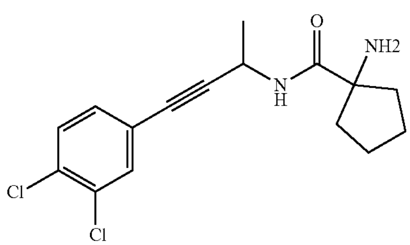 [SMILES: CC(C#Cc1ccc(Cl)c(Cl)c1)NC(=O)C1(N)CCCC1] | 1-amino-N-(4-(3,4-dichlorophenyl)but-3-yn-2-yl)cyclopentane-1-carboxamide (±) | Yield: crude<br>LCMS: m/z = 325.2[M]+ |

Example-1: 4-acryloyl-N-(4-(3,4-dichlorophenyl)but-3-yn-2-yl) piperazine-1-carboxamide (±)

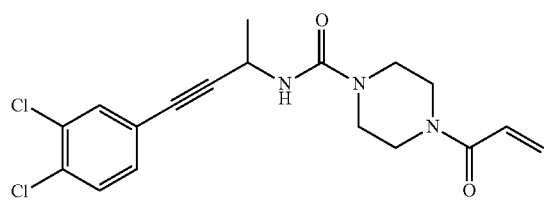

To a stirred suspension of N-(4-(3,4-dichlorophenyl)but-3-yn-2-yl) piperazine-1-carboxamide hydrochloride (Intermediate 17) (5.9 g, 16.34 mmol) in DCM (70 mL), triethylamine (4.95 g, 49.02 mmol) and acryloyl chloride (1.92 g, 21.24 mmol) was added at 15° C. The reaction was stirred at RT for 3 h. After completion of the reaction, the reaction mixture was washed with sat. NaHCO$_3$ solution and brine. DCM layer was concentrated to obtain the crude the crude compound which was purified by Combiflash® silica gel column chromatography (DCM/MeOH=97/3) to get the compound (3.2 g, 51.5%). HPLC: 98.7%; LCMS: m/z=379.9 [M+H]+.

$^1$H NMR (400 MHz, CDCl$_3$): δ 7.53 (d, J=1.86 Hz, 1H), 7.40 (d, J=8.31 Hz, 1H), 7.31-7.22 (m, 1H), 6.59 (dd, J=10.49, 16.79 Hz, 1H), 6.37 (dd, J=1.82, 16.87 Hz, 1H), 5.78 (dd, J=1.84, 10.52 Hz, 1H), 4.97 (q, J=7.14 Hz, 1H), 4.67 (d, J=7.87 Hz, 1H), 3.84-3.37 (m, 8H), 1.53 (d, J=6.87 Hz, 3H)

The compounds of Examples 1a & 1b were separated from Example 1 by chiral preparative HPLC as per the following method to afford the separated two isomers (Isomer-1 and Isomer-2 of Example-1)

Method:

| COLUMN: | LUX AMYLOSE-2 (21.2 × 250 mm-5 µm); |
|---|---|
| MOBILE PHASE: | HEXANE (A), 0.1% TFA IN ETHANOL (B) |
| FLOW: | 20 mL/min |
| ISOCRATIC: | 80:20 |

Example 1a: 4-acryloyl-N-(4-(3,4-dichlorophenyl)but-3-yn-2-yl) piperazine-1-carboxamide (Isomer-1)

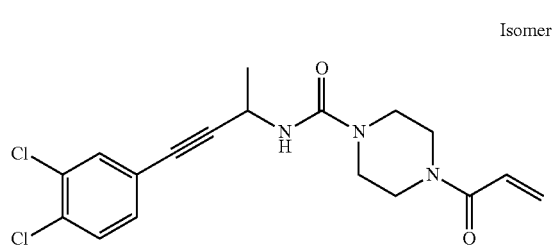

Isomer-1

Yield: 46.6%; HPLC: 99.09%; LCMS: m/z=379.9 [M+H]$^+$;

Example 1b: 4-acryloyl-N-(4-(3,4-dichlorophenyl)but-3-yn-2-yl) piperazine-1-carboxamide (Isomer-2)

Yield: 46.0%; HPLC: 99.09%; LCMS: m/z=379.9 [M+H]$^+$;

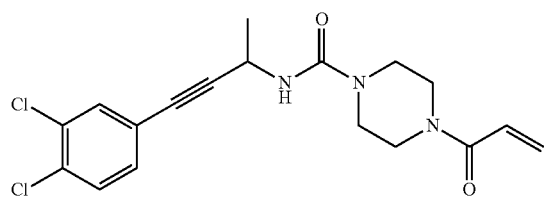

Isomer-2

Example-2: 4-acryloyl-N-(1-(3,4-dichlorophenyl)pent-1-yn-3-yl)piperazine-1-carboxamide (±)

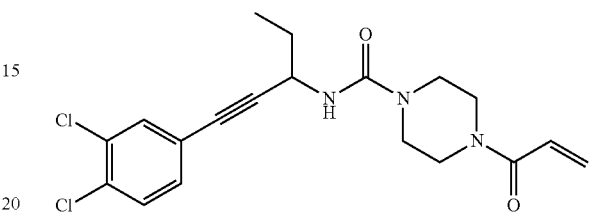

The example-2 was prepared according to the procedure described in the preparation of Example 1 with appropriate variations in reactants, reagents and reaction conditions.
Yield: 64%; HPLC: 97.47%; LCMS: m/z=394.0 [M+H]$^+$;
$^1$H NMR (400 MHz, CDCl$_3$): δ 7.48 (d, J=1.89 Hz, 1H), 7.35 (d, J=8.31 Hz, 1H), 7.28-7.17 (m, 1H), 6.53 (dd, J=10.47, 16.79 Hz, 1H), 6.31 (dd, J=1.87, 16.79 Hz, 1H), 5.73 (dd, J=1.87, 10.48 Hz, 1H), 4.80 (td, J=5.81, 7.82 Hz, 1H), 4.64 (d, J=8.12 Hz, 1H), 3.82-3.30 (m, 8H), 1.90-1.41 (m, 2H), 1.04 (t, J=7.37 Hz, 3H).

The racemic mixture obtained above was purified by chiral preparative HPLC to afford the separated isomers (2a &2b).

| Example | Structure | Yield (%) & Analytical Data |
|---|---|---|
| 2a | Isomer-1 | Yield: 50%; LCMS: m/z = 394.2 [M + H]$^+$; HPLC: 97.6%; |
| 2b | Isomer-2 | Yield: 50%; LCMS: m/z = 394.2 [M + H]$^+$; HPLC: 98.4% |

The following examples were prepared according to the procedure described in the preparation of Example 1 with appropriate variations in reactants, reagents and reaction conditions.

| Example | Structure | Yield (%) & Analytical Data |
|---|---|---|
| 3 | (3,4-dichlorophenyl alkyne, C(CH₃)₂, NH-C(O)-piperazine-acryloyl) | Yield: 22.4%; HPLC: 94.52%; LCMS: m/z = 394.2 [M + H]⁺; ¹H NMR (400 MHz, CDCl₃) δ 7.59 (dd, J = 0.95, 1.96 Hz, 1H), 7.39 (dd, J = 0.93, 8.41 Hz, 1H), 7.29-7.23 (m, 1H), 6.60 (ddd, J = 0.97, 10.52, 16.83 Hz, 1H), 6.35 (ddd, J = 0.87, 1.65, 16.76 Hz, 1H), 5.77 (ddd, J = 0.99, 1.87, 10.48 Hz, 1H), 5.36 (s, 1H), 3.75 (d, J = 49.75 Hz, 4H), 3.53 (dd, J = 3.84, 6.35 Hz, 4H), 1.42 (d, J = 1.08 Hz, 6H). |
| 4 | (3,4-dichlorophenyl alkyne, CH(iPr), NH-C(O)-piperazine-acryloyl) | Yield: 32.3%; HPLC: 98.0%; LCMS: m/z = 408.2; [M + H]⁺; ¹H NMR (400 MHz, CDCl₃) δ 7.50 (d, J = 1.91 Hz, 1H), 7.37 (d, J = 8.30 Hz, 1H), 7.28-7.20 (m, 1H), 6.55 (dd, J = 10.49, 16.79 Hz, 1H), 6.34 (dd, J = 1.87, 16.74 Hz, 1H), 5.75 (dd, J = 1.86, 10.49 Hz, 1H), 4.79 (dd, J = 5.45, 8.32 Hz, 1H), 4.66 (d, J = 8.35 Hz, 1H), 3.57 (dd, J = 47.14, 85.68 Hz, 8H), 2.00 (dq, J = 6.12, 6.60, 13.11 Hz, 1H), 1.04 (dd, J = 2.22, 6.68 Hz, 6H). |
| 5 | (3-Cl-4-F-phenyl alkyne, CH(CH₃), NH-C(O)-piperazine-acryloyl) | Yield: 25.10%; HPLC: 98.81%; LCMS: m/z 364.0 [M + H]⁺; ¹H NMR (400 MHz, CDCl₃) δ 7.45 (dd, J = 2.08, 7.00 Hz, 1H), 7.31-7.20 (m, 1H), 7.05 (t, J = 8.69 Hz, 1H), 6.54 (dd, J = 10.50, 16.78 Hz, 1H), 6.32 (dd, J = 1.89, 16.79 Hz, 1H), 5.73 (dd, J = 1.88, 10.47 Hz, 1H), 4.92 (p, J = 7.07 Hz, 1H), 4.63 (d, J = 7.88 Hz, 1H), 3.80-3.28 (m, 8H), 1.48 (d, J = 6.85 Hz, 3H). |
| 6 | (3-Cl-4-CF₃-phenyl alkyne, CH(CH₃), NH-C(O)-piperazine-acryloyl) | Yield: 22.27%; HPLC: 99.58%; LCMS: m/z = 414.0 [M + H]+; ¹H NMR (400 MHz, CDCl₃) δ 7.59 (d, J = 8.17 Hz, 1H), 7.52 (d, J = 1.29 Hz, 1H), 7.36 (ddd, J = 0.88, 1.62, 8.01 Hz, 1H), 6.54 (dd, J = 10.49, 16.79 Hz, 1H), 6.32 (dd, J = 1.86, 16.79 Hz, 1H), 5.73 (dd, J = 1.83, 10.48 Hz, 1H), 4.96 (p, J = 7.09 Hz, 1H), 4.65 (d, J = 7.99 Hz, 1H), 3.81-3.32 (m, 8H), 1.50 (d, J = 6.89 Hz, 3H). |
| 7 | (3-Cl-4-CH₃-phenyl alkyne, CH(CH₃), NH-C(O)-piperazine-acryloyl) | Yield: 28.5%; HPLC: 98.08%; LCMS: m/z = 360.2 [M + H]+; ¹H NMR (400 MHz, CDCl₃) δ 7.40 (d, J = 1.54 Hz, 1H), 7.22-7.12 (m, 2H), 6.56 (dd, 10.50, 16.79 Hz, 1H), 6.34 (dd, J = 1.88, 16.79 Hz, 1H), 5.75 (dd, J = 1.86, 10.54 Hz, 1H), 4.95 (p, J = 7.01 Hz, 1H), 4.66 (d, J = 7.83 Hz, 1H), 3.79-3.32 (m, 8H), 2.36 (s, 3H), 1.50 (d, J = 6.83 Hz, 3H). |

| Example | Structure | Yield (%) & Analytical Data |
|---|---|---|
| 8 | 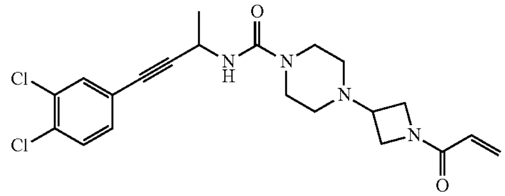 [SMILES: C=CC(=O)N1CC(N2CCN(C(=O)NC(C)C#Cc3ccc(Cl)c(Cl)c3)CC2)C1] | Yield: 40%; HPLC: 94.26%; LCMS: m/z = 436.3[M + H]⁺; ¹H NMR (400 MHz, DMSOd₆) δ 8.31 (s, 1H), 7.70-7.59 (m, 1H), 7.38 (dd, J = 1.98, 8.35 Hz, 1H), 6.97 (d, J = 8.04 Hz, 1H), 6.29 (dd, J = 10.28, 17.00 Hz, 1H), 6.09 (dd, J = 2.28, 17.01 Hz, 1H), 5.66 (dd, J = 2.27, 10.27 Hz, 1H), 4.76 (p, J = 7.27 Hz, 1H), 4.22 (t, J = 8.07 Hz, 1H), 4.03 (dd, J = 4.91, 8.86 Hz, 1H), 3.92 (dd, J = 7.28, 10.30 Hz, 1H), 3.73 (dt, J = 5.02, 10.24 Hz, 1H), 3.40-3.10 (m, 5H), 2.38-2.15 (m, 4H), 1.38 (d, J = 7.00 Hz, 3H) |
| 9 | 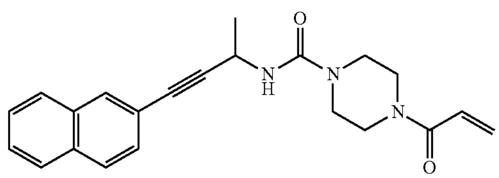 [SMILES: C=CC(=O)N1CCN(C(=O)NC(C)C#Cc2ccc3ccccc3c2)CC1] | Yield: 3.0%; HPLC: 95.68%; LCMS: m/z = 362.1 [M + H]⁺, 1H NMR (400 MHz, CDCl₃); δ 7.95 (d, J = 1.47 Hz, 1H), 7.87-7.71 (m, 3H), 7.54-7.41 (m, 3H), 6.56 (dd, J = 10.48, 16.81 Hz, 1H), 6.34 (dd, J = 1.85, 16.79 Hz, 1H), 5.75 (dd, J = 1.86, 10.48 Hz, 1H), 5.02 (p, J = 6.87 Hz, 1H), 4.73 (d, J = 7.87 Hz, 1H), 3.75-3.42 (m, 8H), 1.56 (d, J = 5.91 Hz, 3H). |
| 10 | 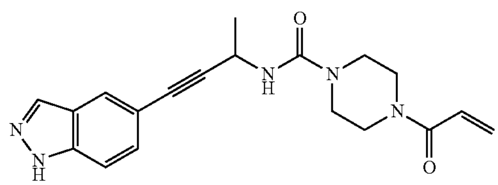 [SMILES: C=CC(=O)N1CCN(C(=O)NC(C)C#Cc2ccc3[nH]ncc3c2)CC1] | Yield: 17%; HPLC: 93.84%; LCMS: m/z = 352.1[M + H]+; ¹H NMR (400 MHz, DMSOd6): δ 13.23 (s, 1H), 8.07 (t, J = 1.28 Hz, 1H), 7.85 (d, J = 1.29 Hz, 1H), 7.52 (dt, J = 0.90, 8.53 Hz, 1H), 7.33 (dd, J = 1.50, 8.59 Hz, 1H), 7.07 (d, J = 8.08 Hz, 1H), 6.83 (dd, J = 10.43, 16.65 Hz, 1H), 6.13 (dd, J = 2.42, 16.66 Hz, 1H), 5.81-5.58 (m, 1H), 4.87-4.67 (m, 1H), 3.63-3.34 (m, 8H), 1.42 (d, J = 6.94 Hz, 3H). |
| 11 | 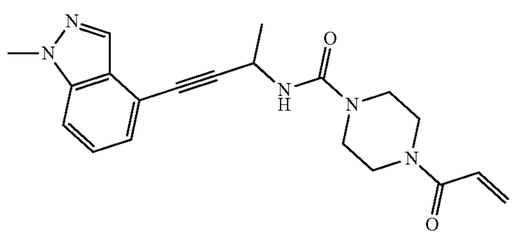 [SMILES: C=CC(=O)N1CCN(C(=O)NC(C)C#Cc2cccc3c2cnn3C)CC1] | Yield: 21%; HPLC: 94.79%; LCMS: m/z = 366.1 [M + H]⁺; ¹HNMR (400 MHz, DMSOd₆): δ 8.08-8.00 (m, 1H), 7.67 (d, J = 8.29 Hz, 1H), 7.38 (ddd, J = 0.91, 7.06, 8.27 Hz, 1H), 7.19 (d, J = 7.12 Hz, 1H), 7.12 (d, J = 8.11 Hz, 1H), 6.89-6.76 (m, 1H), 6.19-6.06 (m, 1H), 5.70 (ddd, J = 0.93, 2.55, 10.53 Hz, 1H), 4.92-4.80 (m, 1H), 4.06 (s, 3H), 3.54 (d, J = 16.61 Hz, 4H), 3.34-3.29 (m, 4H), 1.47 (d, J = 6.95 Hz, 3H). |
| 12 | 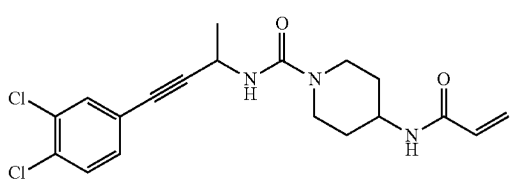 [SMILES: C=CC(=O)NC1CCN(C(=O)NC(C)C#Cc2ccc(Cl)c(Cl)c2)CC1] | Yield: 39%; HPLC: 96.86%; LCMS: m/z = 394.2 [M + H]+; ¹HNMR (400 MHz, DMSO-d₆): δ 8.04 (d, J = 7.69 Hz, 1H), 7.71-7.59 (m, 1H), 7.38 (dd, J = 1.94, 8.34 Hz, 1H), 6.95 (d, J = 8.02 Hz, 1H), 6.25-6.01 (m, 2H), 5.58 (dd, J = 2.44, 9.93 Hz, 1H), 4.77 (p, J = 7.15 Hz, 1H), 3.97-3.71 (m, 3H), 3.34 (s, 1H), 2.90-2.74 (m, 2H), 1.72 (d, J = 12.40 Hz, 2H), 1.39 (d, J = 6.98 Hz, 3H), 1.34-1.14 (m, 2H). |

| Example | Structure | Yield (%) & Analytical Data |
|---|---|---|
| 13 | 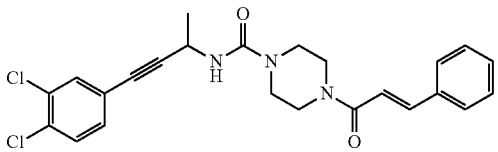 [SMILES: CC(C#Cc1ccc(Cl)c(Cl)c1)NC(=O)N1CCN(C(=O)/C=C/c2ccccc2)CC1] | Yield: 12%; HPLC: 96.5%; LCMS: m/z = 456.2 [M]+; $^1$HNMR (400 MHz, CDCl3): δ 7.72 (d, J = 15.33 Hz, 1H), 7.58-7.48 (m, 2H), 7.38 (td, J = 2.78, 5.06 Hz, 4H), 7.26-7.22 (m, 2H), 6.86 (d, J = 15.38 Hz, 1H), 6.73 (s, 1H), 5.05-4.89 (m, 1H), 3.63 (dd, J = 36.00, 104.04 Hz, 8H), 1.68-1.46 (m, 3H), |
| 14 | 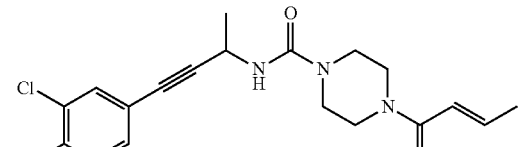 | Yield: 32%; HPLC: 98.3%; LCMS: m/z = 394.2 [M]$^+$; $^1$HNMR (400 MHz, CDCl$_3$): δ 7.51 (d, J = 1.91 Hz, 1H), 7.37 (d, J = 8.32 Hz, 1H), 7.27 (s, 3H), 7.23 (dd, J = 1.93, 8.30 Hz, 1H), 6.92 (dq, J = 6.84, 14.81 Hz, 1H), 6.25 (dq, J = 1.65, 14.98 Hz, 1H), 4.95 (p, J = 7.04 Hz, 1H), 4.66 (d, J = 7.85 Hz, 1H), 3.55 (dd, J = 42.76, 85.91 Hz, 8H), 1.51 (d, J = 6.86 Hz, 3H). |
| 15 | 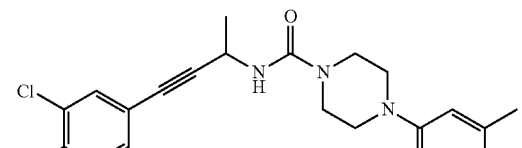 | Yield: 34.5%; HPLC: 96.07%; LCMS: m/z = 408.2[M]+; $^1$H NMR (400 MHz, CDCl$_3$): δ 7.51 (d, J = 1.91 Hz, 1H), 7.37 (d, J = 8.29 Hz, 1H), 7.28-7.19 (m, 1H), 5.78 (p, J = 1.40 Hz, 1H), 4.95 (p, J = 7.10 Hz, 1H), 4.65 (d, J = 7.88 Hz, 1H), 3.74-3.33 (m, 8H), 1.89 (dd, J = 1.36, 22.06 Hz, 6H), 1.51 (d, J = 6.87 Hz, 3H). |
| 16 | 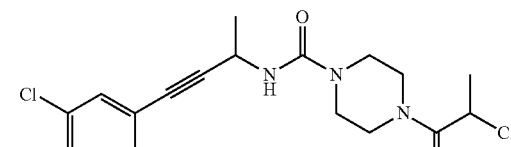 | Yield: 52%; HPLC: 95.7%; LCMS: m/z = 418.2 [M + 2]+; $^1$HNMR (400 MHz, CDCl$_3$): δ 7.51 (d, J = 1.91 Hz, 1H), 7.37 (d, J = 8.30 Hz, 1H), 7.23 (dd, J = 1.93, 8.34 Hz, 1H), 5.06-4.87 (m, 1H), 4.56 (q, J = 6.51 Hz, 1H), 3.90 (dt, J = 5.85, 8.27 Hz, 1H), 3.82-3.56 (m, 2H), 3.50 (td, J = 5.79, 9.40, 11.78 Hz, 4H), 3.33 (td, J = 5.53, 9.43 Hz, 1H), 1.69 (d, J = 6.54 Hz, 3H), 1.51 (d, J = 6.90 Hz, 3H). |
| 17 | 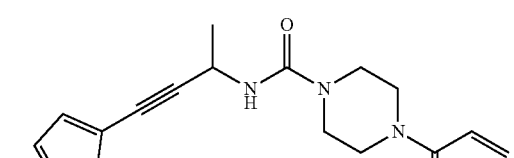 | Yield: 45.5%; HPLC: 94.98%; LCMS: m/z = 351.7 [M + H]+; $^1$H NMR (400 MHz, CDCl$_3$): δ 6.95 (d, J = 3.93 Hz, 1H), 6.84 (d, J = 3.94 Hz, 1H), 6.58 (dd, J = 10.53, 16.81 Hz, 1H), 6.32 (dd, J = 1.89, 16.85 Hz, 1H), 5.73 (dd, J = 1.88, 10.49 Hz, 1H), 5.33-5.29 (m, 1H), 4.11 (qd, J = 3.30, 6.73 Hz, 1H), 3.67 (d, J = 52.61 Hz, 4H), 3.45 (t, J = 5.22 Hz, 4H), 1.27 (d, J = 7.47 Hz, 3H). |
| 18 | 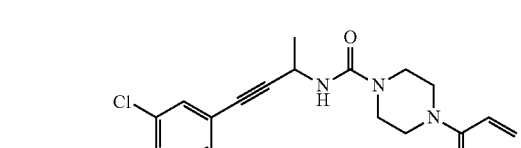 | Yield: 12.0%; HPLC: 95.1%; LCMS: m/z = 452.1[M + H]$^+$; $^1$HNMR (400 MHz, CDCl$_3$): δ 7.45-7.30 (m, 6H), 7.26 (d, J = 0.49 Hz, 1H), 6.87 (d, J = 8.48 Hz, 1H), 6.56 (dd, J = 10.47, 16.77 Hz, 1H), 6.33 (dd, J = 1.90, 16.80 Hz, 1H), 5.74 (dd, J = 1.87, 10.52 Hz, 1H), 5.16 (s, 2H), 5.00-4.89 (m, 1H), 4.64 (d, J = 7.74 Hz, 1H), 3.72-3.40 (m, 8H), 1.49 (d, J = 6.90 Hz, 3H) |

| Example | Structure | Yield (%) & Analytical Data |
|---------|-----------|------------------------------|
| 19 | 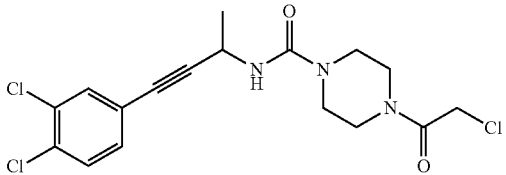 [SMILES: CC(C#Cc1ccc(Cl)c(Cl)c1)NC(=O)N1CCN(C(=O)CCl)CC1] | Yield: 52%; HPLC: 99.36%; LCMS: m/z = 404.2 [M + 2]+; $^1$H NMR (400 MHz, CDCl$_3$): δ 7.51 (d, J = 1.86 Hz, 1H), 7.38 (d, J = 8.33 Hz, 1H), 7.23 (dd, J = 1.91, 8.29 Hz, 1H), 4.95 (q, J = 7.15 Hz, 1H), 4.65 (d, J = 7.66 Hz, 1H), 4.09 (s, 2H), 3.68 (t, J = 5.44 Hz, 2H), 3.57 (s, 4H), 3.41 (t, J = 5.26 Hz, 2H), 1.51 (d, J = 6.82 Hz, 3H). |
| 20 | 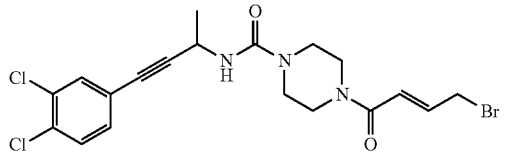 [SMILES: CC(C#Cc1ccc(Cl)c(Cl)c1)NC(=O)N1CCN(C(=O)/C=C/CBr)CC1] | Yield: Crude; LCMS: m/z = 474.1 [M + 1]$^+$; |
| 21 | 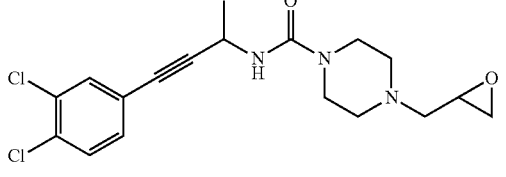 | Yield: 25.3%; HPLC: 98.8%; LCMS: m/z 382.1 [M]+; $^1$H NMR (400 MHz, CDCl3): δ 7.50 (d, J = 1.74 Hz, 1H), 7.39-7.33 (m, 1H), 7.25-7.20 (m, 1H), 5.13-4.85 (m, 1H), 4.63 (d, J = 7.79 Hz, 1H), 3.59-3.30 (m, 4H), 3.27-2.99 (m, 1H), 2.96-2.73 (m, 2H), 2.73-2.41 (m, 5H), 2.25 (dd, J = 7.05, 13.36 Hz, 1H), 1.62 (s, 2H), 1.62-1.48 (m, 3H). |
| 22 | 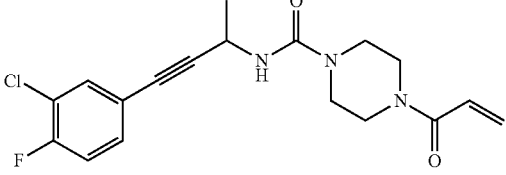 | Yield: 20%; HPLC: 95.6%; LCMS: m/z = 364.3 [M + H]+; $^1$H NMR (400 MHz, CDCl$_3$): δ 7.31 (t, J = 7.93 Hz, 1H), 7.26 (s, 1H), 7.18 (dd, J = 1.82, 9.63 Hz, 1H), 6.55 (dd, J = 10.48, 16.78 Hz, 1H), 6.33 (dd, J = 1.87, 16.75 Hz, 1H), 5.75 (dd, J = 1.85, 10.51 Hz, 1H), 5.02-4.84 (m, 1H), 3.87-3.25 (m, 8H), 1.65 (s, 2H), 1.50 (d, J = 6.87 Hz, 3H). |
| 23 | 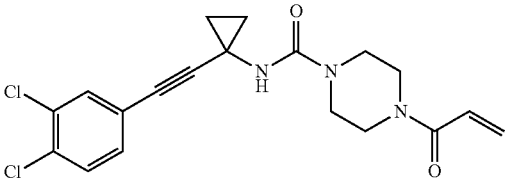 [SMILES: C=CC(=O)N1CCN(C(=O)NC2(C#Cc3ccc(Cl)c(Cl)c3)CC2)CC1] | Yield: 16.9%; HPLC: 97.7%; LCMS: m/z = 392.3 [M + H]+; $^1$H NMR (400 MHz, CDCl$_3$): δ 7.47 (d, J = 1.91 Hz, 1H), 7.32 (d, J = 8.33 Hz, 1H), 7.26 (s, 2H), 7.20 (dd, J = 1.92, 8.28 Hz, 1H), 6.55 (dd, J = 10.50, 16.79 Hz, 1H), 6.33 (dd, J = 1.90, 16.80 Hz, 1H), 5.74 (dd, J = 1.86, 10.49 Hz, 1H), 3.81-3.24 (m, 8H), 1.44-1.07 (m, 4H). |
| 24 | 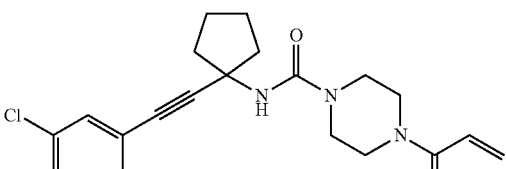 | Yield: 26.3%; HPLC: 98.3%; LCMS: m/z = 420.3; $^1$HNMR (400 MHz, CDCl$_3$): δ 7.50 (d, J = 1.96 Hz, 1H), 7.33 (d, J = 8.28 Hz, 1H), 7.22 (ddd, J = 0.75, 1.89, 8.33 Hz, 1H), 6.56 (dd, J = 10.45, 16.76 Hz, 1H), 6.33 (dd, J = 1.84, 16.84 Hz, 1H), 5.80-5.69 (m, 1H), 4.64 (s, 1H), 3.55 (dd, J = 50.76 94.30 Hz, 8H), 2.35-2.03 (m, 4H), 1.83 (tdd, J = 6.78, 11.23, 15.75 Hz, 4H). |

-continued

| Example | Structure | Yield (%) & Analytical Data |
|---|---|---|
| 25 | 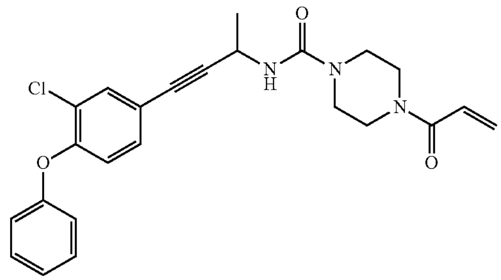 [SMILES: C=CC(=O)N1CCN(C(=O)NC(C)C#Cc2ccc(Oc3ccccc3)c(Cl)c2)CC1] | Yield: 78%; HPLC: 97.9%; LCMS: m/z = 438.05 [M + H]+; $^1$H NMR (400 MHz, CDCl3): δ 7.52 (d, J = 2.03 Hz, 1H), 7.40-7.31 (m, 2H), 7.26 (s, 1H), 7.19-7.09 (m, 1H), 7.02-6.94 (m, 2H), 6.85 (d, J = 8.49 Hz, 1H), 6.56 (dd, J = 10.48, 16.78 Hz, 1H), 6.34 (dd, J = 1.85, 16.75 Hz, 1H), 5.75 (dd, J = 1.86, 10.50 Hz, 1H), 4.95 (p, J = 6.99 Hz, 1H), 4.66 (d, J = 7.94 Hz, 1H), 3.84-3.29 (m, 8H), 1.54 (d, J = 24.85 Hz, 3H). |
| 26 | 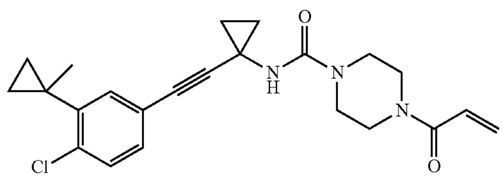 [SMILES: C=CC(=O)N1CCN(C(=O)NC2(C#Cc3ccc(Cl)c(C4(C)CC4)c3)CC2)CC1] | Yield: 31.8%; HPLC: 98.7%; LCMS: m/z = 412.2 [M + H]+; $^1$H NMR (400 MHz, CDCl3): δ 7.39 (d, J = 2.03 Hz, 1H), 7.20 (d, J = 8.29 Hz, 1H), 7.14 (dd, J = 2.03, 8.23 Hz, 1H), 6.55 (dd, J = 10.53, 16.78 Hz, 1H), 6.33 (dd, J = 1.84, 16.79 Hz, 1H), 5.74 (dd, J = 1.85, 10.50 Hz, 1H), 5.14 (s, 1H), 3.54 (dd, J = 53.25, 90.26 Hz, 8H), 1.38-1.32 (m, 2H), 1.30 (s, 3H), 1.21-1.13 (m, 2H), 0.82-0.70 (m, 4H). |
| 27 | 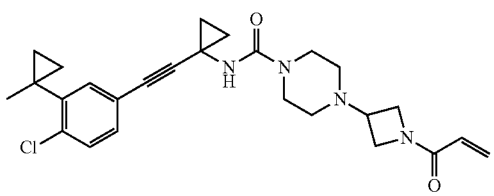 [SMILES: C=CC(=O)N1CC(N2CCN(C(=O)NC3(C#Cc4ccc(Cl)c(C5(C)CC5)c4)CC3)CC2)C1] | Yield: 8.3%; HPLC: 97.7%; LCMS: m/z = 467.4 [M + H]+; $^1$H NMR (400 MHz, CDCl3): δ 7.39 (d, J = 2.02 Hz, 1H), 7.19 (s, 1H), 7.14 (dd, J = 2.03, 8.25 Hz, 1H), 6.33 (dd, J = 1.86, 17.00 Hz, 1H), 6.18 (dd, J = 10.30, 16.97 Hz, 1H), 5.67 (dd, J = 1.88, 10.29 Hz, 1H), 5.10 (s, 1H), 4.33-3.84 (m, 4H), 3.42 (dddd, J = 5.99, 13.37, 16.66, 29.80 Hz, 4H), 3.19 (ddd, J = 5.35, 7.27, 12.40 Hz, 1H), 2.36 (q, J = 5.25 Hz, 4H), 1.46-1.09 (m, 7H), 0.99-0.59 (m, 4H). |
| 28 | 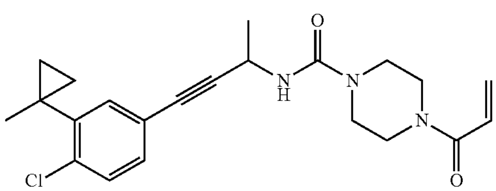 [SMILES: C=CC(=O)N1CCN(C(=O)NC(C)C#Cc2ccc(Cl)c(C3(C)CC3)c2)CC1] | Yield: 14.5%; HPLC: 94.4%; LCMS: m/z = 400.3 [M + H]+; $^1$H NMR (400 MHz, CDCl3): δ 7.41 (d, J = 2.12 Hz, 1H), 7.28-7.19 (m, 1H), 7.17 (dd, J = 2.08, 8.21 Hz, 1H), 6.56 (dd, J = 10.43, 16.80 Hz, 1H), 6.33 (dd, J = 1.84, 16.84 Hz, 1H), 5.75 (dd, J = 1.83, 10.48 Hz, 1H), 4.95 (p, J = 6.97 Hz, 1H), 4.67 (d, J = 7.88 Hz, 1H), 3.87-3.19 (m, 8H), 1.70-1.41 (m, 3H), 1.26 (d, J = 44.64 Hz, 3H), 0.97-0.54 (m, 4H). |
| 29 | 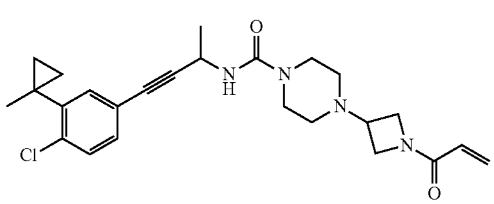 [SMILES: C=CC(=O)N1CC(N2CCN(C(=O)NC(C)C#Cc3ccc(Cl)c(C4(C)CC4)c3)CC2)C1] | Yield: 17%; HPLC: 90.7%; LCMS: m/z = 455.4 [M + H]+; $^1$H NMR (400 MHz, CDCl3): δ 7.40 (d, J = 2.05 Hz, 1H), 7.26 (s, 1H), 7.18 (d, J = 2.08 Hz, 1H), 6.33 (dd, J = 1.86, 17.02 Hz, 1H), 6.18 (dd, J = 10.29, 16.97 Hz, 1H), 5.68 (dd, J = 1.85, 10.28 Hz, 1H), 4.94 (p, J = 6.89 Hz, 1H), 4.64 (d, J = 7.80 Hz, 1H), 4.34-3.86 (m, 4H), 3.57-3.31 (m, 4H), 3.20 (tt, J = 5.18, 7.30 Hz, 1H), 2.38 (q, J = 4.74, 5.25 Hz, 4H), 1.49 (d, J = 6.87 Hz, 3H), 1.32 (s, 3H), 0.83-0.68 (m, 4H). |

-continued

| Example | Structure | Yield (%) & Analytical Data |
|---|---|---|
| 30 | 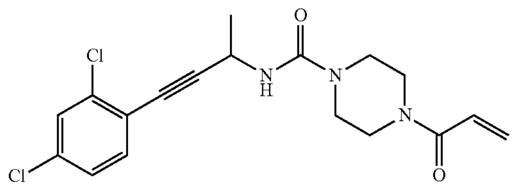 [SMILES: C=CC(=O)N1CCN(C(=O)NC(C)C#Cc2ccc(Cl)cc2Cl)CC1] | Yield: 40%; HPLC: 98.4%; LCMS: m/z = 379.8 [M + H]+; ¹H NMR (400 MHz, CDCl3): δ 7.40 (d, J = 2.08 Hz, 1H), 7.37 (d, J = 8.35 Hz, 1H), 7.19 (dd, J = 2.08, 8.36 Hz, 1H), 6.55 (dd, J = 10.51, 16.78 Hz, 1H), 6.33 (dd, J = 1.90, 16.80 Hz, 1H), 5.75 (dd, J = 1.85, 10.50 Hz, 1H), 5.16-4.79 (m, 1H), 4.71 (d, J = 7.82 Hz, 1H), 3.56 (dd, J = 46.85, 84.86 Hz, 8H), 1.74-1.30 (m, 3H). |
| 31 | 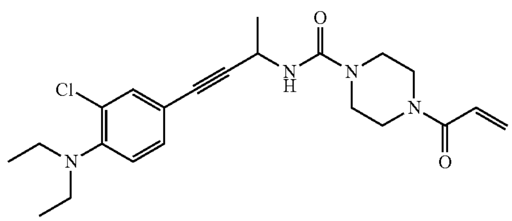 [SMILES: C=CC(=O)N1CCN(C(=O)NC(C)C#Cc2ccc(N(CC)CC)c(Cl)c2)CC1] | Yield: 57%; HPLC: 95%; LCMS: m/z = 417.3 [M + H]+; ¹H NMR (300 MHz, CDCl3): δ 7.42 (d, J = 1.97 Hz, 1H), 7.33-7.17 (m, 1H), 6.95 (d, J = 8.40 Hz, 1H), 6.56 (dd, J = 10.44, 16.77 Hz, 1H), 6.33 (dd, J = 1.97, 16.78 Hz, 1H), 5.74 (dd, J = 1.97, 10.41 Hz, 1H), 4.94 (p, J = 6.98 Hz, 1H), 3.56 (dd, J = 34.77, 64.76 Hz, 8H), 3.14 (q, J = 7.05 Hz, 6H), 1.49 (d, J = 6.82 Hz, 3H), 1.03 (t, J = 7.05 Hz, 4H). |
| 32 | 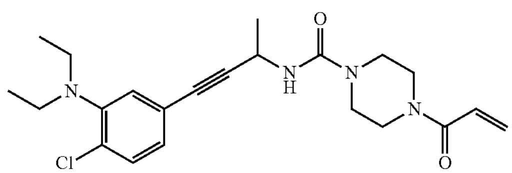 [SMILES: C=CC(=O)N1CCN(C(=O)NC(C)C#Cc2ccc(Cl)c(N(CC)CC)c2)CC1] | Yield: 30%; HPLC: 95.2%; LCMS: m/z = 417.4 [M + H]+; ¹H NMR (300 MHz, CDCl3): δ 7.42 (d, J = 1.97 Hz, 1H), 7.33-7.17 (m, 1H), 6.95 (d, J = 8.40 Hz, 1H), 6.56 (dd, J = 10.44, 16.77 Hz, 1H), 6.33 (dd, J = 1.97, 16.78 Hz, 1H), 5.74 (dd, J = 1.97, 10.41 Hz, 1H), 4.94 (p, J = 6.98 Hz, 1H), 3.56 (dd, J = 34.77, 64.76 Hz, 8H), 3.14 (q, J = 7.05 Hz, 6H), 1.49 (d, J = 6.82 Hz, 3H), 1.03 (t, J = 7.05 Hz, 4H). |
| 33 | 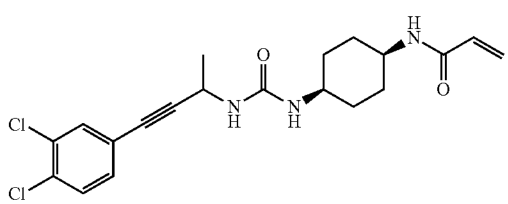 [SMILES: C=CC(=O)N[C@H]1CC[C@@H](NC(=O)NC(C)C#Cc2ccc(Cl)c(Cl)c2)CC1] | Yield: 82%; HPLC: 96.8%; LCMS: m/z = 408.2[M + H]+; ¹H NMR (400 MHz, DMSOd₆): δ 8.01-7.88 (m, 1H), 7.72-7.57 (m, 2H), 7.38 (dt, J = 1.67, 8.33 Hz, 1H), 6.36-6.19 (m, 2H), 6.06 (dt, J = 1.87, 17.10 Hz, 1H), 5.87 (d, J = 7.10 Hz, 1H), 5.55 (dt, J = 1.81, 10.17 Hz, 1H), 4.78-4.60 (m, 1H), 3.61 (d, J = 56.26 Hz, 2H), 1.50 (d, J = 31.22 Hz, 8H), 1.35 (dd, J = 1.40, 7.01 Hz, 3H). |
| 34 | 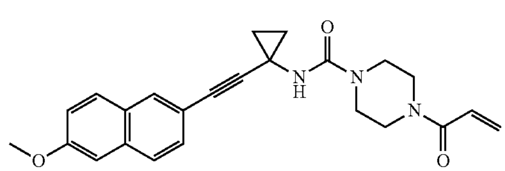 [SMILES: C=CC(=O)N1CCN(C(=O)NC2(C#Cc3ccc4cc(OC)ccc4c3)CC2)CC1] | Yield: 10%; HPLC. 96.87%; LCMS: m/z = 404.6 (M + H]; 1H NMR (400 MHz, Chloroform-d) δ 7.81 (d, J = 1.9 Hz, 1H), 7.69 (t, J = 8.7 Hz, 2H), 7.49 (dd, J = 8.4, 1.8 Hz, 1H), 7.15 (dd, J = 8.9, 2.5 Hz, 1H), 7.08 (d, J = 2.6 Hz, 1H), 6.33 (dd, J = 16.8, 10.3 Hz, 1H), 6.20 (dd, J = 16.8, 2.1 Hz, 1H), 5.83 (s, 1H), 5.65 (dd, J = 10.3, 2.1 Hz, 1H), 3.89 (s, 3H), 3.08 (d, J = 35.4 Hz, 4H), 2.78 (s, 2H), 2.47 (s, 2H), 1.05-1.02 (m, 2H), 1.00 (dd, J = 3.2, 1.8 Hz, 2H). |

-continued

| Example | Structure | Yield (%) & Analytical Data |
|---|---|---|
| 35 | 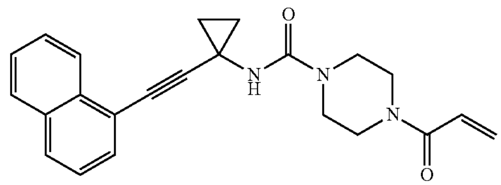 [SMILES: C=CC(=O)N1CCN(C(=O)NC2(C#Cc3cccc4ccccc34)CC2)CC1] | Yield: 9.5%; LCMS: m/z = 374 [M]+; HPLC: 92.65%; 1H NMR (400 MHz, Chloroform-d) δ 8.31-8.26 (m, 1H), 7.83-7.75 (m, 2H), 7.62 (dd, J = 7.2, 1.2 Hz, 1H), 7.57-7.45 (m, 2H), 7.37 (dd, J = 8.3, 7.2 Hz, 1H), 6.55 (dd, J = 16.8, 10.5 Hz, 1H), 6.33 (dd, J = 16.8, 1.9 Hz, 1H), 5.74 (dd, J = 10.5, 1.9 Hz, 1H), 5.24 (s, 1H), 3.74 (s, 2H), 3.60 (s, 2H), 3.53 (s, 2H), 3.40 (s, 2H), 1.48-1.44 (m, 2H), 1.29-1.24 (m, 2H). |
| 36 | 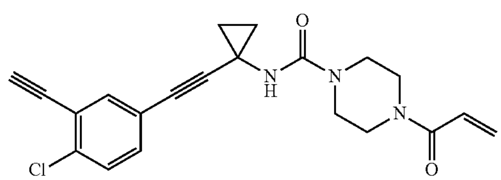 [SMILES: C#Cc1cc(C#CC2(NC(=O)N3CCN(C(=O)C=C)CC3)CC2)ccc1Cl] | Yield: 28%; HPLC: 95.14%; LCMS: m/z = 382.3[M + H]$^+$; $^1$H NMR (400 MHz, Chloroform-d) δ 7.55 (t, J = 1.2 Hz, 1H), 7.29 (d, J = 1.0 Hz, 2H), 6.55 (dd, J = 16.8, 10.5 Hz, 1H), 6.33 (dd, J = 16.8, 1.9 Hz, 1H), 5.76-5.72 (m, 1H), 5.13 (s, 1H), 3.72 (s, 2H), 3.60 (s, 2H), 3.50 (s, 2H), 3.35 (s, 3H), 1.37-1.32 (m, 2H), 1.21-1.16 (m, 2H). |
| 37 | 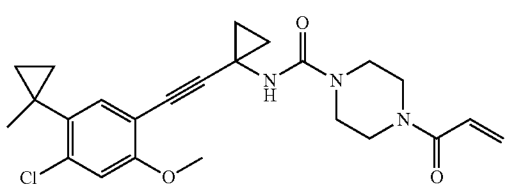 [SMILES: C=CC(=O)N1CCN(C(=O)NC2(C#Cc3cc(C4(C)CC4)c(Cl)cc3OC)CC2)CC1] | Yield: 3.6%; HPLC: 97.8%; LCMS: m/z = 442.3[M + H]$^+$; $^1$H NMR (400 MHz, Chloroform-d) δ 7.36 (s, 1H), 6.78 (s, 1H), 6.59-6.50 (m, 2H), 6.36-6.29 (m, 1H), 5.76-5.71 (m, 1H), 5.18 (s, 1H), 3.80 (s, 3H), 3.53-3.46 (m, 2H), , 3.71 (s, 2H), 3.58 (s, 2H), 3.36 (s, 2H), 1.41-1.35 (m, 2H), 1.27 (s, 3H), 1.22-1.16 (m, 2H), 0.78-0.66 (m, 4H). |
| 38 | 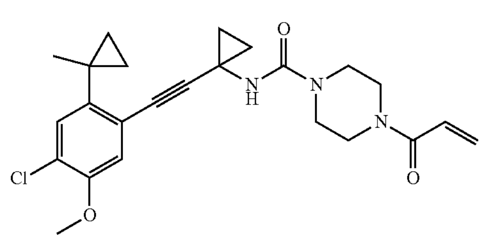 [SMILES: C=CC(=O)N1CCN(C(=O)NC2(C#Cc3cc(OC)c(Cl)cc3C3(C)CC3)CC2)CC1] | Yield: 6.5%; HPLC: 99%; LCMS: m/z = 442.3[M + H]$^+$; $^1$H NMR (400 MHz, Chloroform-d) δ 7.36 (s, 1H), 6.78 (s, 1H), 6.59-6.50 (m, 2H), 6.36-6.29 (m, 1H), 5.76-5.71 (m, 1H), 5.18 (s, 1H), 3.80 (s, 3H), 3.53-3.46 (m, 2H), , 3.71 (s, 2H), 3.58 (s, 2H), 3.36 (s, 2H), 1.41-1.35 (m, 2H), 1.27 (s, 3H), 1.22-1.16 (m, 2H), 0.78-0.66 (m, 4H). |

Example-39: 4-acryloyl-N-(1-((4-chloro-5-hydroxy-2-(1-methylcyclopropyl) phenyl)ethynyl)cyclopropyl) piperazine-1-carboxamide

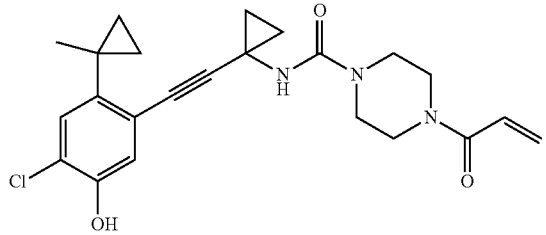 [SMILES: C=CC(=O)N1CCN(C(=O)NC2(C#Cc3cc(O)c(Cl)cc3C3(C)CC3)CC2)CC1]

To a stirred solution of Example 38 (0.050 g, 1.133 mmol) in DCM (20 ml) was added norbornadiene (2 drops) and BBr$_3$ (0.1 mL, 1.13 mmol) at −78° C. The reaction mixture was stirred at the same temperature for 2 h and then at 0° C. for 30 min. The reaction mixture was quenched with ice and the extracted with DCM. The organic layer was dried over Na$_2$SO$_4$ and concentrated. The crude product was purified by Preparative TLC method (Dichloromethane/Methanol=95/5) to afford the title compound (0.005 g, 10%). HPLC: 85.84%; LCMS: m/z=427.9[M]$^+$. $^1$H NMR (300 MHz, Chloroform-d) δ 7.26 (s, 1H), 7.14 (s, 1H), 7.03-7.00 (m, 1H), 6.58-6.49 (m, 1H), 6.36-6.30 (m, 1H), 5.75 (d, J=10.5 Hz, 1H), 5.48 (s, 1H), 3.73-3.42 (m, 8H), 1.62-1.18 (m, 5H), 0.72 (d, J=4.8 Hz, 2H), 0.57 (q, J=4.4 Hz, 2H).

Example-40: N-(4-(3-acetamido-4-chlorophenyl)but-3-yn-2-yl)-4-acryloylpiperazine-1-carboxamide (±)

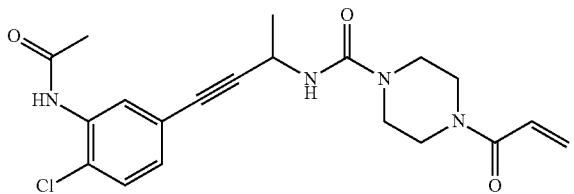 [SMILES: C=CC(=O)N1CCN(C(=O)NC(C)C#Cc2ccc(Cl)c(NC(C)=O)c2)CC1]

The title compound was synthesized from Intermediate 17ae as described in the procedure of example-1 to obtain the crude compound, which was further purified by preparative HPLC to afford the title compound. (Yield: 83.3%). HPLC: 96.9%; LCMS: m/z=403[M+H]$^+$; $^1$H NMR (400 MHz, CDCl$_3$): δ 8.46 (s, 1H), 7.55 (d, J=25.46 Hz, 1H), 7.35-7.21 (m, 1H), 7.08 (dd, J=1.92, 8.28 Hz, 1H), 6.72 (s, 1H), 6.56 (dd, J=10.51, 16.82 Hz, 1H), 6.33 (dd, J=1.83, 16.76 Hz, 1H), 5.74 (dd, J=1.87, 10.55 Hz, 1H), 5.07-4.82 (m, 1H), 3.85-3.28 (m, 8H), 2.25 (s, 3H) 1.49 (d, J=6.81 Hz, 3H)

Example-41: 4-acryloyl-N-(4-(4-chloro-3-(cyclopropanecarboxamido) phenyl)but-3-yn-2-yl) piperazine-1-carboxamide (±)

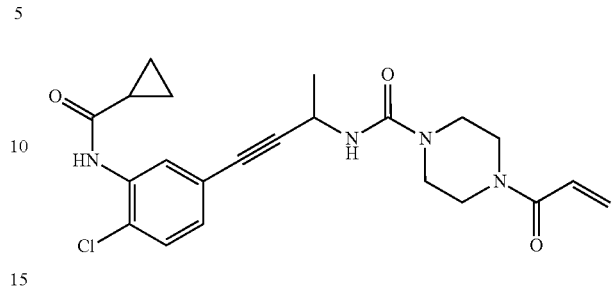

The title compound was synthesized from Intermediate 17af as described in the synthetic procedure of example-1 to obtain the crude compound, which was further purified by preparative HPLC to give title compound. Yield: 75.5%; HPLC: 99.25%; LCMS: m/z=429.3 [M+H]+; $^1$H NMR (400 MHz, CDCl$_3$): δ 8.49 (s, 1H), 7.82 (s, 1H), 7.26 (s, 1H), 7.06 (dd, J=2.00, 8.33 Hz, 1H), 6.56 (dd, J=10.49, 16.78 Hz, 1H), 6.33 (dd, J=1.88, 16.76 Hz, 1H), 5.74 (dd, J=1.86, 10.50 Hz, 1H), 4.92 (p, J=6.90 Hz, 1H), 4.72 (d, J=7.82 Hz, 1H), 3.85-3.32 (m, 8H), 1.47 (d, J=6.81 Hz, 3H), 1.38-1.18 (m, 1H), 1.18-0.81 (m, 4H).

Example-42: (E)-N-(4-(3,4-dichlorophenyl)but-3-yn-2-yl)-4-(4,4,4-trifluorobut-2-enoyl) piperazine-1-carboxamide(±)

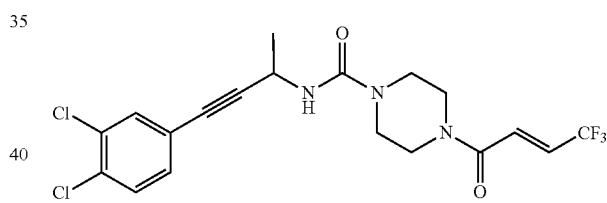

To a stirred solution of Intermediate 17 (0.150 g, 0.414 mmol) and (E)-4,4,4-trifluorobut-2-enoic acid (0.086 g, 0.624 mmol) in DMF (30 mL) was added (0.095 g, 0.496 mmol), HOBT (0.084 g, 0.629 mmol) and DIPEA (0.160 g, 1.24 mmol) at 10° C. and stirred for 16 h at RT. After completion of the reaction, the reaction mixture was poured into ice water and extracted with EtOAc. The EtOAc layer was dried over Na$_2$SO$_4$ and evaporated under reduced pressure and concentrated to obtain the crude and purified by prep TLC (hexanes/EtOAc=50/50) to afford the title compound (0.050 g, 27%). HPLC: 99.26%; LCMS: m/z=448.3 [M]+. $^1$H NMR (400 MHz, CDCl3): δ 7.50 (d, J=1.89 Hz, 1H), 7.37 (d, J=8.33 Hz, 1H), 7.22 (dd, J=1.96, 8.32 Hz, 1H), 6.95 (dq, J=1.96, 15.39 Hz, 1H), 6.82-6.70 (m, 1H), 5.02-4.83 (m, 1H), 4.67 (d, J=7.80 Hz, 1H), 3.82-3.31 (m, 8H), 1.50 (d, J=6.86 Hz, 3H).

The racemic compound obtained above was separated into two isomers (41a & 41b) by chiral prep HPLC method.

Column: lux amylose-2 (21.1 mm×250 mm), 5.0p, hexane and IPA:MeOH (80:20); Flow Rate: 20 mL/min, isocratic (85:15)

Example-42a: (E)-N-(4-(3,4-dichlorophenyl)but-3-yn-2-yl)-4-(4,4,4-trifluorobut-2-enoyl) piperazine-1-carboxamide (Isomer-1)

Yield=0.005 g, (33.3%). LCMS: m/z=449.2[M+H]$^+$; HPLC: 99.1%; Chiral HPLC: 95.2% (retention time=5.067 min).

Example-42b: (E)-N-(4-(3,4-dichlorophenyl)but-3-yn-2-yl)-4-(4,4,4-trifluorobut-2-enoyl) piperazine-1-carboxamide (Isomer-2)

Yield: 0.005 g, (33.3%). LCMS: m/z=449.2 [M+H]$^+$; HPLC: 95.7%; Chiral HPLC: 97.8% (retention time=5.138 min).

Example-43: N-(4-(3,4-dichlorophenyl) but-3-yn-2-yl)-4-methacryloylpiperazine-1-carboxamide (±)

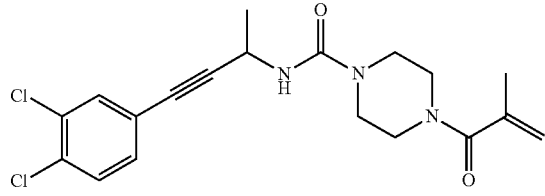 [SMILES: C=C(C)C(=O)N1CCN(C(=O)NC(C)C#Cc2ccc(Cl)c(Cl)c2)CC1]

To a stirred suspension of Intermediate 17 (0.150 g, 0.414 mmol) and methacrylic acid (42 μL, 59.832 mmol) in DCM (4.0 mL) were added EDCl (0.080 g, 0.414 mmol), HOBT (0.055 g, 0.414 mmol) and triethyl amine (0.23 mL, 1.654 mmol) at 0° C. and it was stirred at RT for 12 h. After completion of the reaction, it was poured into ice water and extracted with EtOAc. The combined EtOAc layers were washed with water and brine. Dried over Na$_2$SO$_4$ and evaporated under reduced pressure. The obtained residue was purified by using prep TLC plates (DCM/MeOH=97/3) to afford the title compound (0.072 g, 44.17%) as a solid. HPLC: 97.47%; LCMS: m/z=394.30[M]+$^1$. $^1$H NMR (400 MHz, CDCl$_3$): δ 7.53 (d, J=1.84 Hz, 1H), 7.39 (d, J=8.24 Hz, 1H), 7.32-7.20 (m, 1H), 5.26 (q, J=1.54 Hz, 1H), 5.08 (p, J=0.89 Hz, 1H), 4.97 (p, J=7.08 Hz, 1H), 4.69 (d, J=7.78 Hz, 1H), 3.65-3.45 (m, 8H), 1.99 (q, J=1.01 Hz, 3H), 1.53 (d, J=6.88 Hz, 3H).

Example-44: 4-(1-cyanocyclopropane-1-carbonyl)-N-(4-(3,4-dichlorophenyl)but-3-yn-2-yl) piperazine-1-carboxamide (±)

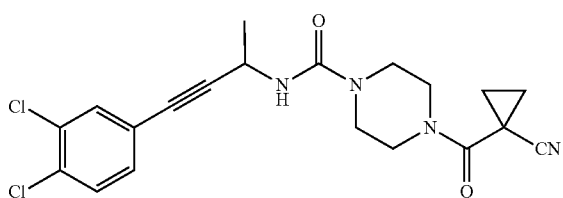 [SMILES: CC(C#Cc1ccc(Cl)c(Cl)c1)NC(=O)N1CCN(C(=O)C2(C#N)CC2)CC1]

The title compound was synthesized from Intermediate 17 and 1-cyanocyclopropane-1-carboxylic acid as described in the synthesis of Example-43. Yield: 25.8%; HPLC: 92.02%; LCMS: m/z=419.2 [M]$^+$; $^1$H NMR (400 MHz, CDCl$_3$): δ 7.52 (d, J=1.91 Hz, 1H), 7.38 (d, J=8.28 Hz, 1H), 7.24 (dd, J=1.95, 8.31 Hz, 1H), 5.06-4.84 (m, 1H), 4.68 (d, J=7.91 Hz, 1H), 3.88-3.48 (m, J=37.50 Hz, 8H), 2.18 (s, 2H), 1.52 (d, J=6.87 Hz, 3H), 1.33-1.19 (m, 2H).

Example-45: (E)-4-(2-cyano-4-methylpent-2-enoyl)-N-(1-((3,4-dichlorophenyl)ethynyl)cyclopropyl) piperazine-1-carboxamide

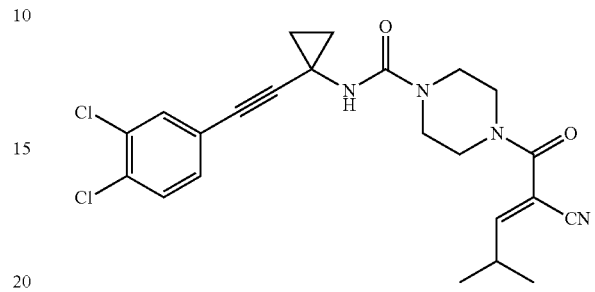

Step-1: 4-(2-cyanoacetyl)-N-(1-((3,4-dichlorophenyl)ethynyl)cyclopropyl) piperazine-1-carboxamide The title compound was synthesized from Intermediate 17o and 2-cyanoacetic acid as described in the synthesis of Example-43 or Example-44. Yield: 77.6%; LCMS: m/z=405.2 [M+H]$^+$.

Step-2: (E)-4-(2-cyano-4-methylpent-2-enoyl)-N-(1-((3,4-dichlorophenyl)ethynyl)cyclopropyl) piperazine-1-carboxamide To a stirred suspension of 4-(2-cyanoacetyl)-N-(1-((3,4-dichlorophenyl)ethynyl)cyclopropyl)piperazine-1-carboxamide (0.100 g, 246 mmol) in IPA (3 mL) were added isobutyraldehyde (0.022 g, 0.313 mmol), piperidine acetate (0.007 g, 0.049 mmol) at room temperature. After being stirred at room temperature for 5 h, the reaction mixture was concentrated under reduced pressure. The crude product purified by preparative TLC method (Dichloromethane/Metanol: 98/2) in two times run to obtain the title compound (0.020 g, 22.1%). HPLC: 96.8%; LCMS: m/z=459.3 [M]$^+$. $^1$H NMR (300 MHz, Chloroform-d): δ 7.47 (d, J=1.9 Hz, 1H), 7.35-7.30 (m, 1H), 7.23-7.17 (m, 1H), 6.99 (d, J=10.5 Hz, 1H), 5.13 (s, 1H), 3.64 (dd, J=6.5, 4.0 Hz, 4H), 3.47 (s, 4H), 1.39-1.31 (m, 1H), 1.23-1.17 (m, 2H), 1.15 (d, J=6.7 Hz, 6H), 1.07 (d, J=6.7 Hz, 2H).

Example-46: (E)-4-(2-cyano-3-cyclopropylacryloyl)-N-(1-((3,4-dichlorophenyl)ethynyl)cyclopropyl)piperazine-1-carboxamide

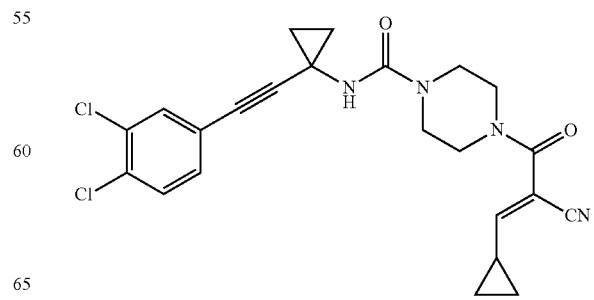

The title compound was synthesized from Step-1 intermediate of example-45 and cyclopropanecarbaldehyde as described in the synthesis step-2 of of Example-45. Yield: 25.85%; LCMS: m/z=457.4 [M]⁺; HPLC: 97.45%; ¹H NMR (400 MHz, Chloroform-d) δ 7.47 (d, J=1.8 Hz, 1H), 7.33 (d, J=8.3 Hz, 1H), 7.20 (dd, J=8.3, 1.9 Hz, 1H), 6.65 (d, J=11.3 Hz, 1H), 5.14 (s, 1H), 3.67 (s, 4H), 3.51-3.43 (m, 4H), 3.10-3.06 (m, 1H), 1.37-1.32 (m, 2H), 1.31-1.24 (m, 2H), 1.21-1.14 (m, 2H), 0.95-0.88 (m, 2H).

Example-47: (E)-N-(4-(3,4-dichlorophenyl)but-3-yn-2-yl)-4-(4-(dimethylamino)but-2-enoyl) piperazine-1-carboxamide (±)

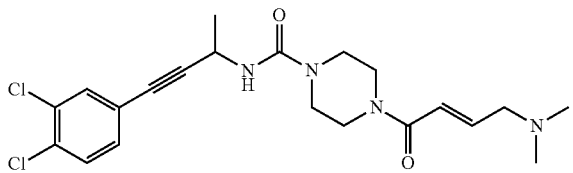 [SMILES: CC(C#Cc1ccc(Cl)c(Cl)c1)NC(=O)N1CCN(C(=O)/C=C/CN(C)C)CC1]

To a stirred solution of Example-20 (0.3 g, 0.709 mmol) in acetonitrile (25 mL), dimethylamine (2.0 M solution in THF) (3.5 mL, 7.09 mmol) was added at room temperature. After being stirred at room temperature for 16 h, the reaction mixture was concentrated under reduced pressure. The crude product purified by preparative HPLC to obtain the title compound (0.050 g, 54%). HPLC: 99.3%; LCMS: m/z=437.4 [M]⁺; ¹H NMR (400 MHz, DMSOd₆) δ 7.66 (d, J=1.96 Hz, 1H), 7.37 (dd, J=1.98, 8.37 Hz, 1H), 7.04 (d, J=7.94 Hz, 1H), 6.60 (d, J=2.32 Hz, 2H), 4.77 (p, J=7.13 Hz, 1H), 3.55-3.45 (m, 8H), 3.32 (s, 1H), 3.12-2.93 (m, 2H), 2.13 (s, 6H), 1.39 (d, J=6.99 Hz, 3H).

Example-48a: Trans-N-((1S,2S)-2-(3-(4-(3,4-dichlorophenyl)but-3-yn-2-yl)-1-methylureido) cyclohexyl)-N-methyl acrylamide (±) (Isomer-1)

To a stirred suspension of 3-(4-(3,4-dichlorophenyl)but-3-yn-2-yl)-1-methyl-1-(2-(methyl amino) cyclohexyl) urea (Intermediate 17ag) (0.060 g, 0.157 mmol) in DCM (5 mL) was added triethylamine (65 µL, 0.470 mmol) and acryloyl chloride (14 µL, 0.172 mmol) at 0° C. The reaction mixture was allowed to warm to RT for 2 h. The reaction mixture was extracted with DCM, the combined DCM layers were washed with water and brine; dried over Na₂SO₄ and evaporated under reduced pressure. The crude compound obtained (mixture of Isomers by TLC) was purified by preparative TLC (dichloromethane/methanol=99/1) to afford separated isomers 48a and 48b.

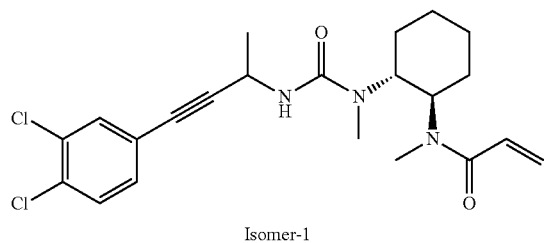 [SMILES: C=CC(=O)N(C)[C@@H]1CCCC[C@H]1N(C)C(=O)NC(C)C#Cc1ccc(Cl)c(Cl)c1]

Isomer-1

Example-48b: Trans N-((1S,2S)-2-(3-(4-(3,4-dichlorophenyl) but-3-yn-2-yl)-1-methylureido) cyclohexyl)-N-methyl acrylamide (±)(Isomer-2)

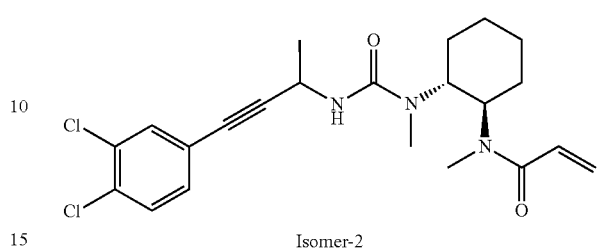

Isomer-2

Example-48a: Yield: 0.010 g, 14.70%; HPLC: 97.47%; chiral HPLC: 4.36 peak 1, 7.74 peak 2; LCMS: m/z=436.4 [M+H]⁺¹; ¹H NMR (300 MHz, CDCl₃): δ 7.47 (d, J=1.92 Hz, 1H), 7.37 (d, J=8.31 Hz, 1H), 7.26-7.21 (m, 1H), 6.45 (dd, J=10.44, 16.82 Hz, 1H), 6.20 (dd, J=2.12, 16.91 Hz, 1H), 5.59-5.46 (m, 1H), 4.86 (p, J=7.12 Hz, 1H), 4.67-4.42 (m, 2H), 2.88 (d, J=10.39 Hz, 3H), 2.69 (s, 3H), 1.79 (d, J=9.66 Hz, 4H), 1.59-1.35 (m, 7H).

Example-48b: Yield: 0.008 g, 11.76%; HPLC 96.80%; chiral HPLC: 5.90 peak 1, 8.57 peak 2; LCMS: m/z=436.4 [M+H]⁺¹; ¹H NMR (300 MHz, CDCl₃): δ 7.49 (d, J=1.95 Hz, 1H), 7.36 (d, J=8.34 Hz, 1H), 7.26-7.20 (m, 1H), 6.54 (dd, J=10.38, 16.80 Hz, 1H), 6.25 (dd, J=2.11, 16.79 Hz, 1H), 5.66 (d, J=10.40 Hz, 1H), 4.96-4.78 (m, 1H), 4.70-4.31 (m, 2H), 2.88 (d, J=17.49 Hz, 3H), 2.70 (s, 3H), 1.79 (d, J=8.71 Hz, 4H), 1.58-1.24 (m, 7H).

Example-49: N-(4-(3,4-dichlorophenyl)but-3-yn-2-yl)-4-(vinylsulfonamido) piperidine-1-carboxamide (±)

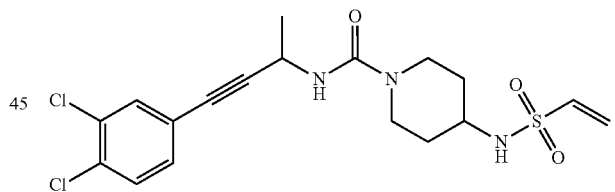

To a stirred solution of Intermediate 17k (0.1 g, 0.269 mmol) in dichloromethane (5 mL) was added chloroethyl sulfonylchloride (0.03 mL, 0.292 mmol) and triethylamine (0.111 mL, 0.807 mmol) at 10° C. After stirring 1 hour at ambient temperature, the reaction mixture washed with saturated sodium bicarbonate solution. The dichloromethane layer was dried and concentrated. The crude compound was purified by preparative HPLC to afford the title compound (0.020 g, 17%).

Method: Column: Xbridge-C-18 (19×150) mm; Water: Acetonitrile; Flowrate 15 mL/min. HPLC: 98.27%, LCMS: m/z=429.9 [M+H]+. ¹H NMR (400 MHz, DMSOd₆): δ 7.75-7.49 (m, 2H), 7.47-7.29 (m, 2H), 6.93 (d, J=8.18 Hz, 1H), 6.76 (ddd, J=0.86, 9.94, 16.52 Hz, 1H), 6.11-5.86 (m, 2H), 4.75 (p, J=7.13 Hz, 1H), 3.94-3.72 (m, 2H), 3.17 (tdd, J=4.73, 7.05, 8.84, 10.58 Hz, 2H), 2.78 (ddt, J=5.89, 11.88, 15.23 Hz, 2H), 1.74 (d, J=12.57 Hz, 2H), 1.34-1.22 (m, 3H).

Example-50: N-((1s, 4s)-4-(3-(4-(3,4-dichlorophenyl)but-3-yn-2-yl)ureido)cyclohexyl) ethenesulfonamide (±)

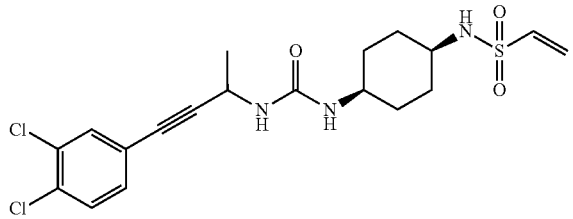 [SMILES: C=CS(=O)(=O)N[C@H]1CC[C@@H](NC(=O)NC(C)C#Cc2ccc(Cl)c(Cl)c2)CC1]

The title compound was synthesized from Intermediate 17y as per described in the synthesis of Example 49. Yield: 27%, LCMS: m/z=444.2 [M+H]$^+$; HPLC=98.84%. $^1$H NMR (400 MHz, DMSO$_6$): δ 7.71-7.58 (m, 2H), 7.38 (dd, J=1.99, 8.35 Hz, 1H), 7.27 (d, J=5.96 Hz, 1H), 6.70 (dd, J=9.91, 16.52 Hz, 1H), 6.26 (d, J=8.25 Hz, 1H), 6.07-5.90 (m, 2H), 5.85 (d, J=7.40 Hz, 1H), 4.74-4.57 (m, 1H), 3.49 (s, 1H), 3.18-2.99 (m, 1H), 1.50 (s, 8H), 1.34 (d, J=6.90 Hz, 3H).

Example-51: N-(1-((3,4-dichlorophenyl)ethynyl)cyclopropyl)-4-(vinylsulfonyl) piperazine-1-carboxamide

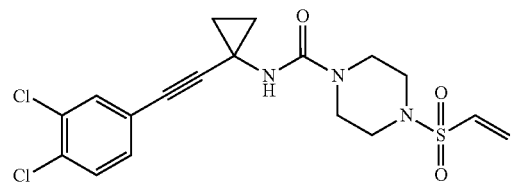 [SMILES: C=CS(=O)(=O)N1CCN(C(=O)NC2(C#Cc3ccc(Cl)c(Cl)c3)CC2)CC1]

The title compound was synthesized from Intermediate 17o as per described in the synthesis of example 49. Yield: 43.8%, LCMS: m/z=427.8 [M−H]$^+$; HPLC=98.75%. $^1$H NMR (300 MHz, Chloroform-d) δ 7.47 (dd, J=2.0, 1.0 Hz, 1H), 7.33 (dd, J=8.3, 1.0 Hz, 1H), 7.22-7.17 (m, 1H), 6.41 (ddd, J=16.6, 9.6, 1.0 Hz, 1H), 6.27 (dd, J=16.6, 1.0 Hz, 1H), 6.08 (dd, J=9.7, 1.0 Hz, 1H), 5.13 (s, 1H), 3.48 (t, J=5.1 Hz, 4H), 3.16 (t, J=5.1 Hz, 4H), 1.38-1.31 (m, 2H), 1.19-1.12 (m, 2H).

Example-52: 4-acryloyl-N-(4-(3,4-dichlorophenyl)but-3-yn-2-yl)-3-oxopiperazine-1-carboxamide (±)

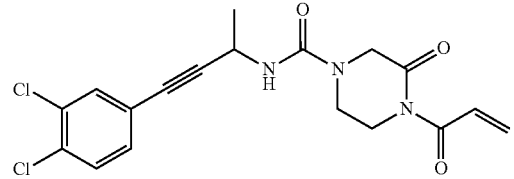 [SMILES: C=CC(=O)N1CCN(C(=O)NC(C)C#Cc2ccc(Cl)c(Cl)c2)CC1=O]

To a stirred solution of Intermediate 15f (0.1 g, 0.29 mmol) in THF (50 mL) added LiCl (0.016 g, 0.382 mmol), (Et)$_3$N (0.05 mL, 0.382 mmol) followed by acrylic anhydride (0.05 g, 0.382 mmol). The reaction mixture was stirred at room temperature for 16 h. The reaction mixture was poured into water and extracted with EtOAc (50 mL). The organic phase was dried over Na$_2$SO$_4$ and concentrated under reduced pressure. The crude compound was purified by silica prep-TLC mobile phase—2% methanol in dichloromethane. 0.02 g (17%), HPLC: 93.98%; LCMS: m/z=m/z=444.2 [M+H]$^{+1}$; H$^1$ NMR (300 MHz, CDCl$_3$): δ 7.50 (d, J=1.92 Hz, 1H), 7.37 (d, J=8.32 Hz, 1H), 7.23 (dd, J=1.97, 8.28 Hz, 1H), 7.19-7.10 (m, 1H), 6.46 (dd, J=1.68, 16.92 Hz, 1H), 5.85 (dd, J=1.68, 10.41 Hz, 1H), 5.07-4.82 (m, 1H), 4.63 (d, J=7.94 Hz, 1H), 4.28 (s, 2H), 4.01 (ddd, J=1.98, 4.41, 5.29 Hz, 2H), 3.77-3.48 (m, 2H), 1.51 (d, J=6.89 Hz, 3H).

Example-53: N-(2-(3-(4-(3,4-dichlorophenyl) but-3-yn-2-yl)-1-methylureido)ethyl) acrylamide

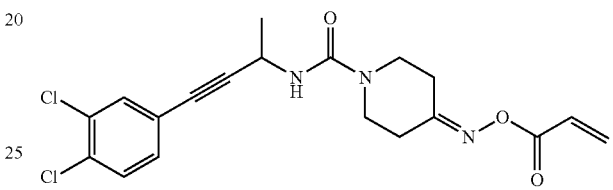

To a stirred suspension of N-(4-(3,4-dichlorophenyl) but-3-yn-2-yl)-4-(hydroxyimino) piperidine-1-carboxamide (Intermediate 15s) (0.090 g, 0.254 mmol) in DCM (3 mL) was added triethylamine (70 μL, 0.508 mmol) and acryloyl chloride (20 μL, 0.191 mmol) at 0° C. The reaction mixture was allowed to warm to RT and stirred for 2 h. The reaction mixture was poured in to ice water, extracted with DCM, the combined DCM layers were washed with brine, water; dried over Na$_2$SO$_4$ and evaporated under reduced pressure. The crude compound obtained was purified by (repeated 2 times) preparative TLC (dichloromethane/methanol=95/05) to afford the title compound (0.010 g, 9.70%). HPLC: 90.18%; LCMS: m/z=408.1 [M+H]$^+$; $^1$H NMR (400 MHz, CDCl$_3$): δ 7.50 (d, J=1.87 Hz, 1H), 7.37 (d, J=8.34 Hz, 1H), 7.22 (dd, J=1.93, 8.26 Hz, 1H), 6.54 (dd, J=1.24, 17.32 Hz, 1H), 6.20 (dd, J=10.57, 17.31 Hz, 1H), 5.95 (dd, J=1.24, 10.56 Hz, 1H), 4.95 (p, J=7.00 Hz, 1H), 4.69 (d, J=7.87 Hz, 1H), 3.59 (ddt, J=6.11, 13.01, 19.09 Hz, 4H), 2.85-2.59 (m, 4H), 1.50 (d, J=6.84 Hz, 3H).

Example-54: (E)-4-acryloyl-N'-cyano-N-(4-(3,4-dichlorophenyl)but-3-yn-2-yl) piperazine-carboximidamide (±)

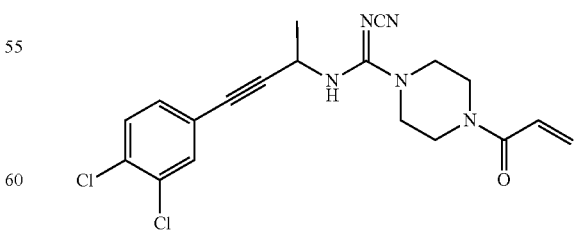

To a solution of Intermediate 13 (0.3 g, 0.83 mmol) and 1-(piperazin-1-yl) prop-2-en-1-one (Intermediate 6a) (0.275 g, 1.08 mmol) in DMSO (10 mL) was added triethylamine (0.346 mL, 2.49 mmol) at RT and stirred at 90° C. for 16 h.

After completion of reaction, the reaction mixture poured into ice water (20 mL), resulting solid was filtered and purified by Combiflash® column on silica gel (dichloromethane/methanol=95/5) to afford the title compound (0.05 g, 14.7%). LCMS: m/z 404.0 [M]+; 1H NMR (400 MHz, CDCl₃): δ 7.45 (d, J=1.89 Hz, 1H), 7.34 (d, J=8.30 Hz, 1H), 7.23-7.16 (m, 1H), 6.48 (dd, J=10.42, 16.77 Hz, 1H), 6.30 (dd, J=1.80, 16.72 Hz, 1H), 5.73 (dd, J=1.84, 10.44 Hz, 1H), 4.95-4.80 (m, 2H), 3.88-3.40 (m, 8H), 1.56-1.54 (m, 3H).

The following examples were prepared essentially by the method described in example-54 with appropriate variations in reactants, reagents and reaction conditions.

| Example | Structure | Yield & Analytical Data |
| --- | --- | --- |
| 55 | 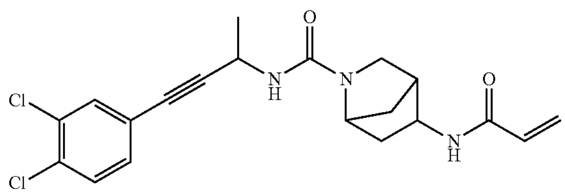 [SMILES: C=CC(=O)NC1CC2CC1CN2C(=O)NC(C)C#Cc1ccc(Cl)c(Cl)c1] | Yield: 55%; HPLC: 97.61%; LCMS: m/z = 406.2[M]+; 1H NMR (400 MHz, DMSOd₆) δ 8.36-8.17 (m, 1H), 7.72-7.50 (m, 2H), 7.34 (ddd, J = 1.95, 4.86, 8.25 Hz, 1H), 6.59 (m, 1H), 6.41-5.92 (m, 2H), 5.53 (dt, J = 2.36, 10.10 Hz, 1H), 4.89-4.62 (m, 1H), 4.24-3.92 (m, 2H), 3.17-2.92 (m, 2H), 2.65 (d, J = 8.58 Hz, 1H), 2.12-1.83 (m, 1H), 1.54 (s, 2H), 1.41-1.19 (m, 4H). |
| 56 | 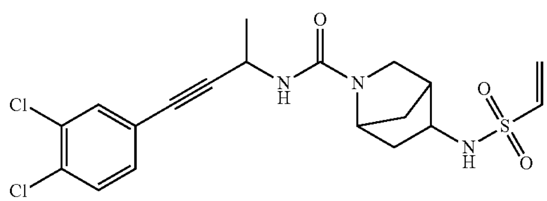 [SMILES: C=CS(=O)(=O)NC1CC2CC1CN2C(=O)NC(C)C#Cc1ccc(Cl)c(Cl)c1] | Yield: 30%; HPLC: 95.17%; LCMS: m/z = 442.3[M]+; 1H NMR (400 MHz, DMSOd₆): δ 7.71-7.52 (m, 2H), 7.46-7.28 (m, 1H), 6.77-6.47 (m, 2H), 6.16-5.87 (m, 1H), 4.76 (s, 1H), 4.10 (d, J = 6.23 Hz, 1H), 3.59-3.11 (m, 5H), 2.49 (dt, J = 2.01, 3.56 Hz, 2H), 2.00-1.93(m, 1H), 1.54-1.46 (m, 2H), 1.36 (dd, J = 8.88, 15.19 Hz, 3H). |
| 57 | 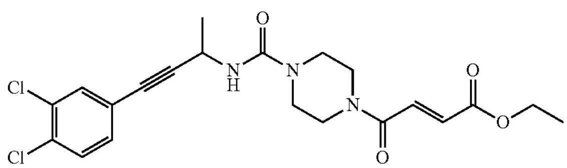 [SMILES: CCOC(=O)/C=C/C(=O)N1CCN(C(=O)NC(C)C#Cc2ccc(Cl)c(Cl)c2)CC1] | Yield: 42 4%; HPLC: 98.70%; LCMS: m/z = 452.2 [M + H]+; 1H NMR (400 MHz, DMSOd6): δ 7.66 (d, J = 1.91 Hz, 1H), 7.62 (d, J = 8.24 Hz, 1H), 7.46 (d, J = 15.39 Hz, 1H), 7.40-7.34 (m, 1H), 7.07 (d, J = 7.91 Hz, 1H), 6.56 (dd, J = 0.80, 15.43 Hz, 1H), 4.78 (q, J = 7.30 Hz, 1H), 4.27-4.08 (m, 2H), 3.52 (dt, J = 5.21, 10.45 Hz, 4H), 3.33 (d, J = 0.75 Hz, 4H), 1.39 (d, J = 6.96 Hz, 3H), 1.24 (td, J = 0.81, 7.14 Hz, 3H). |
| 58 | 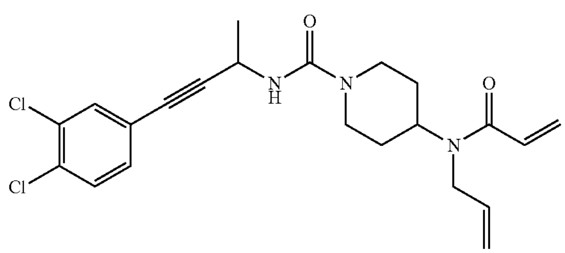 [SMILES: C=CCN(C(=O)C=C)C1CCN(C(=O)NC(C)C#Cc2ccc(Cl)c(Cl)c2)CC1] | Yield: 15.8%; HPLC: 98.9%; LCMS: m/z = 434.2[M]+; 1H NMR (400 MHz, CDCl₃): δ 7.52 (d, J = 1.90 Hz, 1H), 7.39 (d, J = 8.30 Hz, 1H), 7.29-7.23 (m, 1H), 6.51-6.35 (m, 2H), 5.92-5.77 (m, 1H), 5.71 (dd, J = 3.20, 9.27 Hz, 1H), 5.22 (dd, J = 13.80, 20.35 Hz, 2H), 5.04-4.87 (m, 1H), 4.83-4.60 (m, 2H), 4.18-3.97 (m, 2H), 3.91 (d, J = 4.31 Hz, 2H), 2.92 (t, J = 12.83 Hz, 2H), 1.84-1.69 (m, 2H), 1.69-1.56 (m, 2H), 1.51 (d, J = 6.86 Hz, 3H). |
| 59 | 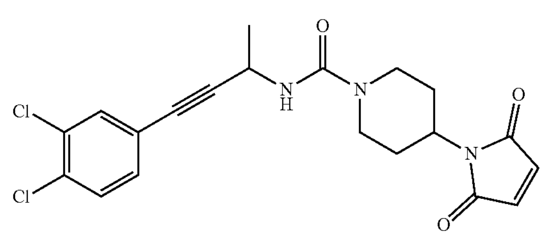 [SMILES: CC(C#Cc1ccc(Cl)c(Cl)c1)NC(=O)N1CCC(N2C(=O)C=CC2=O)CC1] | Yield: 55%; HPLC: 99.06%; LCMS: m/z = 420.3[M]+; 1H NMR (400 MHz, DMSOd₆) δ 7.67 (d, J = 1.94 Hz, 1H), 7.62 (d, J = 8.35 Hz, 1H), 7.38 (dd, J = 1.97, 8.31 Hz, 1H), 6.97 (s, 3H), 4.87-4.68 (m, 1H), 4.16-3.86 (m, 3H), 2.82-2.61 (m, 2H), 2.08-1.83 (m, 2H), 1.56 (d, J = 12.78 Hz, 2H), 1.39 (d, J = 6.98 Hz, 3H). |

| Example | Structure | Yield & Analytical Data |
|---|---|---|
| 60 | 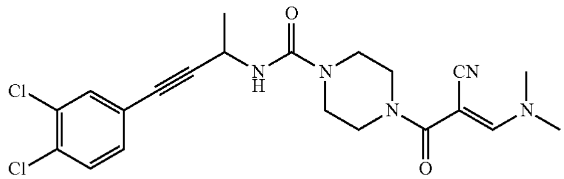 [SMILES: CC(C#Cc1ccc(Cl)c(Cl)c1)NC(=O)N1CCN(C(=O)/C(C#N)=C/N(C)C)CC1] | Yield: 54.54%; HPLC: 97.99%; LCMS: m/z = 448.35 [M + H]$^+$; $^1$H NMR (300 MHz, CDCl$_3$) δ 7.57 (s, 1H), 7.51 (d, J = 1.76 Hz, 1H), 7.37 (d, J = 8.32 Hz, 1H), 7.30-7.20 (m, 1H), 4.94 (d, J = 7.05 Hz, 1H), 4.66 (s, 1H), 3.66 (dd, J = 3.73, 6.73 Hz, 4H), 3.47 (dd, J = 3.88, 6.55 Hz, 4H), 3.36 (s, 3H), 3.19 (s, 3H), (Dimethyl in other Isomer), 2.66-2.60 (m, 6H), 1.50 (d, J = 6.87 Hz, 3H). |
| 61 | 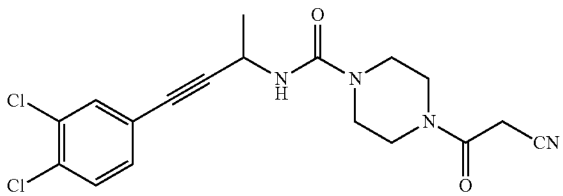 [SMILES: CC(C#Cc1ccc(Cl)c(Cl)c1)NC(=O)N1CCN(C(=O)CC#N)CC1] | Yield: 34.01%; HPLC: 98.34%; LCMS: m/z = 393.27 [M + H]$^+$; $^1$H NMR (400 MHz, CDCl$_3$) δ 6.95 (s, 1H), 6.83-6.81 (m, 1 H), 6.68-6.66 (m, 1H), 4.41-4.37(m, 1H), 4.13-4.07(m, 1H), 3.16-3.13 (m, 2H), 3.03-2.96 (m, 6H), 2.88-2.85 (m, 2H), 9.66 (d, J = 17.61 Hz, 3H). |
| 62 | 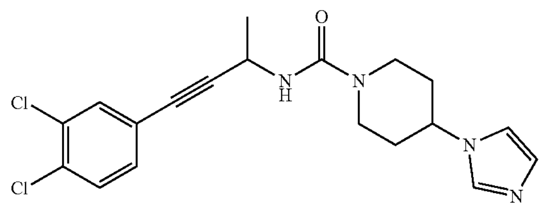 [SMILES: CC(C#Cc1ccc(Cl)c(Cl)c1)NC(=O)N1CCC(n2ccnc2)CC1] | Yield: 32.05%; HPLC: 99.24%; LCMS: m/z = 391.30[M]$^+$; $^1$H NMR (400 MHz, CDCl$_3$): δ 7.70-7.55 (m, 1H), 7.47 (d, J = 1.90 Hz, 1H), 7.34 (d, J = 8.28 Hz, 1H), 7.27-7.16 (m, 1H), 7.20-7.00 (m, 2H), 4.98-4.88 (m, 1H), 4.72 (d, J = 7.86 Hz, 1H), 4.12 (d, J = 11.72 Hz, 3H), 2.99-2.86 (m, 2H), 2.10 (d, J = 12.44 Hz, 2H), 1.94-1.80 (m, 2H), 1.48 (d, J = 6.86 Hz, 3H). |
| 63 | 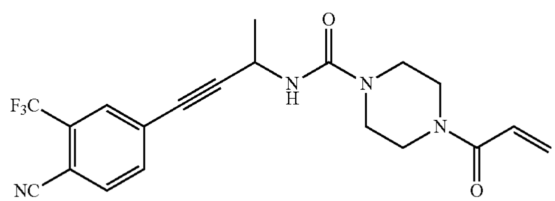 [SMILES: C=CC(=O)N1CCN(C(=O)NC(C)C#Cc2ccc(C#N)c(C(F)(F)F)c2)CC1] | Yield: 26.78%; HPLC: 98.26%; LCMS: m/z = 405.2 [M + H]$^+$. $^1$H NMR (400 MHz, CDCl$_3$): δ 7.84-7.73 (m, 2H), 7.71-7.64 (m, 1H), 6.55 (dd, J = 10.47, 16.81 Hz, 1H), 6.34 (dd, J = 1.80, 16.84 Hz, 1H), 5.75 (dd, J = 1.76, 10.55 Hz, 1H), 4.99 (p, J = 7.13 Hz, 1H), 4.65 (d, J = 7.86 Hz, 1H), 3.57 (dd, J = 48.36, 85.73 Hz, 8H), 1.52 (d, J = 20.12 Hz, 3H). |
| 64 | 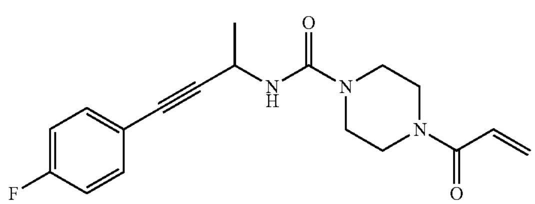 [SMILES: C=CC(=O)N1CCN(C(=O)NC(C)C#Cc2ccc(F)cc2)CC1] | Yield: 50.74%; HPLC: 98.69%; LCMS: m/z = 330.2 [M + H]$^+$; $^1$H NMR (300 MHz, CDCl$_3$): δ 7.44-7.35 (m, 2H), 7.04-6.94 (m, 2H), 6.56 (dd, J = 10.43, 16.76 Hz, 1H), 6.33 (dd, J = 1.94, 16.79 Hz, 1H), 5.75 (dd, J = 1.93, 10.42 Hz, 1H), 4.95 (p, J = 6.94 Hz, 1H), 4.68 (d, J = 7.80 Hz, 1H), 3.73-3.40 (m, 8H), 1.49 (d, J = 20.12 Hz, 3H). |

Example-65: (E)-4-(4-amino-4-oxobut-2-enoyl)-N-(4-(3,4-dichlorophenyl)but-3-yn-2-yl) piperazine-1-carboxamide (±)

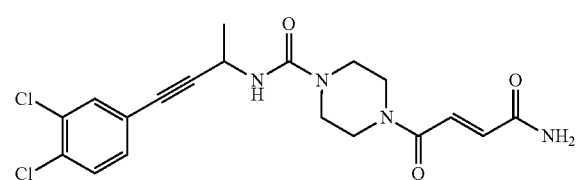 [SMILES: CC(C#Cc1ccc(Cl)c(Cl)c1)NC(=O)N1CCN(C(=O)/C=C/C(N)=O)CC1]

Step-1: Preparation of (E)-4-(4-((4-(3,4-dichlorophenyl)but-3-yn-2-yl)carbamoyl) piperazin-1-yl)-4-oxobut-2-enoic acid (±)

To a stirred solution of Example 57 (0.200 g, 0.440 mmol) in THF:MeOH:H$_2$O (1:1:8) mixture, LiOH.H$_2$O (0.093 g, 2.220 mmol) was added and stirred for 12 h at RT. The reaction mixture was concentrated under reduced pressure, diluted with water (25 mL) and washed with diethyl ether (2×50 mL). The aqueous layer was separated and P$^H$ was adjusted to slightly acidic with dil. HCl and extracted with EtOAc (50 mL). The organic layer was dried over anhydrous Na$_2$SO$_4$; concentrated under reduced pressure to obtain off white solid (0.08 g, 42.6%). LCMS: m/z 456.2 [M+H+38]$^+$.

Step-2: Preparation of (E)-4-(4-amino-4-oxobut-2-enoyl)-N-(4-(3,4-dichlorophenyl)but-3-yn-2-yl) piperazine-1-carboxamide (±)

The title compound was synthesized as per described procedure of Example-42 from intermediate from step-1 and ammonium chloride using EDC.HCl and HOBt in presence of Et₃N in DMF. Yield: 18.7%; HPLC: 98.4%; LCMS: m/z=423.0 [M]⁺; ¹H NMR (400 MHz, DMSOd₆) δ 7.66 (d, J=1.96 Hz, 1H), 7.62 (d, J=8.38 Hz, 1H), 7.41-7.35 (m, 1H), 7.25 (d, J=15.06 Hz, 1H), 6.78 (d, J=15.09 Hz, 1H), 4.77 (p, J=7.17 Hz, 1H), 3.61-3.44 (m, 4H), 3.33-3.17 (m, 4H), 3.18 (s, 1H), 1.24 (d, J=17.61 Hz, 3H),

Example-66: (E)-N-(1-((3,4-dichlorophenyl)ethynyl)cyclopropyl)-4-(4,4,4-trifluorobut-2-enoyl) piperazine-1-carboxamide

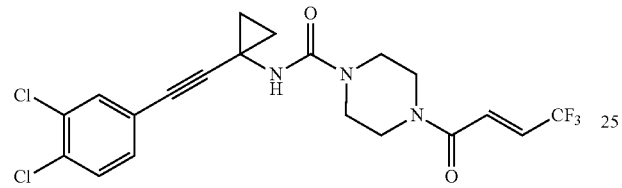

To a stirred solution of Intermediate 170 (0.100 g, 0.267 mmol) in DMF (25 mL) was added DIPEA (0.103 g, 0.80 mmol), (E)-4,4,4-trifluorobut-2-enoic acid (0.056 g, 0.400 mmol) and HATU (0.152 g, 0.400 mmol) at RT and attired for 2 h at RT. After completion of reaction, it was poured into ice water and extracted with EtOAc. The EtOAc layer was dried and concentrated and purified by Combiflash® silica gel column (DCM/MeOH=96/4) to get the compound (0.040 g, 32.7%). LCMS: m/z=459.8 [M]⁺; HPLC: 99.3%; ¹H NMR (400 MHz, CDCl₃): δ 7.47 (d, J=1.89 Hz, 1H), 7.37-7.30 (m, 1H), 7.23-7.17 (m, 1H), 6.95 (dq, J=2.11, 15.38 Hz, 1H), 6.82-6.70 (m, 1H), 5.13 (s, 1H), 3.80-3.28 (m, 8H), 1.47-1.04 (m, 4H).

Example-67: N-(1-((3,4-dichlorophenyl)ethynyl)cyclopropyl)-4-(2-fluoroacryloyl) piperazine-1-carboxamide

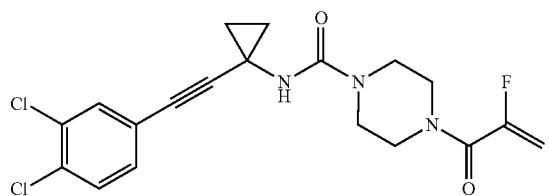 [SMILES: C=C(F)C(=O)N1CCN(C(=O)NC2(C#Cc3ccc(Cl)c(Cl)c3)CC2)CC1]

To a stirred suspension of N-(1-((3,4-dichlorophenyl)ethynyl)cyclopropyl) piperazine-1-carboxamide hydrochloride (Intermediate 17o) (0.2 g, 0.534 mmol) and 2-fluoroacrylic acid (0.096 g, 1.067 mmol) in DMF (4.0 mL) were added HATU (0.304 g, 0.800 mmol), DIPEA (0.28 mL, 1.601 mmol) at 0° C. and it was stirred for 16 h at RT. After completion of reaction, it was poured into ice water and extracted with EtOAc. The combined EtOAc layers were washed with brine and water; dried over Na₂SO₄ and evaporated under reduced pressure (0.220 g crude). Yield: 0.050 g (22.72%). HPLC: 98.93%; LCMS: m/z=410.0 [M+H]⁺⁺; ¹H NMR (400 MHz, CDCl₃): δ 7.47 (d, J=1.92 Hz, 1H), 7.33 (d, J=8.40 Hz, 1H), 7.20 (dd, J=1.93, 8.28 Hz, 1H), 5.38-5.12 (m, 2H), 3.65-3.42 (m, 8H), 1.39-1.30 (m, 2H), 1.24-1.11 (m, 2H).

Example-68: 4-(1-acryloylazetidine-3-carbonyl)-N-(1-((3,4-dichlorophenyl)ethynyl)cyclopropyl) piperazine-1-carboxamide

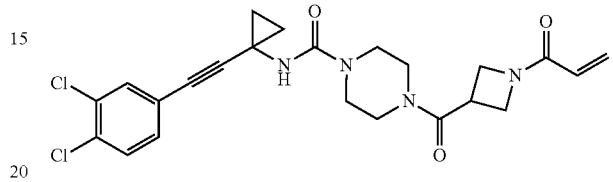

Step-1: Preparation of tell-butyl-3-(4-((1-((3,4-dichlorophenyl)ethynyl)cyclopropyl)carbamoyl)piperazine-1-carbonyl)azetidine-1-carboxylate The Intermediate 17o was reacted with 1-(tert-butoxycarbonyl)azetidine-3-carboxylic acid, triethylamine, HOBT, EDCl at 0° C. as per described procedure in the synthesis of Example-25 to obtain title compound (0.455 g, crude); LCMS: m/z=421.2 [M+H-100]⁺. Step-2: Preparation of 4-(azetidine-3-carbonyl)-N-(1-((3,4-dichlorophenyl)ethynyl)cyclopropyl) piperazine-1-carboxamide hydrochloride.

To a stirred solution of tert-butyl 3-(4-((1-((3,4-dichlorophenyl)ethynyl)cyclopropyl)-carbamoyl)piperazine-1-carbonyl)azetidine-1-carboxylate (0.45 g, 0.86 mmol) in dioxane (5 mL) was added dioxane.HCl (10 mL) drop wise at RT. The reaction mixture was stirred at RT for 2 h. The solvent was evaporated under reduced pressure to get the product (0.390 g, crude); LCMS: m/z=421 [M-36]⁺.

Step-3: Preparation of 4-(1-acryloylazetidine-3-carbonyl)-N-(1-((3,4-dichlorophenyl)ethynyl)cyclopropyl) piperazine-1-carboxamide To a stirred solution of 4-(azetidine-3-carbonyl)-N-(1-((3, 4-dichlorophenyl)ethynyl)-cyclopropyl) piperazine-1-carboxamide hydrochloride (step-2) (0.25 g, 0.54 mmol) in DCM (10 mL) was added NaHCO₃ solution (10 mL) and acryloyl chloride (45 µL, 0.54 mmol) at room temperature and stirred for 1 h. The DCM layer was separated and washed with brine solution, dried over anhydrous Na₂SO₄ and concentrated. The residue obtained was purified by prep. HPLC to obtain the title compound (0.080 g, 30.8%); LCMS: m/z=475.3 [M]+, HPLC: 99%, ¹H NMR (400 MHz, CDCl₃): δ 7.47 (d, J=1.87 Hz, 1H), 7.33 (d, J=8.30 Hz, 1H), 7.20 (dd, J=1.90, 8.30 Hz, 1H), 6.34 (dd, J=1.82, 16.98 Hz, 1H), 6.18 (dd, J=10.25, 16.99 Hz, 1H), 5.69 (dd, J=1.84, 10.29 Hz, 1H), 5.16 (s, 1H), 4.31 (q, J=9.20, 9.84 Hz, 2H), 4.14 (dd, J=6.31, 9.88 Hz, 1H), 3.48 (q, J=6.95 Hz, 4H), 3.33 (p, J=5.28 Hz, 4H), 1.42-1.31 (m, 2H), 1.31-1.12 (m, 4H).

Example-69: 4-Acryloyl-N-(4-(3,4-dichlorophenyl) but-3-yn-2-yl) piperazine-1-carbothioamide (±)

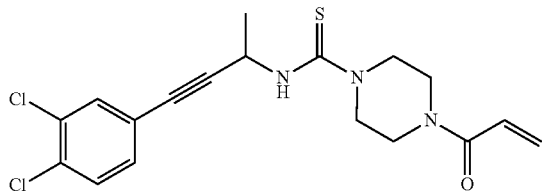 [SMILES: C=CC(=O)N1CCN(C(=S)NC(C)C#Cc2ccc(Cl)c(Cl)c2)CC1]

To a stirred solution of thiophosgene (0.290 g, 2.52 mmol) in THF, were added mixture of Intermediate-11 (HCl salt) (0.500 g, 2.016 mmol) and triethylamine (0.610 g, 6.04 mmol) in THF slowly at 0° C. After being stirred at RT for 15 min, the mixture of intermediate 12 (0.765 g, 4.34 mmol) and and triethylamine (0.610 g, 6.04 mmol) in THF was added and the reaction mixture was stirred 1 h at RT. After completion of reaction, the reaction mixture was diluted with ethylacetate layer dried and concentrated. The crude product purified by prep. TLC using 70% ethylacetate in hexane to afford the title compound as sticky solid (Yield: 0.1 g, 12.5%); HPLC: 91.1%; LCMS: m/z=396.2[M]+; $^1$H NMR (400 MHz, CDCl$_3$) δ 7.42-7.37 (m, 2H), 7.14 (dd, J=2.14, 8.41 Hz, 1H), 6.57 (dd, J=10.50, 16.77 Hz, 1H), 6.42-6.27 (m, 2H), 5.75 (dd, J=1.83, 10.58 Hz, 1H), 5.08 (tt, J=3.72, 7.60 Hz, 1H), 3.96-3.50 (m, 8H), 1.45 (d, J=6.75 Hz, 3H).

The following examples were prepared essentially by the procedure described in the preparation of Example-1 with appropriate variations in reactants, reagents and reaction conditions.

| Example | Structure | Yield & Analytical Data |
|---|---|---|
| 70 | 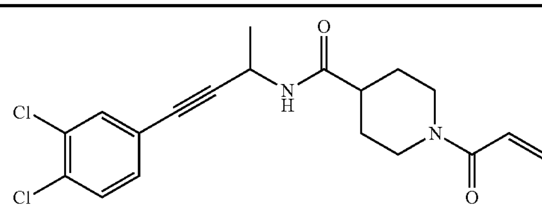 | Yield: 57%; HPLC: 99.03%; LCMS: m/z = 379.2 [M + H]$^+$; $^1$HNMR (400 MHz, DMSOd$_6$): δ 8.40 (d, J = 7.80 Hz, 1H), 7.70-7.54 (m, 2H), 7.35 (d, J = 8.27 Hz, 1H), 6.76 (dd, J = 10.45, 16.70 Hz, 1H), 6.12-5.97 (m, 1H), 5.68-5.56 (m, 1H), 4.79 (p, J = 7.24 Hz, 1H), 4.35 (d, J = 12.83 Hz, 1H), 4.02 (d, J = 13.40 Hz, 1H), 3.01 (t, J = 12.89 Hz, 1H), 2.61 (d, J = 14.82 Hz, 1H), 2.37 (td, J = 4.82, 9.91, 11.52 Hz, 1H), 1.69 (d, J = 12.62 Hz, 2H), 1.39 9(bs, 1H), 1.32 (d, J = 7.00 Hz, 3H). |
| 71 | Isomer 1 | Yield: 15%; HPLC: 92.13%; LCMS: m/z = 364.9 [M]$^+$; $^1$H NMR (400 MHz, DMSOd$_6$): δ 8.65-8.53 (m, 1H), 7.66 (d, J = 1.95 Hz, 1H), 7.61 (d, J = 8.35 Hz, 1H), 7.36 (dd, J = 1.97, 8.34 Hz, 1H), 6.53 (ddd, J = 2.17, 10.29, 16.78 Hz, 1H), 6.08 (ddd, J = 1.28, 2.36, 16.68 Hz, 1H), 5.62 (ddd, J = 1.38, 2.49, 10.33 Hz, 1H), 4.81 (p, J = 7.13 Hz, 1H), 3.77-3.37 (m, 3H), 2.94 (dp, J = 7.52, 39.79 Hz, 2H), 2.13-1.80 (m, 2H), 1.35 (d, J = 6.94 Hz, 3H). |
| 72 | Isomer 2 | Yield: 28%; HPLC: 98.58%; LCMS: m/z = 365.0 [M + H]$^+$; $^1$HNMR (400 MHz, DMSOd$_6$): δ 8.65-8.53 (m, 1H), 7.66 (d, J = 1.95 Hz, 1H), 7.61 (d, J = 8.35 Hz, 1H), 7.36 (dd, J = 1.97, 8.34 Hz, 1H), 6.53 (ddd, J = 2.17, 10.29, 16.78 Hz, 1H), 6.08 (ddd, J = 1.28, 2.36, 16.68 Hz, 1H), 5.62 (ddd, J = 1.38, 2.49, 10.33 Hz, 1H), 4.81 (p, J = 7.13 Hz, 1H), 3.77-3.37 (m, 3H), 2.94 (dp, J = 7.52, 39.79 Hz, 2H), 2.13-1.80 (m, 2H), 1.35 (d, J = 6.94 Hz, 3H). |
| 73 | 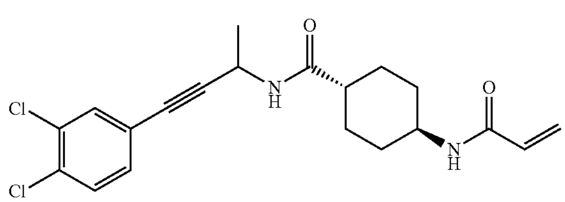 [SMILES: C=CC(=O)N[C@H]1CC[C@H](C(=O)NC(C)C#Cc2ccc(Cl)c(Cl)c2)CC1] | Yield: 33%; HPLC: 94.8%; LCMS: m/z = 393.2 [M + H]$^+$; $^1$HNMR (400 MHz, DMSOd$_6$) δ 8.31 (d, J = 7.94 Hz, 1H), 7.96 (d, J = 7.87 Hz, 1H), 7.80-7.54 (m, 2H), 7.38 (dd, J = 1.98, 8.28 Hz, 1H), 6.17 (dd, J = 9.95, 17.10 Hz, 1H), 6.05 (dd, J = 2.46, 17.07 Hz, 1H), 5.55 (dd, J = 2.49, 9.90 Hz, 1H), 4.83 (q, J = 7.09 Hz, 1H), 3.64-3.43 (m, 1H), 2.20-1.99 (m, 1H), 1.80 (dd, J = 12.05, 38.80 Hz, 4H), 1.38 (dd, J = |

| Example | Structure | Yield & Analytical Data |
|---|---|---|
| | | 10.05, 24.97 Hz, 5H), 1.17 (p, J = 11.09, 12.51 Hz, 2H). |
| 74 | 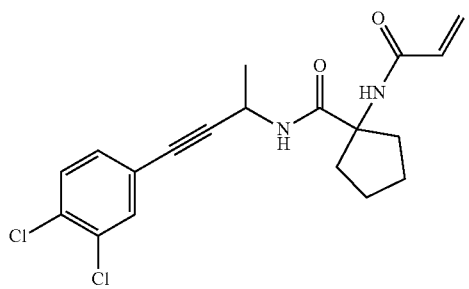 [SMILES: C=CC(=O)NC1(C(=O)NC(C)C#Cc2ccc(Cl)c(Cl)c2)CCCC1] | Yield: 29%; HPLC: 95.48%; LCMS: m/z = 381.2 [M + 2]+; $^1$H NMR (400 MHz, CDCl$_3$) δ 7.49 (d, J = 1.92 Hz, 2H), 7.35 (d, J = 8.27 Hz, 1H), 7.21 (dd, J = 1.94, 8.33 Hz, 1H), 6.32 (dd, J = 1.32, 16.86 Hz, 1H), 6.11 (dd, J = 10.25, 16.87 Hz, 1H), 5.74-5.69(m, 2H), 5.05-4.84 (m, 1H), 2.38-2.31 (m, 2H), 2.04 (td, J = 6.27, 13.71 Hz, 2H), 1.87-1.70 (m, 4H), 1.46 (d, J = 6.90 Hz, 3H). |

Example-75: (1r,4r)-N-(4-(3,4-dichlorophenyl)but-3-yn-2-yl)-4-(vinylsulfonamido) cyclohexane-1-carboxamide (±)

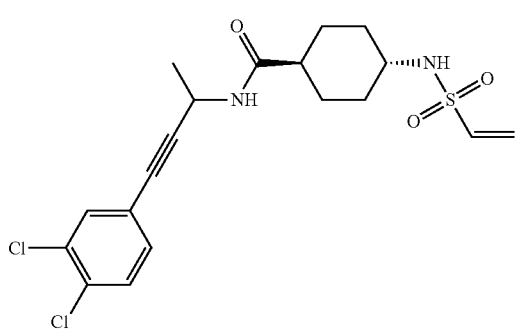 [SMILES: C=CS(=O)(=O)N[C@H]1CC[C@H](C(=O)NC(C)C#Cc2ccc(Cl)c(Cl)c2)CC1]

The title compound was obtained as per the procedure described in the preparation of Example-1. Yield: 20%, LCMS: m/z=431.1 [M+H]$^+$; HPLC: 95.5%, $^1$H NMR (400 MHz, DMSO-d$_6$) δ 8.29 (d, J=7.92 Hz, 1H), 7.70-7.55 (m, 2H), 7.37 (dd, J=1.95, 8.39 Hz, 1H), 7.26 (d, J=7.36 Hz, 1H), 6.73 (dd, J=9.96, 16.49 Hz, 1H), 6.08-5.84 (m, 2H), 4.80 (t, J=7.32 Hz, 1H), 2.90 (dt, J=4.00, 7.48 Hz, 1H), 2.00 (m, 1H) 1.88-1.93 (m, 4H), 1.44-1.28 (m, 4H), 1.28-1.03 (m, 3H).

Example-76: 4-acrylamido-N-(4-(3,4-dichlorophenyl)but-3-yn-2-yl)benzamide (±)

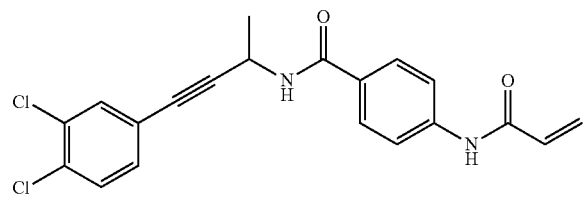 [SMILES: C=CC(=O)Nc1ccc(C(=O)NC(C)C#Cc2ccc(Cl)c(Cl)c2)cc1]

Step-1: Preparation of 4-acrylamido-N-(but-3-yn-2-yl)benzamide(±)

But-3-yn-2-yl methanesulfonate (±) (1.0 g, 6.75 mmol) was stirred in aq. NH$_3$ (10 mL) at RT for 16 h. The reaction mixture was extracted with DCM (25 mL). The DCM layer was dried over Na$_2$SO$_4$ and filtered. To the above obtained DCM solution 4-acrylamidobenzoic acid (prepared as per the procedure described in US2008/300268 A1) (0.990 gm, 5.19 mmol, 1.0 eq), DIPEA (3.58 mL, 20.22 mmol) and HATU (3.86 gm, 10.12 mmol, 1.5eq) were added at RT and the resulting reaction mixture was stirred at RT for 16 h. The reaction mixture was washed with water (20 mL) followed by brine (20 mL). The DCM layer dried and concentrated to obtain the crude compound. The residue obtained was purified by Combiflash® on silica gel (hexanes/ethyl acetate=60/40) to obtain title compound (0.650 gm, 40%) LCMS: m/z=243.4 [M+H]+.

Step-2: Preparation of 4-acrylamido-N-(4-(3,4-dichlorophenyl)but-3-yn-2-yl)benzamide (±)

4-acrylamido-N-(but-3-yn-2-yl)benzamide(±) (0.65 g, 2.68 mmol) was treated with 1,2-dichloro-4-iodobenzene (0.487 g, 1.79 mmol) as described in the procedure for the preparation of Intermediate 8 to give title compound (Yield: 0.12 g, 11.5%) LCMS: m/z=387.0 [M+H]+. HPLC: 95.13%; $^1$H NMR (400 MHz, DMSOd$_6$): δ 10.39 (s, 1H), 8.87 (d, J=7.89 Hz, 1H), 7.93-7.85 (m, 2H), 7.77-7.69 (m, 3H), 7.64 (d, J=8.38 Hz, 1H), 7.42 (dd, J=1.99, 8.32 Hz, 1H), 6.45 (dd, J=10.04, 16.96 Hz, 1H), 6.29 (dd, J=2.04, 16.90 Hz, 1H), 5.80 (dd, J=2.06, 10.05 Hz, 1H), 5.11 (p, J=7.04 Hz, 1H), 1.50 (d, J=6.97 Hz, 3H).

Example-77: 4-(3-bromo-4,5-dihydroisoxazole-5-carbonyl)-N-(4-(3,4-dichlorophenyl)but-3-yn-2-yl) piperazine-1-carboxamide(±)

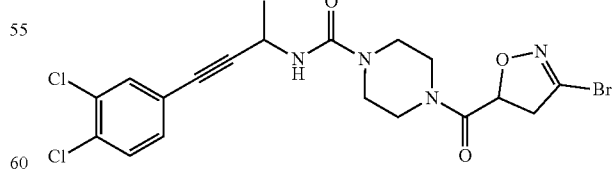

Step-1: tert-butyl 4-(3-bromo-4,5-dihydroisoxazole-5-carbonyl) piperazine-1-carboxylate To a stirred suspension of tert-butyl 4-acryloylpiperazine-1-carboxylate (0.200 g, 0.832 mmol) in N,N-dimethylformamide (7.0 mL) were added hydroxycarbonimidic dibromide (0.253 g, 1.248 mmol) and aq.KHCO$_3$ (0.250 g, 2.496 mmol, 2 mL) at 0° C. The reaction mixture, after being stirred at room temperature for 14 h, was diluted with water and extracted with ethyl acetate. The combined organics layer was washed with brine, dried over sodium sulphate and evaporated under reduced pressure. The crude obtained was purified by Combiflash® on silica gel (hexanes/ethyl acetate=99.9/0.1) to afford the title compound (0.160 g, 53.15%) as a liquid. LCMS: m/z=448.35 [M+H]+.

Step-2: (3-bromo-4,5-dihydroisoxazol-5-yl)(piperazin-1-yl)methanone trifluoromethyl carbonate (±)

To a stirred suspension of tert-butyl 4-(3-bromo-4,5-dihydroisoxazole-5-carbonyl) piperazine-1-carboxylate (0.20 g, 0.552 mmol) in dichloromethane (5.0 mL) was added TFA (0.20 mL, 2.612 mmol) at RT and stirred for 14 h. The reaction mixture was evaporated under reduced pressure and the residue obtained was triturated with diethyl ether to afford the title compound (0.199 g crude). LCMS: m/z=262.11 [M]+.

Step-3: 4-(3-bromo-4,5-dihydroisoxazole-5-carbonyl)-N-(4-(3,4-dichlorophenyl)but-3-yn-2-yl)piperazine-1-carboxamide(±)

The title compound above was prepared according to the method described in Example-54. Yield: 53.15%; HPLC: 99.7%; LCMS: m/z=448.35 [M+H]+. $^1$H NMR (400 MHz, CDCl$_3$) δ 7.52-7.46 (m, 1H), 7.34 (d, J=8.31 Hz, 1H), 7.23-7.18 (m, 1H), 5.28 (dd, J=7.62, 11.27 Hz, 1H), 5.00-4.84 (m, 1H), 4.61 (d, J=7.87 Hz, 1H), 3.89-3.76-(m, 2H), 3.66-3.38 (m, 6H), 3.25 (dd, J=11.29, 17.52 Hz, 2H), 1.46 (d, J=6.87 Hz, 3H).

Example 78: Determination of Anti Proliferative Activity in NCI-H1792 Cells by XTT Assay NCI-H1792 cells (ATCC CRL-5895) were plated at 2000 cells/well in 96 well flat clear bottom plates (Corning, Cat. No 3596) using complete RPMI media. After 24 hours, compounds of present invention were added to cells from 20 mM stocks made in DMSO (Sigma Cat no. D2650). Each concentration of compound was tested in triplicate with DMSO concentration not exceeding a final percentage of 0.3 in the cells. After 72 hours of incubation in CO$_2$ incubator, XTT (Invitrogen, Cat. no X6493) was added to the wells. XTT was dissolved in serum free media at 1 mg/ml and absorbance readings were taken in spectrophotometer at 465 nm. The data was analysed using graph pad prism software. Positive control (100% survival)=Cells in complete media with 0.3% DMSO; Negative control/blank (0% survival)=Media alone containing 0.3% DMSO.

The compounds of the present invention were screened in the above mentioned assay and the results are tabulated below. The IC$_{50}$ values of the compounds are set forth below wherein "A" refers to an IC$_{50}$ value of less than 10 μM, "B" refers to IC$_{50}$ value ranges from 10.01 μM to 25 μM and "C" refers to an IC$_{50}$ value of greater than 25 μM.

IC$_{50}$ values and % viability for selected compounds of the present invention

| | H1792 cell line | |
|---|---|---|
| Example | IC$_{50}$ (μM) | % Viability (at 30 μM) |
| 1 | A | 40 |
| 1a | A | 45 |
| 1b | B | 37 |
| 2 | A | 22 |
| 2a | C | 56 |
| 2b | B | 57 |
| 3 | A | 3 |
| 4 | B | 15 |
| 5 | A | 57 |
| 6 | B | 19 |
| 7 | B | 33 |
| 8 | A | 35 |
| 9 | C | 47 |
| 10 | C | 89 |
| 11 | C | 91 |
| 12 | C | 83 |
| 13 | C | ND |
| 14 | C | ND |
| 15 | C | 90 |
| 16 | B | 3 |
| 19 | A | ND |
| 33 | ND | 54 |
| 47 | A | 26 |
| 49 | B | 35 |
| 50 | A | 17 |
| 54 | A | 22 |
| 55 | C | 100 |
| 56 | B | 39 |
| 57 | A | 17 |
| 58 | C | ND |
| 65 | C | 73 |
| 69 | B | 18 |
| 70 | A | 33 |
| 71 | B | 26 |
| 72 | B | 27 |
| 73 | C | 64 |
| 75 | A | 10 |
| 76 | A | 26 |

ND = Not determined

Example 79: Determination of Anti Proliferative Activity in NCI-H2122 Cells by XTT Assay NCI-H2122 cells (ATCC CRL-5985) were plated at 1000 cells/well in 96 well flat clear bottom plates (Corning, Cat. No 3596) using complete RPMI-1640 media. After 24 hours, compounds of present invention were added to cells from 10 mM stocks made in DMSO (Sigma Cat no. D2650). Each concentration of compound was tested in triplicate with DMSO concentration not exceeding a final percentage of 0.3 in the cells. Complete RPMI-1640 media changed at Day 3 (72 hour) and Day 6 (144 hour) along with compounds of current invention. After 8 days (192 hour) of incubation assay terminated using 50 μl of XTT reagent (Invitrogen, Cat. no X6493). XTT reagent was made by dissolving 1 mg/mi XTT in serum free media with addition of 25 μM Phenazine methosulfate (sigma Cat. no P9625). Absorbance readings were taken in spectrophotometer at 465 nm. The data was analysed using graph pad prism software. Positive control (100% survival)=Cells in complete media with 0.3% DMSO; Negative control/blank (0% survival)=Media alone containing 0.3% DMSO.

The compounds of the present invention were screened in the above mentioned assay and the results are tabulated below. The IC$_{50}$ values of the compounds are set forth below wherein "A" refers to an IC$_{50}$ value of less than 10 μM, "B"

refers to $IC_{50}$ value ranges from 10.01 μM to 25 μM and "C" refers to an $IC_{50}$ value of greater than 25 μM.

| $IC_{50}$ values and % viability for selected compounds of the present invention | | |
|---|---|---|
| | H2122 cell line | |
| Example | $IC_{50}$ (μM) | % Viability (at 30 μM) |
| 1a | ND | 26 |
| 17 | B | 19 |
| 18 | A | 1 |
| 21 | B | 31 |
| 22 | C | 49 |
| 23 | A | 21 |
| 24 | A | ND |
| 25 | B | 16 |
| 26 | B | ND |
| 27 | A | ND |
| 28 | B | ND |
| 29 | A | ND |
| 30 | B | 19 |
| 31 | B | 19 |
| 32 | B | 15 |
| 33 | C | ND |
| 40 | B | ND |
| 41 | B | ND |
| 42 | A | 0 |
| 42a | A | ND |
| 42b | A | ND |
| 43 | C | 78 |
| 44 | C | 99 |
| 48a | C | ND |
| 48b | B | ND |
| 50 | ND | 1 |
| 51 | ND | 0 |
| 52 | B | 78 |
| 53 | B | 99 |
| 58 | ND | 72 |
| 59 | A | 0 |
| 60 | C | 90 |
| 61 | C | 59 |
| 62 | B | 33 |
| 63 | A | 18 |
| 64 | C | 56 |
| 66 | A | ND |
| 68 | C | ND |
| 74 | C | 60 |
| 77 | B | ND |

ND = Not determined

Example 80: Determination of Anti Proliferative Activity in OCI-Ly10 Cells

OCI-Ly10 cells (UHN Canada) were plated at 7500 cells/well in 96 well flat bottom plates (Corning, Cat. No CLS3904) using complete Iscove's Modified Dulbecco's Medium (IMDM. After 6 hours, compounds from the present invention were added to the cells from 10 mM stocks made in DMSO (Sigma, Cat. No D2650). Each concentration of compound was tested in triplicates with DMSO concentration not exceeding a final percentage of 0.1 in the cells. After 72 hours of incubation in $CO_2$ incubator, CTG (Promega, Cat. No G7572) was added to the wells and Luminescence readings were taken in the plate reader. Percent inhibition in proliferation was calculated using Microsoft Excel software. Positive control (100% survival)=Cells in complete media with 0.1% DMSO; Negative control/blank (0% survival)=Media alone containing 0.1% DMSO.

| Percent inhibition for selected compounds of the present invention | | |
|---|---|---|
| Example | % inhibition (at 1 μM) | % inhibition (at 10 μM) |
| 3 | 12 | 92 |
| 5 | 43 | 77 |
| 23 | 48 | 67 |
| 24 | 35 | 68 |
| 25 | 3 | 72 |
| 29 | 42 | 90 |
| 35 | 24 | 67 |
| 36 | 39 | 65 |
| 41 | 0 | 36 |
| 42 | 81 | 62 |
| 45 | 0 | 44 |
| 50 | 32 | 48 |
| 51 | 3 | 52 |
| 52 | 3 | 82 |
| 54 | 37 | 56 |
| 59 | 25 | 100 |
| 63 | 49 | 79 |
| 66 | 75 | 73 |
| 71 | 9 | 62 |
| 72 | 4 | 55 |

We claim:

1. A compound of formula (I)

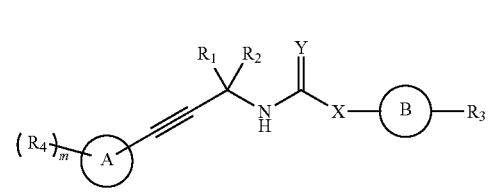

(I)

or a pharmaceutically acceptable salt or a stereoisomer thereof; wherein,

A represents aryl or heteroaryl;

X represents N—$R_y$, or absent;

Y represents O, S or NCN;

B represents aryl, cycloalkyl or heterocycloalkyl; wherein the aryl, cycloalkyl or heterocycloalkyl are optionally substituted with one or more groups selected from alkyl, halo and oxo;

$R_1$ represents unsubstituted alkyl; $R_2$ represents hydrogen or unsubstituted alkyl; or $R_1$ and $R_2$ together with the carbon atoms to which they are attached form 3- to 5-membered cycloalkyl ring;

$R_3$ represents —$C(O)R_a$, —$S(O)_2R_a$, —$NHS(O)_2R_a$, —$NR_bC(O)R_a$, =$NOR_a$, heteroaryl, heterocycloalkyl or (heterocycloalkyl)alkyl-; wherein the heteroaryl and heterocycloalkyl are optionally substituted with one or more groups selected from alkyl, halo, oxo and —$C(O)R_x$;

$R_4$ represents alkyl, halo, haloalkyl, cyano, alkoxy, aryloxy, hydroxyalkyl, acetylene, acyl, hydroxy, cycloalkyl or —$N(R_x)_2$; wherein the alkoxy is unsubstituted or substituted with unsubstituted phenyl, and the cycloalkyl is optionally substituted with alkyl;

$R_a$ represents alkyl, alkenyl, haloalkyl, cycloalkyl or heterocycloalkyl; wherein the alkyl, alkenyl, haloalkyl, cycloalkyl and heterocycloalkyl are optionally substituted with one or more groups selected from alkyl, halo, aryl, cycloalkyl, haloalkyl, amino, amido, alkylamino, aminoalkyl, hydroxyl, cyano, alkoxy, alkoxyaryl, aryloxy, hydroxyalkyl, carboxylic acid, ester, thioester, oxo(=O) and —C(O)R$_x$;

R$_x$ represents hydrogen, alkyl, alkenyl, acyl or —C(O)-cycloalkyl;

R$_y$ represents hydrogen or alkyl;

R$_b$ represents hydrogen, alkyl or alkenyl;

'm' represents 0, 1, 2 or 3.

2. The compound of claim 1, wherein B represents heterocycloalkyl.

3. The compound of claim 1, wherein B represents

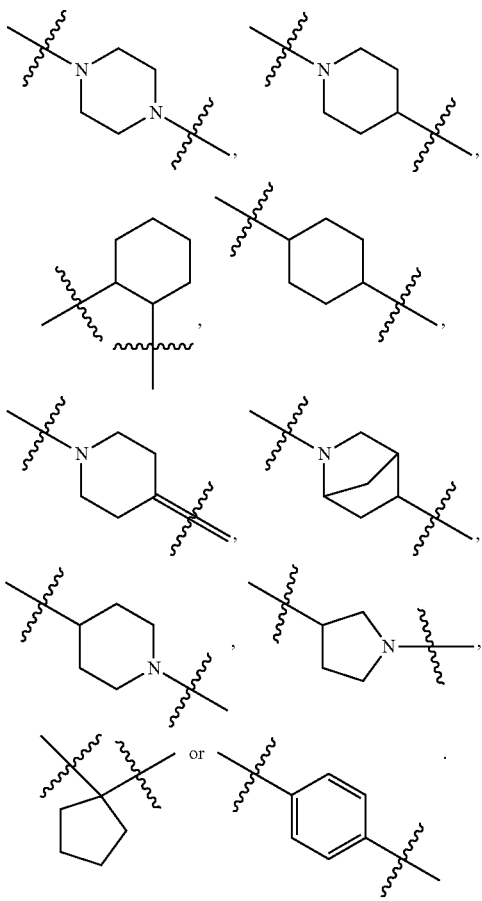

4. The compound of claim 1, wherein R$_1$ represents unsubstituted alkyl; and R$_2$ represents hydrogen.

5. The compound of claim 1, wherein R$_1$ and R$_2$ together with the carbon atoms to which they are attached form cyclopropyl or cyclopentyl ring.

6. The compound of claim 1, wherein A represents aryl.

7. The compound of claim 1, represented by compound of formula (IA):

(IA)

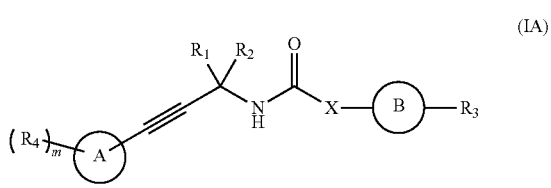

or a pharmaceutically acceptable salt or stereoisomer thereof; wherein A, R$_1$, R$_2$, R$_3$, R$_4$, B, X and 'm' are as defined in claim 1.

8. The compound of claim 7, wherein B represents 5- or 6-membered cycloalkyl.

9. The compound of claim 7, wherein B represents 5- or 6-membered heterocycloalkyl.

10. The compound of claim 7, wherein A represents aryl.

11. The compound of claim 7, wherein R$_3$ represents —NHS(O)$_2$R$_a$, or —NR$_b$C(O)R$_a$.

12. The compound of claim 1, represented by compound of formula (IB):

(IB)

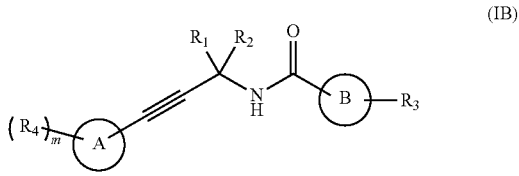

or a pharmaceutically acceptable salt or stereoisomer thereof; wherein A, R$_1$, R$_2$, R$_3$, R$_4$, B, and 'm' are as defined in claim 1.

13. The compound of claim 12, wherein B represents heterocycloalkyl optionally substituted with one or more groups selected from alkyl, halo or oxo.

14. The compound of claim 12, wherein B represents 5- or 6-membered heterocycloalkyl.

15. The compound of claim 1, represented by compound of formula (IC):

(IC)

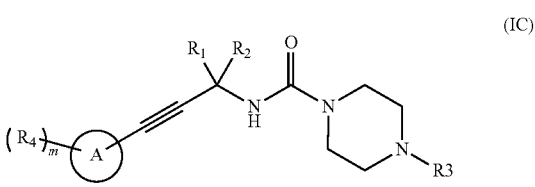

or a pharmaceutically acceptable salt or stereoisomer thereof; wherein A, R$_1$, R$_2$, R$_3$, R$_4$ and 'm' are as defined in claim 1.

16. The compound of claim 15, wherein R$_1$ represents unsubstituted alkyl; and R$_2$ represents hydrogen or unsubstituted alkyl.

17. The compound of claim 15, wherein R$_1$ and R$_2$ together with the carbon atoms to which they are attached form cyclopropyl or cyclopentyl.

18. The compound of claim 15, wherein R$_3$ represents heterocycloalkyl optionally substituted with —C(O)R$_x$.

19. The compound of claim 15, wherein R$_4$ represents alkyl, halo, haloalkyl or cycloalkyl, wherein the cycloalkyl is optionally substituted with alkyl.

20. The compound of claim 1, represented by compound of formula (ID):

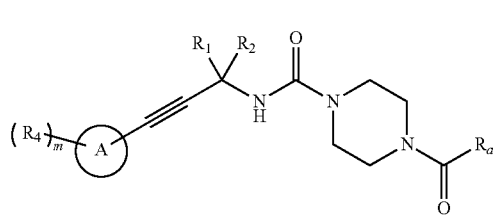

or a pharmaceutically acceptable salt or stereoisomer thereof; wherein A, $R_1$, $R_2$, $R_4$, $R_a$ and m are as defined in claim 1.

21. The compound of claim 20, wherein $R_a$ represents alkenyl, cycloalkyl or heterocycloalkyl; wherein the alkenyl, cycloalkyl and heterocycloalkyl are optionally substituted with one or more groups selected from halo, aryl, haloalkyl or carboxylic acid.

22. The compound of claim 21, wherein $R_a$ represents alkenyl substituted with alkyl or haloalkyl.

23. The compound of claim 1, represented by compound of formula (IE):

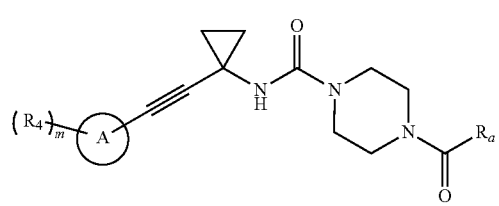

or a pharmaceutically acceptable salt or stereoisomer thereof; wherein A, $R_4$, $R_a$ and 'm' are as defined in claim 1.

24. The compound of claim 1, represented by compound of formula (IF):

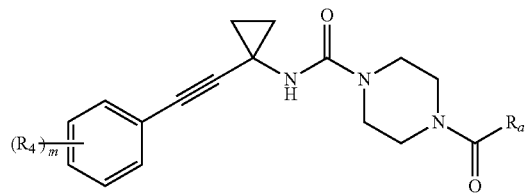

or a pharmaceutically acceptable salt or stereoisomer thereof; wherein $R_4$, $R_a$ and m are same as defined in claim 1.

25. A compound selected from:

| Example | Structure |
| --- | --- |
| 1 | ![structure] |
| 1a | ![structure] (Isomer-1) ; |
| 1b | ![structure] (Isomer-2) ; |

-continued

| Example | Structure |
|---------|-----------|
| 2 | 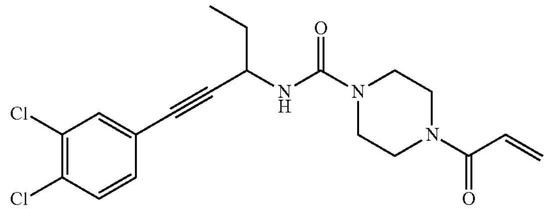 |
| 2a | (Isomer-1) |
| 2b | (Isomer-2) |
| 3 | 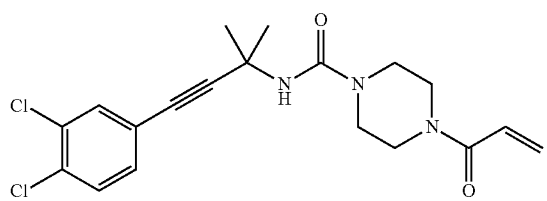 |
| 4 | 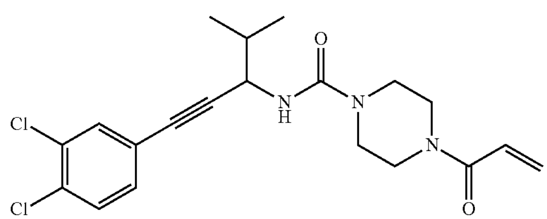 |
| 5 | 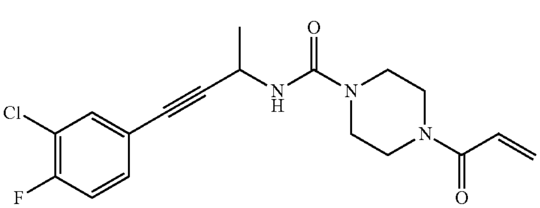 |
| 6 | 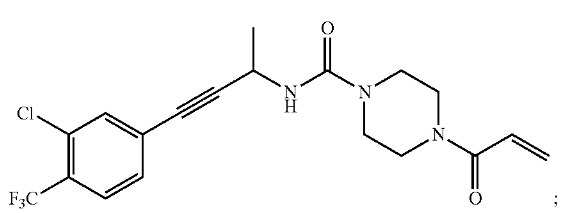 [SMILES: C=CC(=O)N1CCN(C(=O)NC(C)C#Cc2ccc(C(F)(F)F)c(Cl)c2)CC1] |

-continued
| Example | Structure |
|---|---|
| 7 | 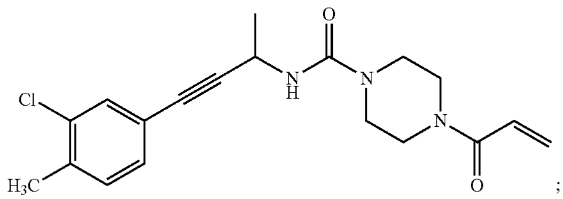 [SMILES: C=CC(=O)N1CCN(C(=O)NC(C)C#Cc2ccc(C)c(Cl)c2)CC1] |
| 8 | 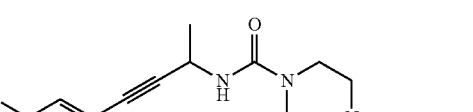 |
| 9 | 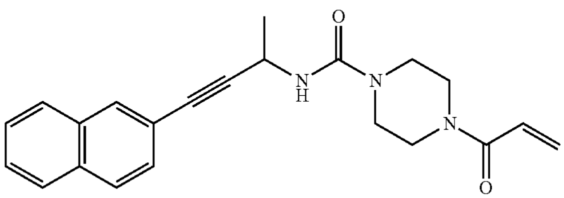 |
| 10 | 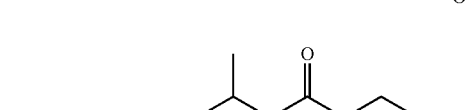 |
| 11 | 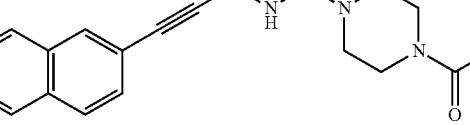 |
| 12 | 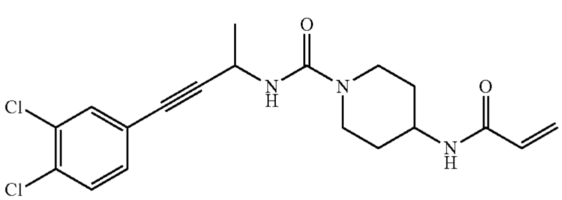 |
| 13 | 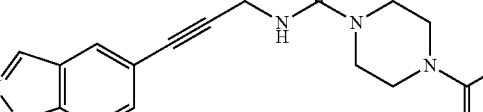 |

-continued
| Example | Structure |
|---|---|
| 14 | 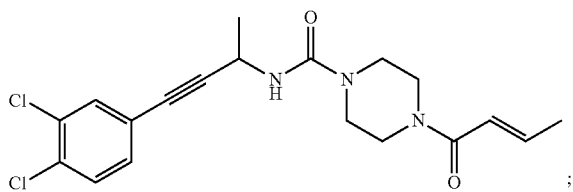 [SMILES: C/C=C/C(=O)N1CCN(C(=O)NC(C)C#Cc2ccc(Cl)c(Cl)c2)CC1] |
| 15 | 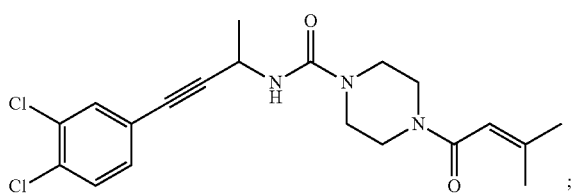 [SMILES: CC(C)=CC(=O)N1CCN(C(=O)NC(C)C#Cc2ccc(Cl)c(Cl)c2)CC1] |
| 16 | 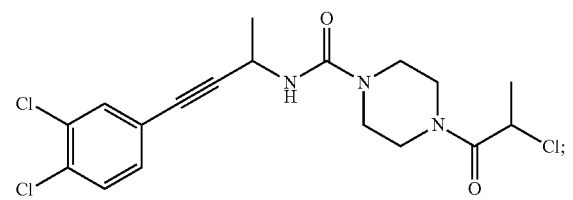 [SMILES: CC(C#Cc1ccc(Cl)c(Cl)c1)NC(=O)N1CCN(C(=O)C(C)Cl)CC1] |
| 17 | 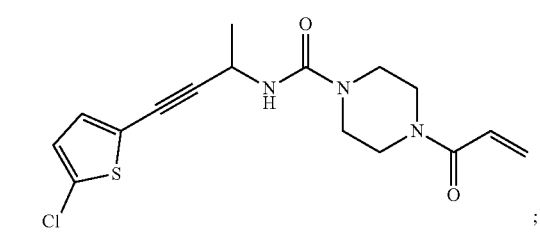 [SMILES: C=CC(=O)N1CCN(C(=O)NC(C)C#Cc2ccc(Cl)s2)CC1] |
| 18 | 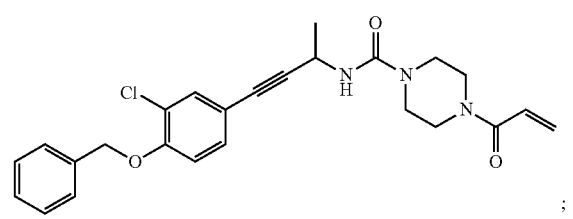 [SMILES: C=CC(=O)N1CCN(C(=O)NC(C)C#Cc2ccc(OCc3ccccc3)c(Cl)c2)CC1] |
| 19 | 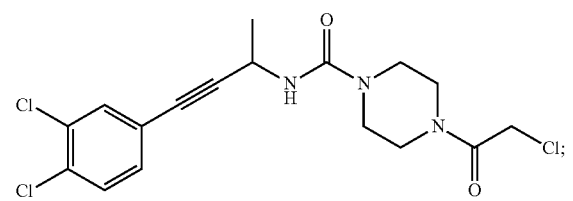 [SMILES: CC(C#Cc1ccc(Cl)c(Cl)c1)NC(=O)N1CCN(C(=O)CCl)CC1] |
| 20 | 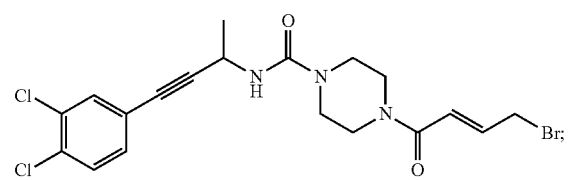 [SMILES: CC(C#Cc1ccc(Cl)c(Cl)c1)NC(=O)N1CCN(C(=O)/C=C/CBr)CC1] |

-continued

| Example | Structure |
|---------|-----------|
| 21 | 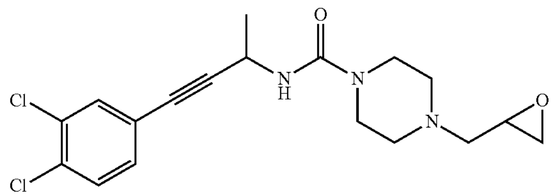 |
| 22 | 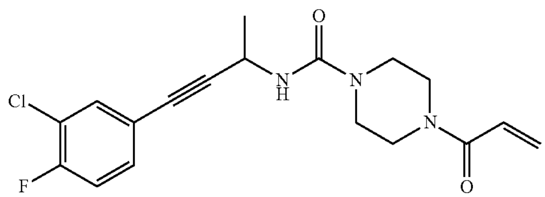 |
| 23 | 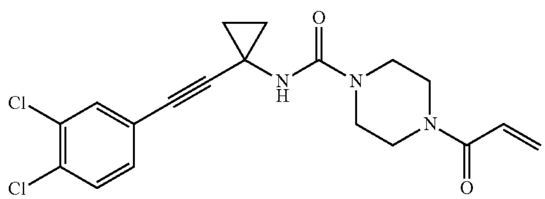 |
| 24 | 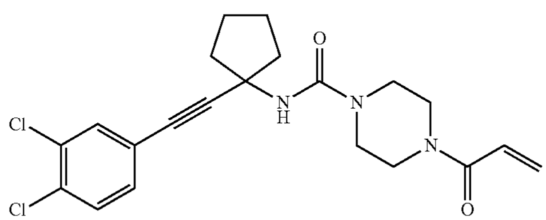 |
| 25 | 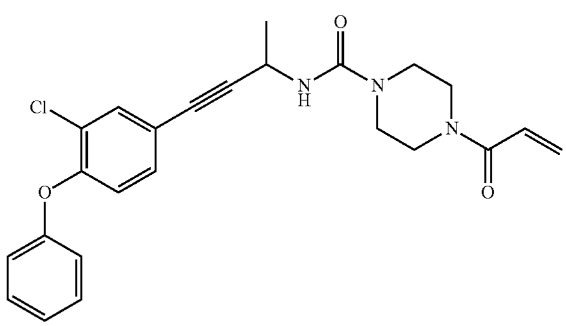 |
| 26 | 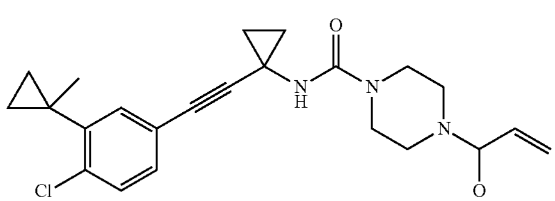 |
| 27 | 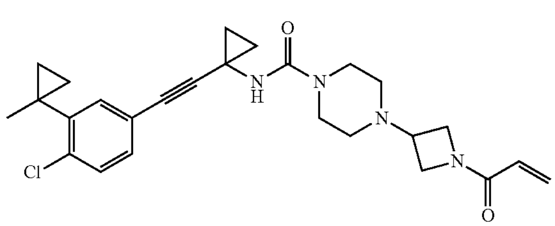 |

| Example | Structure |
|---|---|
| 28 | 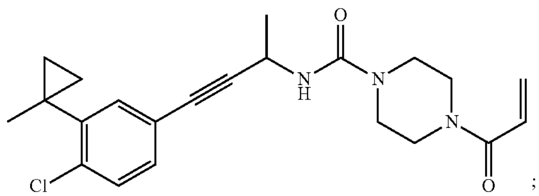 [SMILES: C=CC(=O)N1CCN(C(=O)NC(C)C#Cc2ccc(Cl)c(C3(C)CC3)c2)CC1] |
| 29 | 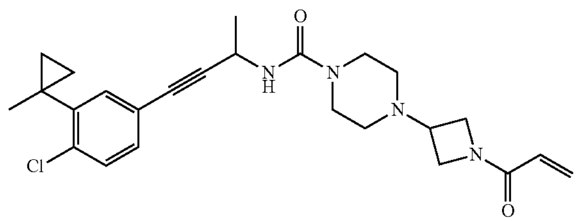 |
| 30 | 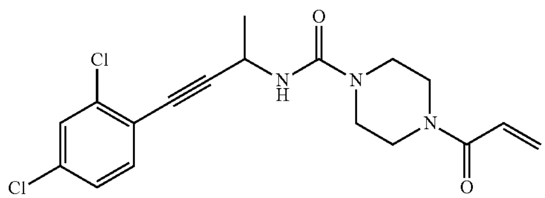 |
| 31 | 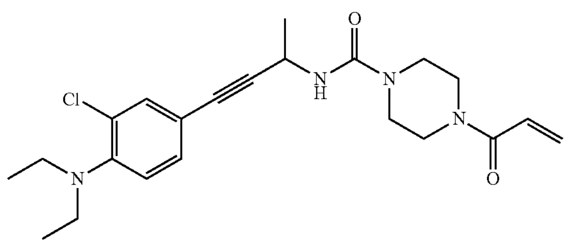 |
| 32 | 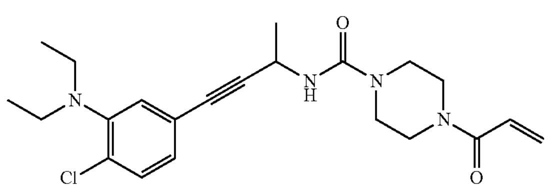 |
| 33 | 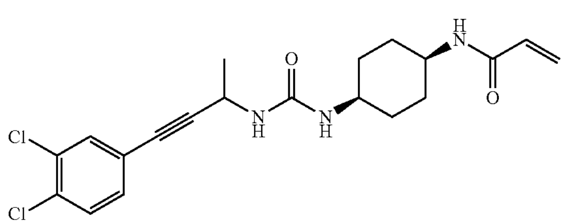 |
| 34 | 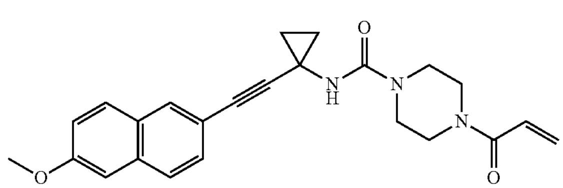 |

| Example | Structure |
|---|---|
| 35 | 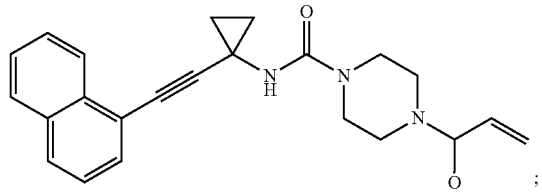 [SMILES: C=CC(OC)N1CCN(C(=O)NC2(C#Cc3cccc4ccccc34)CC2)CC1] |
| 36 | 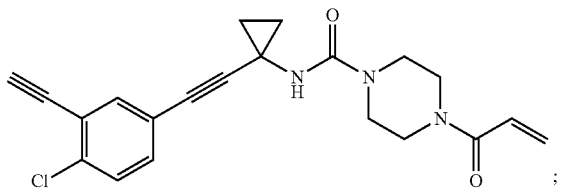 [SMILES: C#Cc1cc(C#CC2(NC(=O)N3CCN(C(=O)C=C)CC3)CC2)ccc1Cl] |
| 37 | 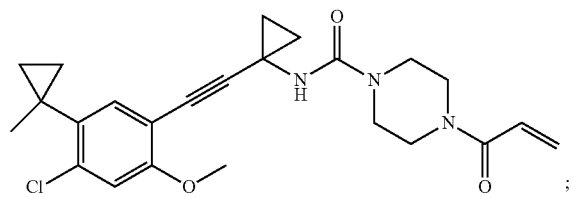 [SMILES: C=CC(=O)N1CCN(C(=O)NC2(C#Cc3cc(C4(C)CC4)c(Cl)cc3OC)CC2)CC1] |
| 38 | 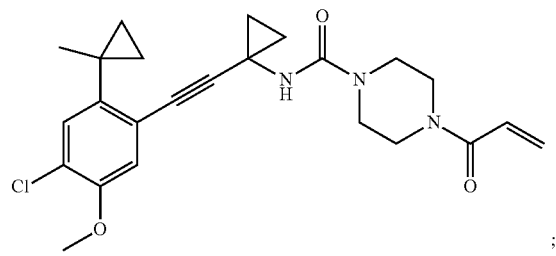 [SMILES: C=CC(=O)N1CCN(C(=O)NC2(C#Cc3cc(OC)c(Cl)cc3C3(C)CC3)CC2)CC1] |
| 39 | 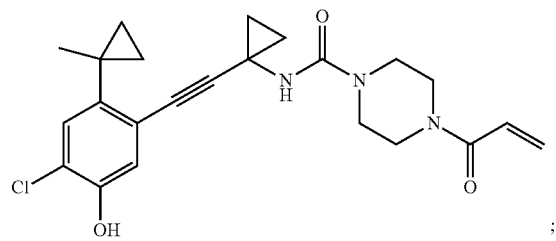 [SMILES: C=CC(=O)N1CCN(C(=O)NC2(C#Cc3cc(O)c(Cl)cc3C3(C)CC3)CC2)CC1] |
| 40 | 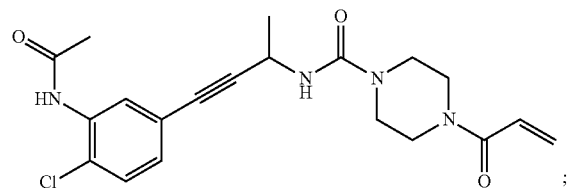 [SMILES: C=CC(=O)N1CCN(C(=O)NC(C)C#Cc2ccc(Cl)c(NC(C)=O)c2)CC1] |
| 41 | 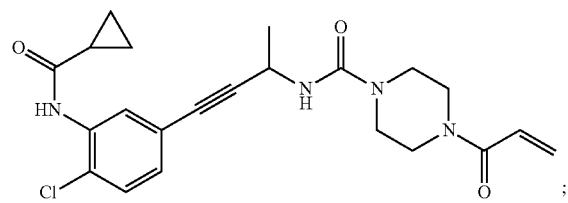 [SMILES: C=CC(=O)N1CCN(C(=O)NC(C)C#Cc2ccc(Cl)c(NC(=O)C3CC3)c2)CC1] |

-continued
| Example | Structure |
|---|---|
| 42 | 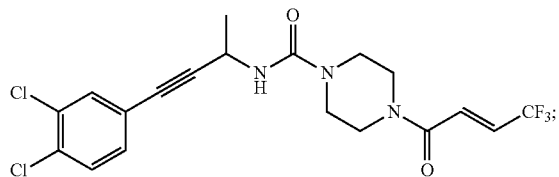 |
| 42a | 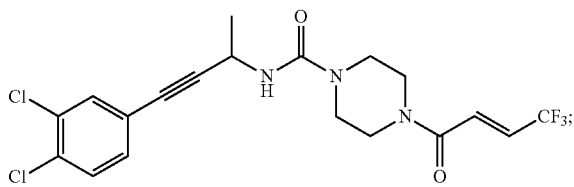<br>(Isomer-1) |
| 42b | 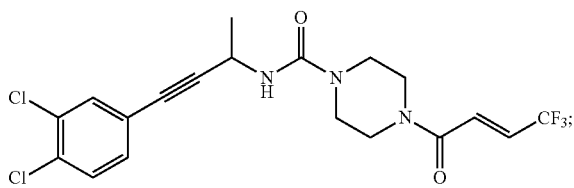 [SMILES: CC(C#Cc1ccc(Cl)c(Cl)c1)NC(=O)N1CCN(C(=O)/C=C/C(F)(F)F)CC1]<br>(Isomer-2) |
| 43 | 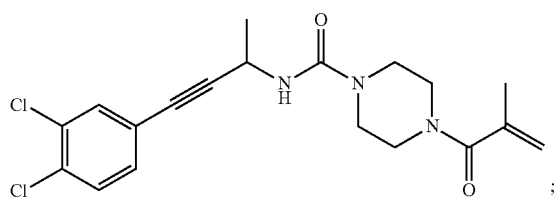 [SMILES: C=C(C)C(=O)N1CCN(C(=O)NC(C)C#Cc2ccc(Cl)c(Cl)c2)CC1] |
| 44 | 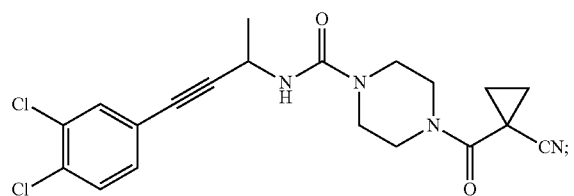 [SMILES: CC(C#Cc1ccc(Cl)c(Cl)c1)NC(=O)N1CCN(C(=O)C2(C#N)CC2)CC1] |
| 45 | 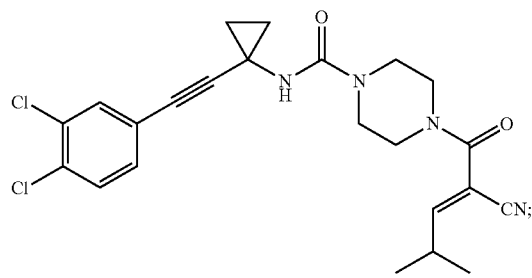 [SMILES: CC(C)/C=C(\C#N)C(=O)N1CCN(C(=O)NC2(C#Cc3ccc(Cl)c(Cl)c3)CC2)CC1] |

| Example | Structure |
|---------|-----------|
| 46 | ![structure] |
| 47 | ![structure] |
| 48a | ![structure] (Isomer-1) |
| 48b | ![structure] (Isomer-2) |
| 49 | ![structure] |
| 50 | ![structure] |

| Example | Structure |
|---|---|
| 51 | 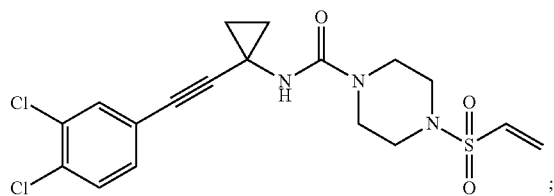 [SMILES: C=CS(=O)(=O)N1CCN(C(=O)NC2(C#Cc3ccc(Cl)c(Cl)c3)CC2)CC1] |
| 52 | 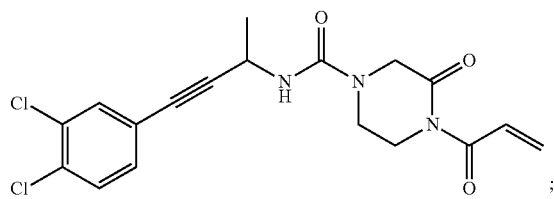 [SMILES: C=CC(=O)N1CCN(C(=O)NC(C)C#Cc2ccc(Cl)c(Cl)c2)CC1=O] |
| 53 | 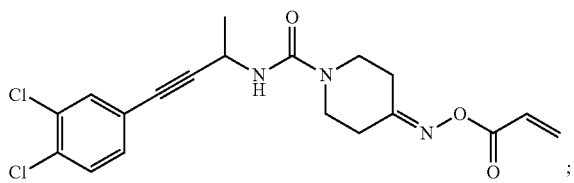 [SMILES: C=CC(=O)ON=C1CCN(C(=O)NC(C)C#Cc2ccc(Cl)c(Cl)c2)CC1] |
| 54 | 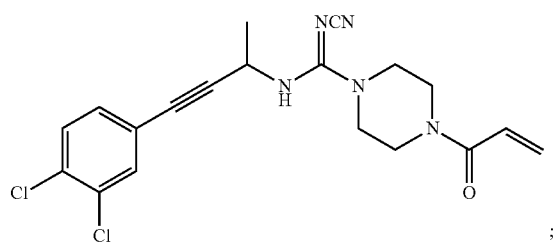 |
| 55 | 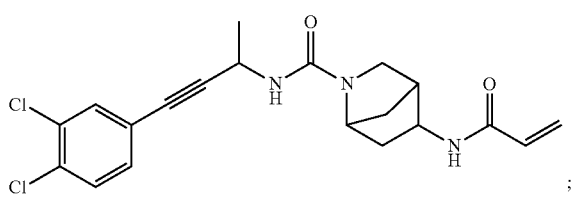 [SMILES: C=CC(=O)NC1CC2CC1CN2C(=O)NC(C)C#Cc1ccc(Cl)c(Cl)c1] |
| 56 | 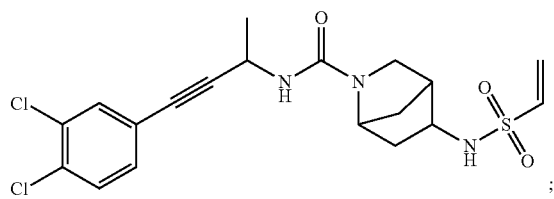 [SMILES: C=CS(=O)(=O)NC1CC2CC1CN2C(=O)NC(C)C#Cc1ccc(Cl)c(Cl)c1] |
| 57 | 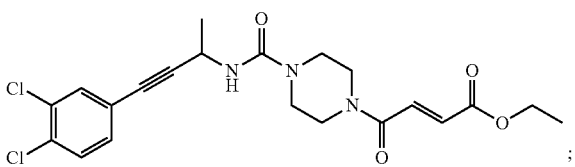 [SMILES: CCOC(=O)/C=C/C(=O)N1CCN(C(=O)NC(C)C#Cc2ccc(Cl)c(Cl)c2)CC1] |

| Example | Structure |
|---|---|
| 58 | 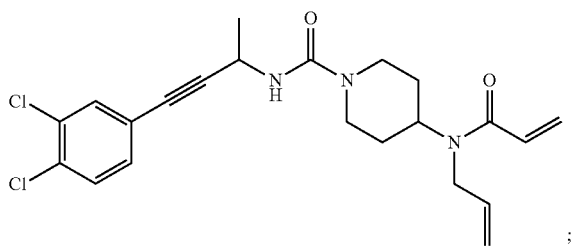 [SMILES: C=CCN(C(=O)C=C)C1CCN(C(=O)NC(C)C#Cc2ccc(Cl)c(Cl)c2)CC1] |
| 59 | 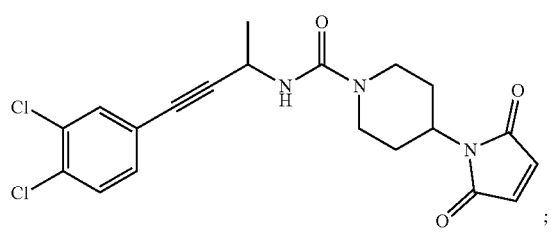 [SMILES: CC(C#Cc1ccc(Cl)c(Cl)c1)NC(=O)N1CCC(N2C(=O)C=CC2=O)CC1] |
| 60 | 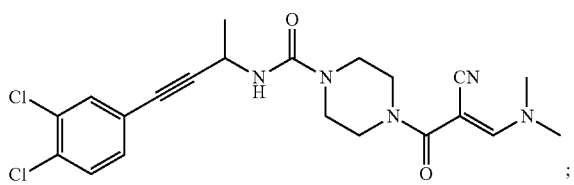 [SMILES: CC(C#Cc1ccc(Cl)c(Cl)c1)NC(=O)N1CCN(C(=O)/C(C#N)=C/N(C)C)CC1] |
| 61 | 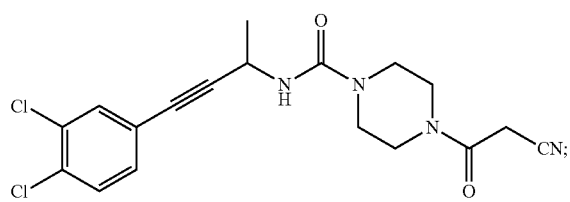 [SMILES: CC(C#Cc1ccc(Cl)c(Cl)c1)NC(=O)N1CCN(C(=O)CC#N)CC1] |
| 62 | 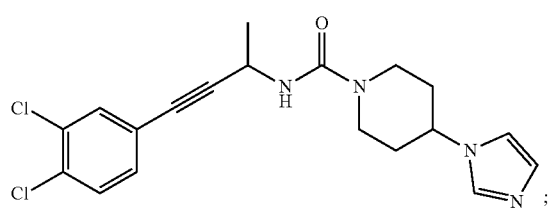 [SMILES: CC(C#Cc1ccc(Cl)c(Cl)c1)NC(=O)N1CCC(n2ccnc2)CC1] |
| 63 | 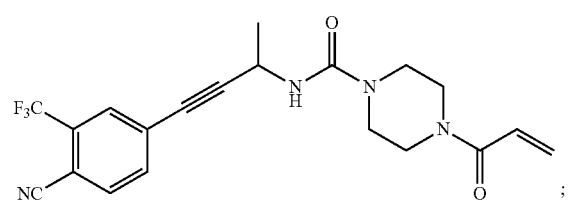 [SMILES: C=CC(=O)N1CCN(C(=O)NC(C)C#Cc2ccc(C#N)c(C(F)(F)F)c2)CC1] |
| 64 | 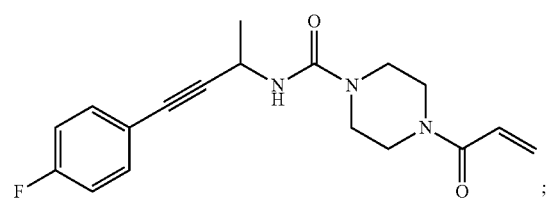 [SMILES: C=CC(=O)N1CCN(C(=O)NC(C)C#Cc2ccc(F)cc2)CC1] |

-continued

| Example | Structure |
|---|---|
| 65 | 3,4-dichlorophenyl-C≡C-CH(CH₃)-NH-C(O)-N(piperazine)-C(O)-CH=CH-C(O)NH₂ |
| 66 | 3,4-dichlorophenyl-C≡C-C(cyclopropyl)-NH-C(O)-N(piperazine)-C(O)-CH=CH-CF₃ |
| 67 | 3,4-dichlorophenyl-C≡C-C(cyclopropyl)-NH-C(O)-N(piperazine)-C(O)-C(F)=CH₂ |
| 68 | 3,4-dichlorophenyl-C≡C-C(cyclopropyl)-NH-C(O)-N(piperazine)-C(O)-(azetidin-3-yl)-N-C(O)-CH=CH₂ |
| 69 | 3,4-dichlorophenyl-C≡C-CH(CH₃)-NH-C(S)-N(piperazine)-C(O)-CH=CH₂ |
| 70 | 3,4-dichlorophenyl-C≡C-CH(CH₃)-NH-C(O)-(piperidin-4-yl)-N-C(O)-CH=CH₂ |
| 71 | 3,4-dichlorophenyl-C≡C-CH(CH₃)-NH-C(O)-(pyrrolidin-3-yl)-N-C(O)-CH=CH₂ |
| 72 | 3,4-dichlorophenyl-C≡C-CH(CH₃)-NH-C(O)-(pyrrolidin-3-yl)-N-C(O)-CH=CH₂ |

| Example | Structure |
|---|---|
| 73 | 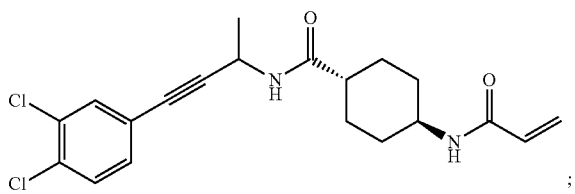 [SMILES: C=CC(=O)N[C@H]1CC[C@H](C(=O)NC(C)C#Cc2ccc(Cl)c(Cl)c2)CC1] ; |
| 74 | 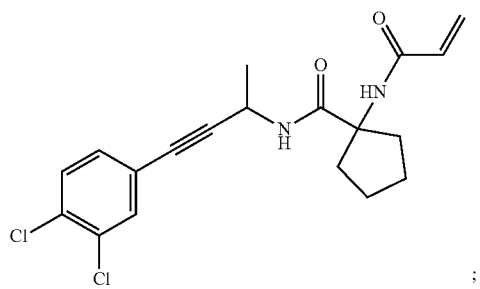 [SMILES: C=CC(=O)NC1(C(=O)NC(C)C#Cc2ccc(Cl)c(Cl)c2)CCCC1] ; |
| 75 | 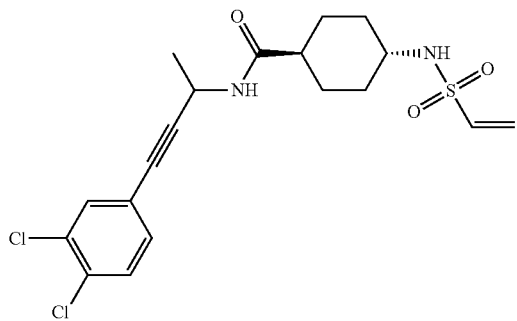 ; |
| 76 | 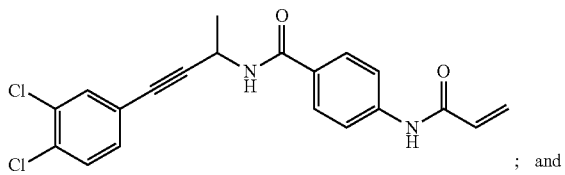 [SMILES: C=CC(=O)Nc1ccc(C(=O)NC(C)C#Cc2ccc(Cl)c(Cl)c2)cc1] ; and |
| 77 | 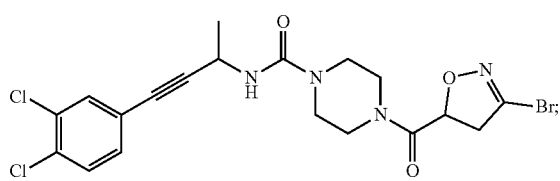 [SMILES: CC(C#Cc1ccc(Cl)c(Cl)c1)NC(=O)N1CCN(C(=O)C2CC(Br)=NO2)CC1] | or a pharmaceutically acceptable salt or a stereoisomer thereof.

26. A pharmaceutical composition comprising a compound according to claim 1, or a pharmaceutically acceptable salt or a stereoisomer thereof, and a pharmaceutically acceptable carrier or excipient.

27. The pharmaceutical composition according to claim 26, further comprising at least one additional agent selected from an anticancer agent, a chemotherapy agent, and an antiproliferative compound.

28. The compound of claim 1, having the formula:

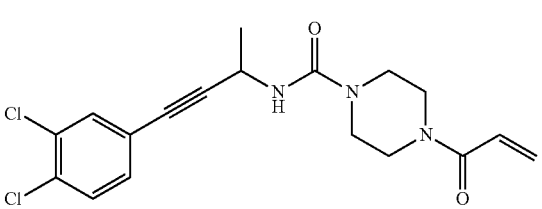

or a pharmaceutically acceptable salt thereof.

29. The compound of claim 1, having the formula:
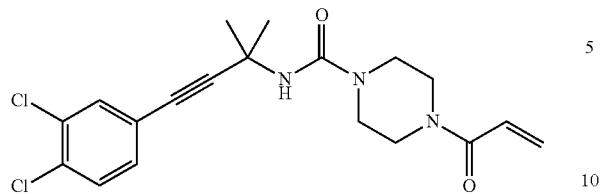
or a pharmaceutically acceptable salt thereof.
30. The compound of claim 1, having the formula:
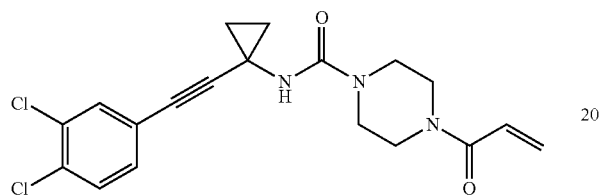
or a pharmaceutically acceptable salt thereof.
* * * * *